(12) United States Patent
Yen

(10) Patent No.: US 10,312,455 B2
(45) Date of Patent: Jun. 4, 2019

(54) DELAYED FLUORESCENCE MATERIAL FOR ORGANIC ELECTROLUMINESCENCE DEVICE

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 113 days.

(21) Appl. No.: 15/469,538

(22) Filed: Mar. 26, 2017

(65) Prior Publication Data

US 2018/0277765 A1  Sep. 27, 2018

(51) Int. Cl.
| | | |
|---|---|---|
| *H01L 51/54* | (2006.01) |
| *C09K 11/06* | (2006.01) |
| *H01L 51/00* | (2006.01) |
| *C09K 11/02* | (2006.01) |
| *C07D 495/16* | (2006.01) |
| *H01L 51/50* | (2006.01) |

(52) U.S. Cl.
CPC ........ *H01L 51/0071* (2013.01); *C07D 495/16* (2013.01); *C09K 11/02* (2013.01); *C09K 11/06* (2013.01); *H01L 51/005* (2013.01); *H01L 51/0056* (2013.01); *H01L 51/0067* (2013.01); *H01L 51/0074* (2013.01); *H01L 51/0085* (2013.01); *C09K 2211/1007* (2013.01); *C09K 2211/1029* (2013.01); *C09K 2211/1059* (2013.01); *C09K 2211/185* (2013.01); *H01L 51/5012* (2013.01); *H01L 51/5016* (2013.01)

(58) Field of Classification Search
CPC ..... C09K 11/02; C09K 11/06; C09K 2211/10; C09K 2211/1007; C09K 2211/1029; C09K 2211/1059; C09K 2211/185; H01L 51/0032; H01L 51/005; H01L 51/0056; H01L 51/0071; H01L 51/0072; H01L 51/0074; H01L 51/0085; H01L 51/50; H01L 51/5012; H01L 51/5016; C07D 495/00; C07D 495/02; C07D 495/04; C07D 495/10; C07D 495/16

USPC ....... 428/690, 691, 917, 411.4, 336; 427/58, 427/66; 313/500–512; 252/301.16–301.35; 257/40, 88–104, 257/E51.001–E51.052
See application file for complete search history.

(56) References Cited

U.S. PATENT DOCUMENTS

2016/0111660 A1* 4/2016 Yang ................... H01L 51/5004
257/40

FOREIGN PATENT DOCUMENTS

WO   2011/060867 A1   5/2011

* cited by examiner

*Primary Examiner* — Andrew K Bohaty

(57) ABSTRACT

The present invention discloses a delayed fluorescence material having general formula (1), and an organic EL device using the material as delayed fluorescence material of emitting layer or phosphorescent light emitting host of emitting layer can display excellent performance.

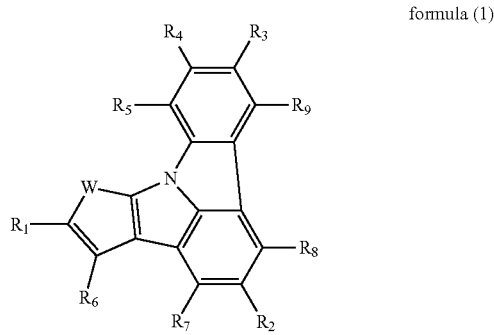

formula (1)

wherein W independently represents an oxygen atom, a sulfur atom and a selenium atom, $R_1$ to $R_9$ are the same definition as described in the present invention.

13 Claims, 2 Drawing Sheets

DELAYED FLUORESCENCE MATERIAL FOR ORGANIC ELECTROLUMINESCENCE DEVICE

FIELD OF INVENTION

The present invention relates to a material and organic electroluminescence (herein referred to as organic EL) device using the material. More specifically, the present invention relates to a delayed fluorescence material having general formula (1), and an organic EL device using the material as delayed fluorescence material of emitting layer or phosphorescent light emitting host of emitting layer can display excellent performance.

BACKGROUND OF THE INVENTION

Organic EL is applied in flat panel displays due to their high illumination, low weight, ultra-thin profile, self-illumination without back light, low power consumption, wide viewing angle, high contrast, simple fabrication methods and rapid response time.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

A new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent host for emitting layer are still unsatisfactory in half-lifetime, efficiency and driving voltage for industrial practice use. Besides, in order to display excellent performance of organic EL devices, the phosphorescent light emitting host material need to collocate with other organic thin film layer such as hole blocking layer and electron transporting layer to get lower power consumption, longer half-life time and higher efficiency. Therefore, there is a demand for designing and developing novel material for organic EL devices.

In the present invention, for the purpose to prolong the half-life time, higher efficiency and display excellent performance for dipolar materials of delayed fluorescence compound for organic EL device, we employ skeleton formula (1) act as donor and utilize $R_1$, $R_2$ and $R_3$ positions of the skeleton link to acceptor characteristic of triazinyl group, diazinyl group, pyridinyl group, quinoline group, isoquinoline group, sulfonyldibenzene group, benzophenone group and other electron acceptor group to finish the delayed fluorescence material as general formula (1) shown excellent performance.

SUMMARY OF THE INVENTION

According to the reasons described above, the present invention has the objective of resolving such problems of the prior art and offering a light emitting device which is excellent in its thermal stability, high luminance efficiency and long half-life time. The present invention disclose a delayed fluorescence compound having general formula (1), used as delayed fluorescence material of emitting layer or phosphorescent light emitting host of emitting layer having good charge carrier mobility and excellent operational durability can lower driving voltage and power consumption, increasing efficiency and half-life time of organic EL device.

The present invention has the economic advantages for industrial practice. Accordingly, the present invention discloses the delayed fluorescence material which can be used for organic EL device is disclosed. The mentioned the delayed fluorescence material represented by the following formula (1):

formula (1)

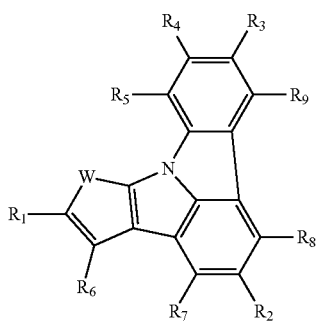

wherein W independently represents an oxygen atom, a sulfur atom and a selenium atom; $R_1$, $R_2$ and $R_3$ are independently selected from the group consisting of a hydrogen atom, a deuterium atom, a halide, formula (2) or formula (3):

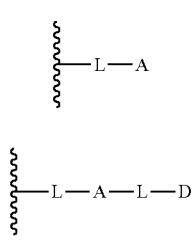

formula (2)

formula (3)

D is an electron donor represented from formula (1), a substituted or unsubstituted carbazolyl group, a substituted or unsubstituted biscarbazolyl group, a substituted or unsubstituted dihydroacridine group, a substituted or unsubstituted phenoxazine group and a substituted or unsubstituted diarylamine group; A is an electron acceptor selected from the group consisting of the following formulas:

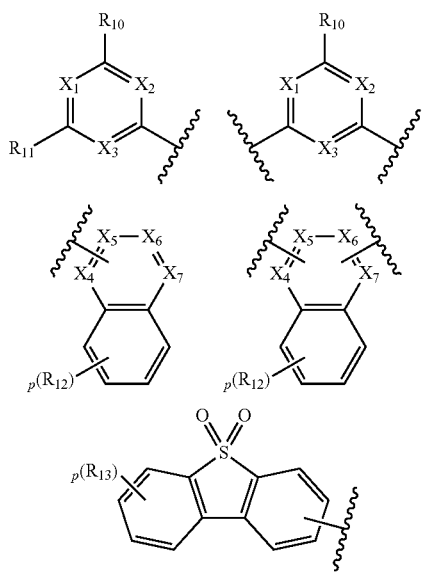

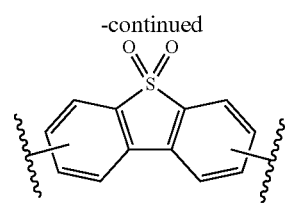

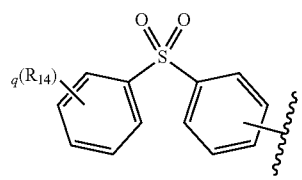

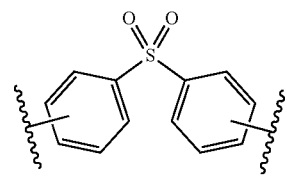

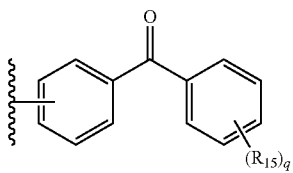

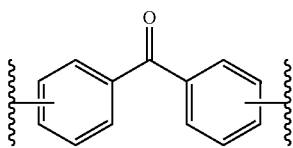

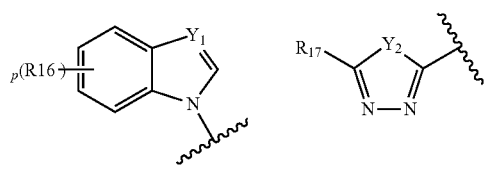

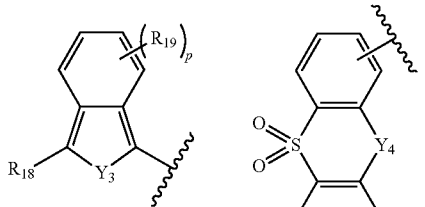

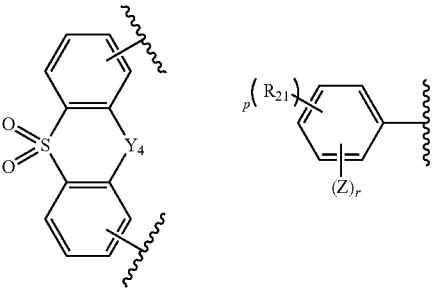

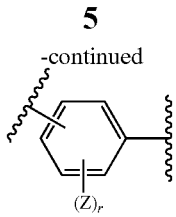

L represents a single bond or a substituted or unsubstituted divalent arylene group having 6 to 30 ring carbon atoms, p represents an integer of 0 to 4, q represents an integer of 0 to 5, r represents an integer of 1 to 4, $Y_1$ to $Y_4$ is a divalent bridge selected from the atom or group consisting from O, S, $C(R_{22})(R_{23})$, $NR_{24}$, and $Si(R_{25})(R_{26})$, $X_1$ to $X_7$ represent a nitrogen atom or $C(R_s)$, and each $R_s$ represents a hydrogen, a phenyl, a substituted or unsubstituted alkyl group having 1 to 30 carbon atoms, or a substituted or unsubstituted aryl group having 6 to 30 carbon atoms, Z represents a cyano group or a fluorine atom, $R_4$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

DESCRIPTION OF THE PREFERRED EMBODIMENTS

Figure 1:
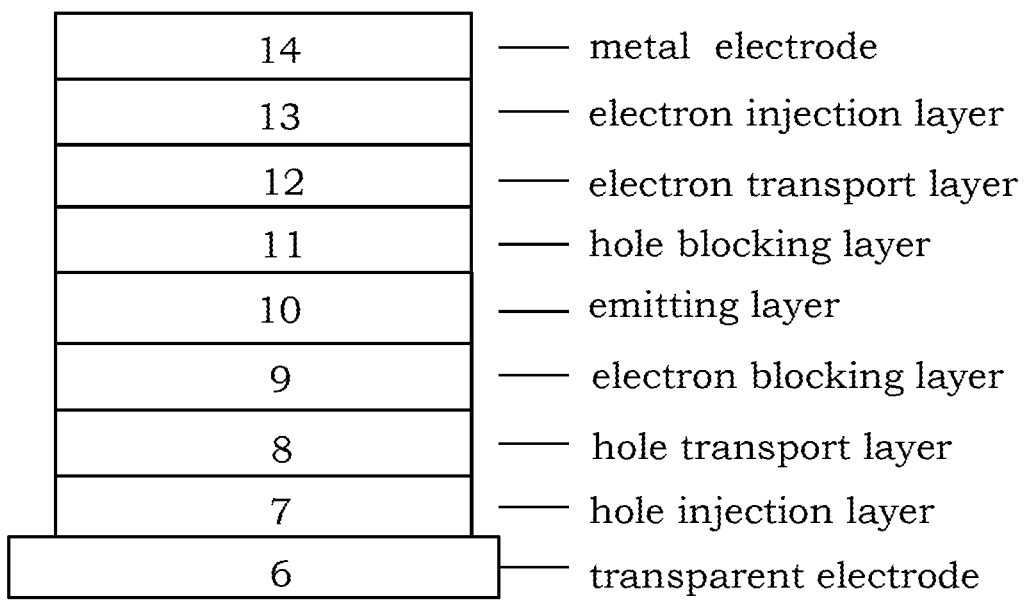
FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is emitting layer which is deposited onto 9, 11 is hole blocking layer which is deposited onto 10, 12 is electron transport layer which is deposited on to 11, and 13 is electron injection layer which is deposited on to 12.

What probed into the invention is the delayed fluorescence material for organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the delayed fluorescence material which can be used as a delayed fluorescence (TADF) material of emitting layer for organic EL device are disclosed. The mentioned the delayed fluorescence material represented by the following formula (1):

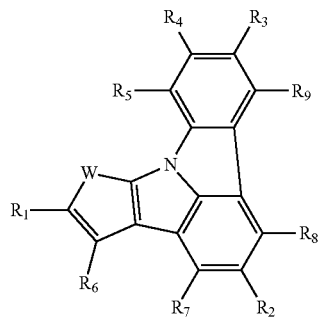

formula (1)

wherein W independently represents an oxygen atom, a sulfur atom and a selenium atom; $R_1$, $R_2$ and $R_3$ are independently selected from the group consisting of a hydrogen atom, a deuterium atom, a halide, formula (2) or formula (3):

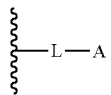

formula (2)

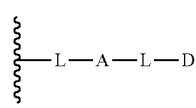

formula (3)

D is an electron donor represented from formula (1), a substituted or unsubstituted carbazolyl group, a substituted or unsubstituted biscarbazolyl group, a substituted or unsubstituted dihydroacridine group, a substituted or unsubstituted phenoxazine group and a substituted or unsubstituted diarylamine group; A is an electron acceptor selected from the group consisting of the following formulas:

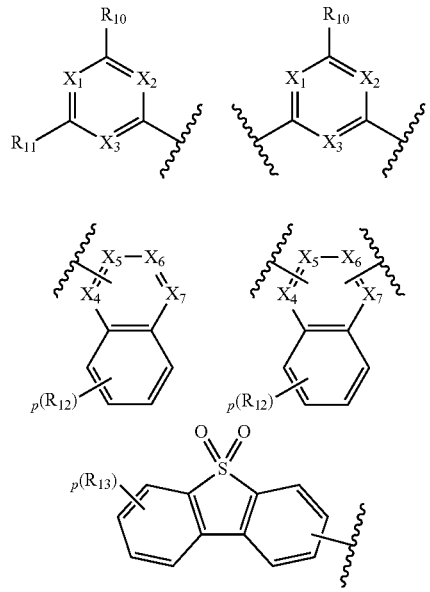

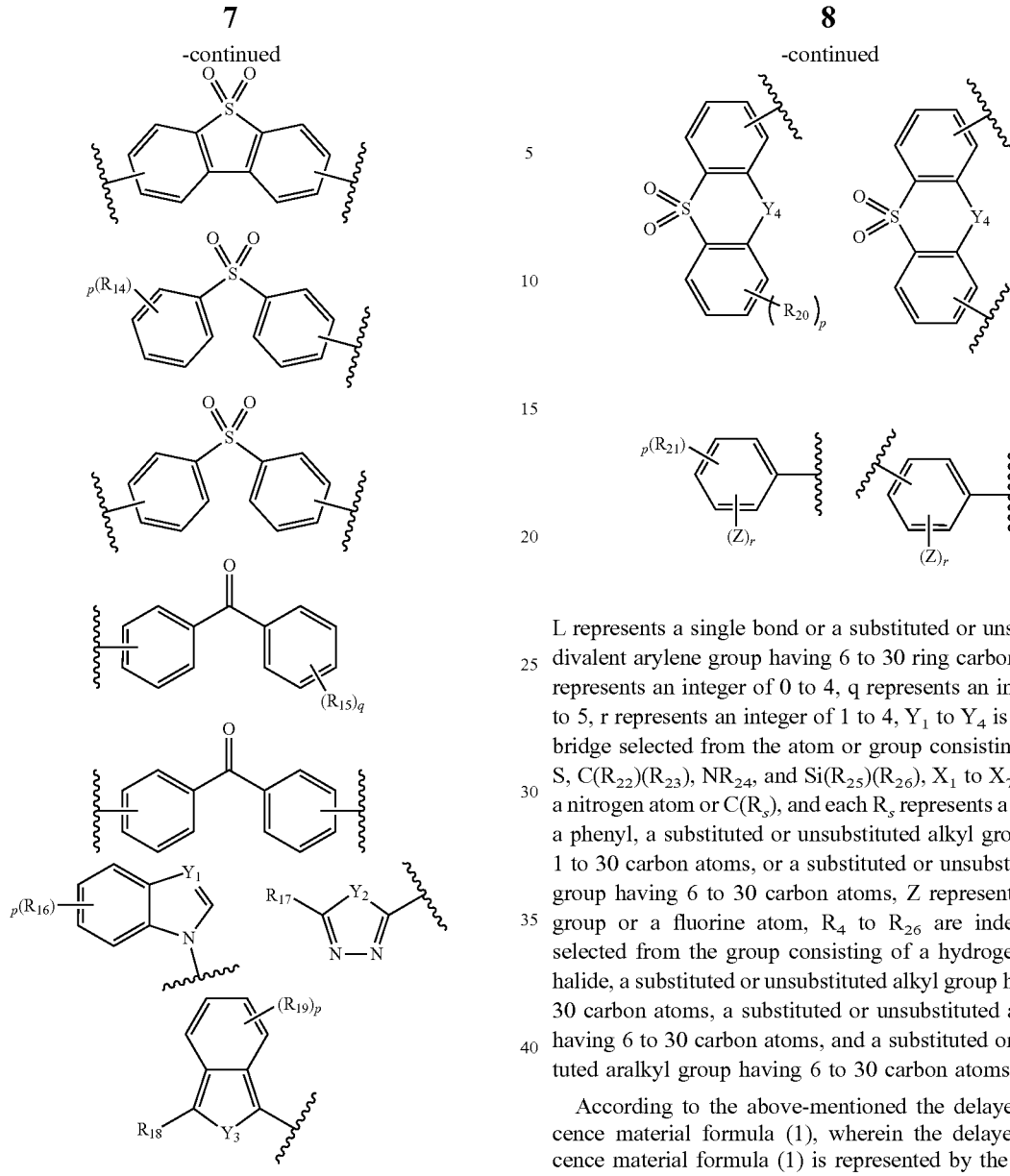

L represents a single bond or a substituted or unsubstituted divalent arylene group having 6 to 30 ring carbon atoms, p represents an integer of 0 to 4, q represents an integer of 0 to 5, r represents an integer of 1 to 4, $Y_1$ to $Y_4$ is a divalent bridge selected from the atom or group consisting from O, S, $C(R_{22})(R_{23})$, $NR_{24}$, and $Si(R_{25})(R_{26})$, $X_1$ to $X_7$ represent a nitrogen atom or $C(R_s)$, and each $R_s$ represents a hydrogen, a phenyl, a substituted or unsubstituted alkyl group having 1 to 30 carbon atoms, or a substituted or unsubstituted aryl group having 6 to 30 carbon atoms, Z represents a cyano group or a fluorine atom, $R_4$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

According to the above-mentioned the delayed fluorescence material formula (1), wherein the delayed fluorescence material formula (1) is represented by the following formula (4) to formula (12)

formula (4)

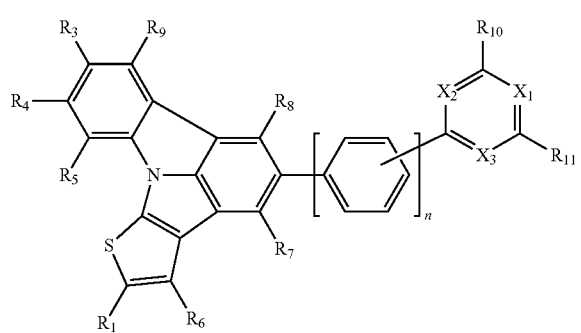

-continued
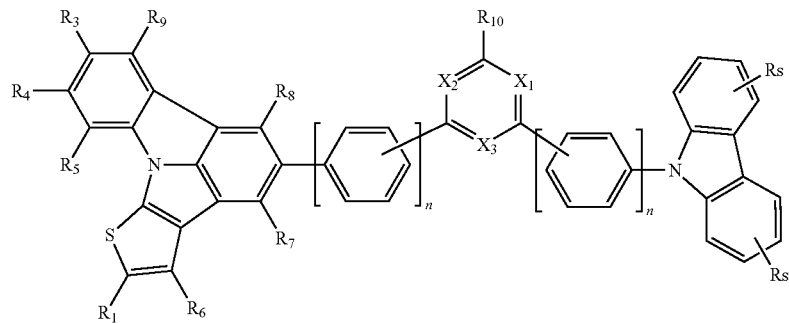
formula (5)
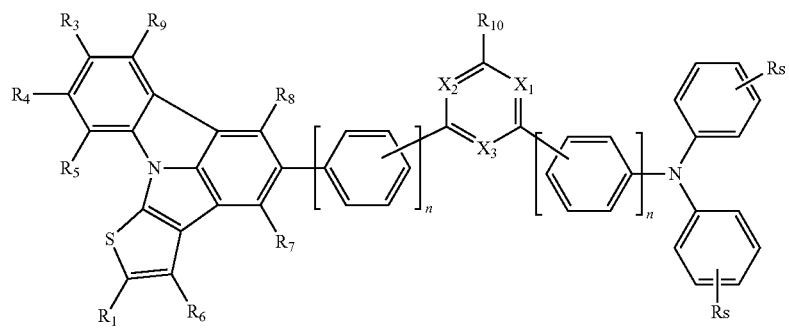
formula (6)
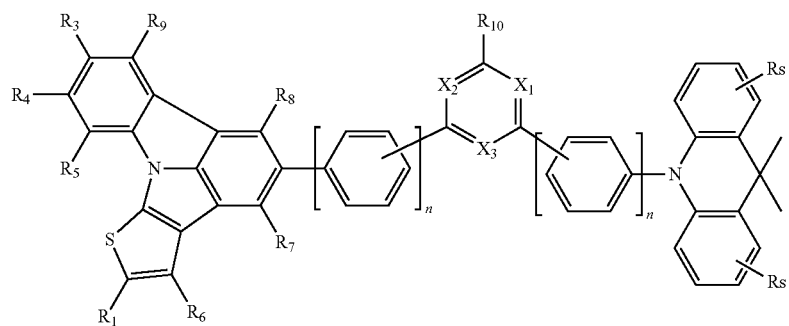
formula (7)
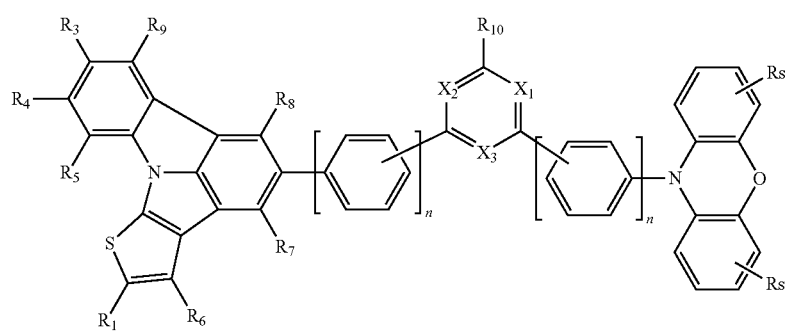
formula (8)

-continued
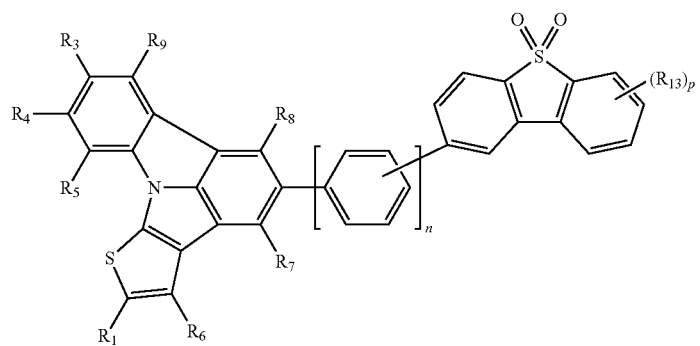
formula (9)
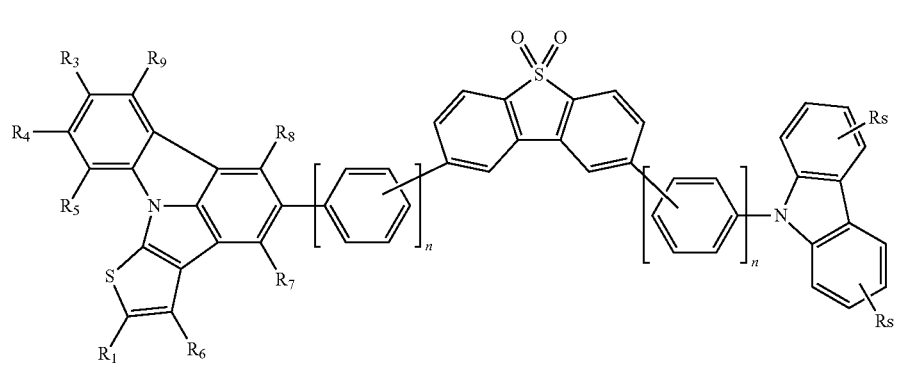
formula (10)
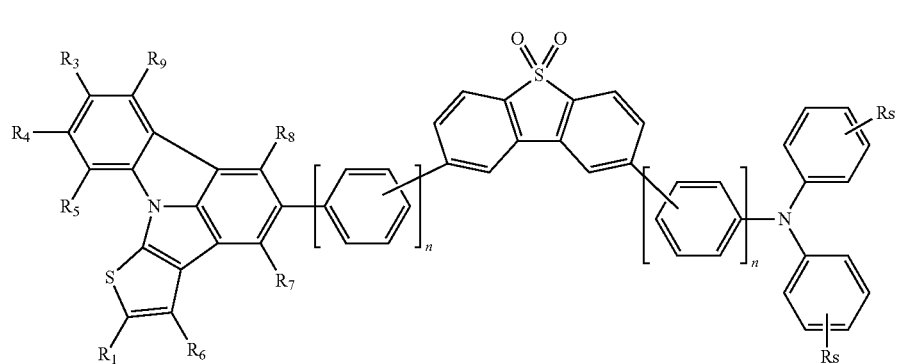
formula (11)
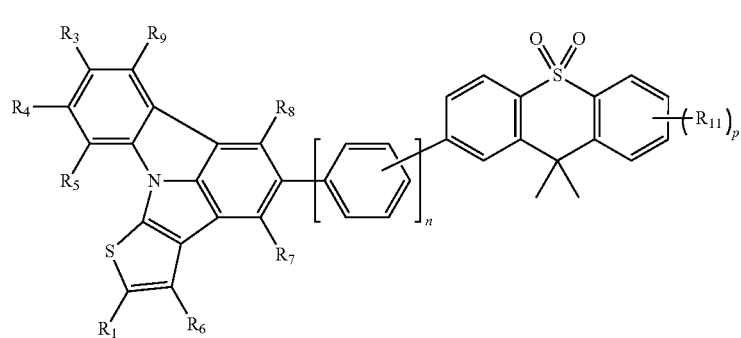
formula (12)

formula (13)

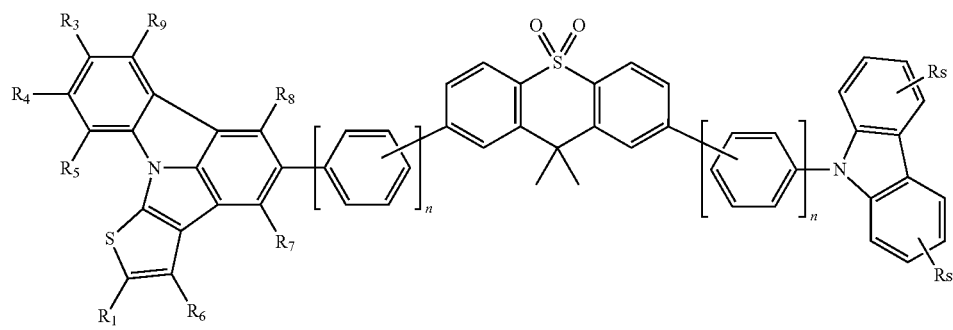

formula (14)

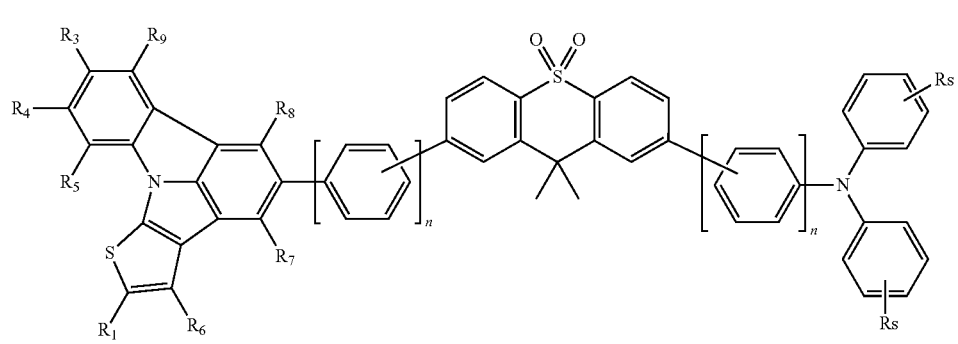

formula (15)

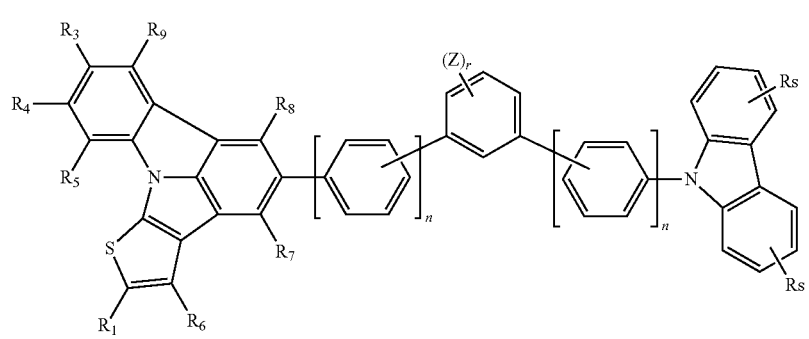

n represents an integer of 0 or 1, p represents an integer of 0 to 4, q represents an integer of 0 to 5, r represents an integer of 1 to 4, $X_1$ to $X_3$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms, Z represents a cyano group or a fluorine atom, $R_1$ to $R_{13}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

In this embodiment, some delayed fluorescence materials are shown below:
Compound 1
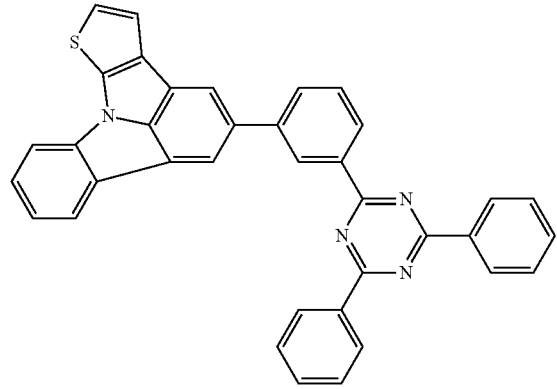
Compound 2
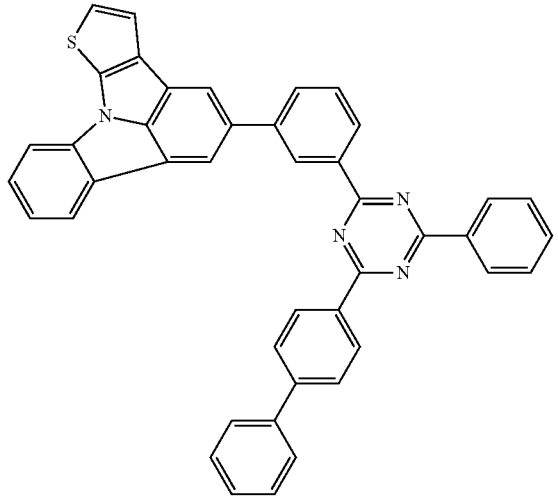
Compound 3
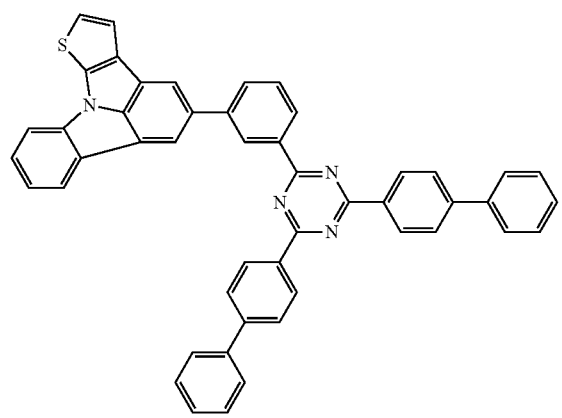
Compound 4
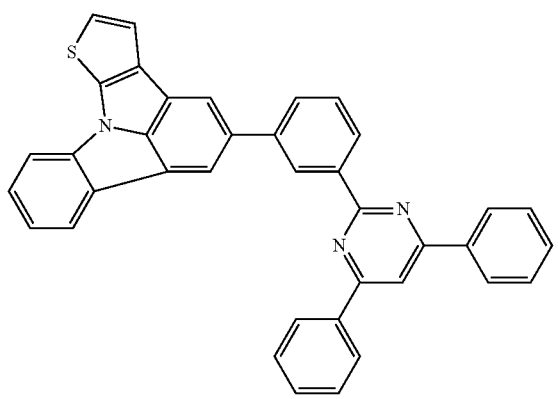
Compound 5
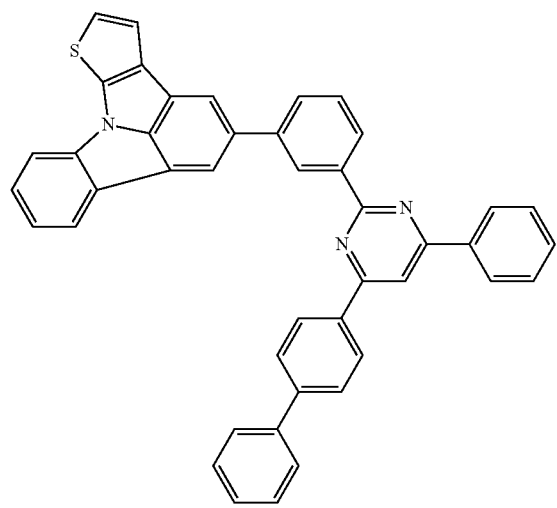
Compound 6
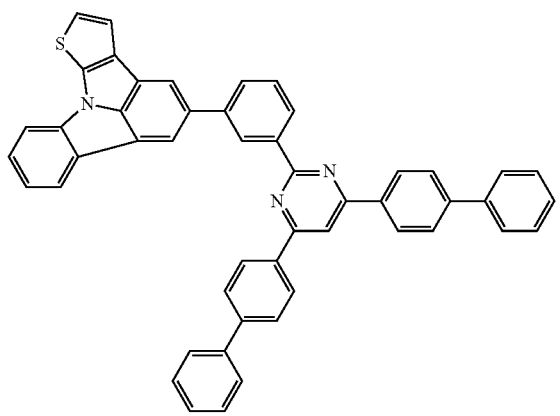

-continued
Compound 7
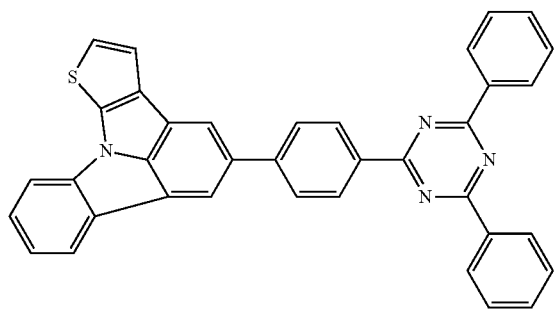
Compound 8
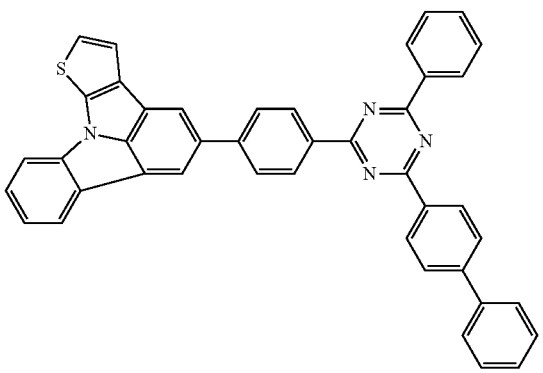
Compound 9
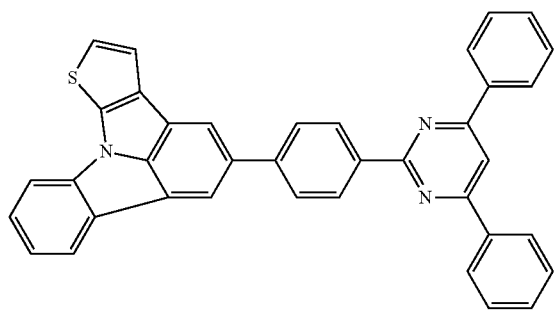
Compound 10
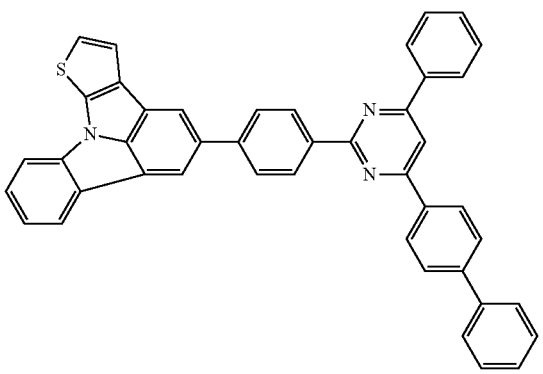
Compound 11
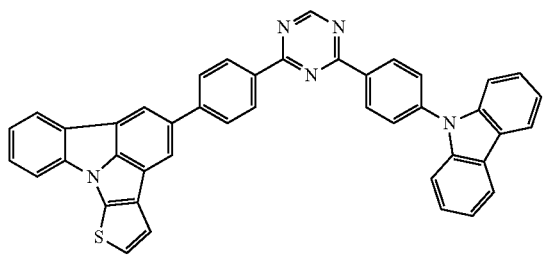
Compound 12
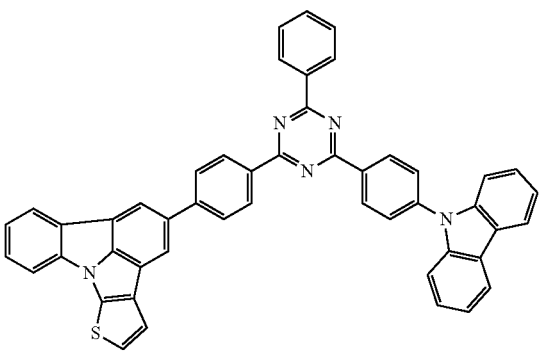
Compound 13
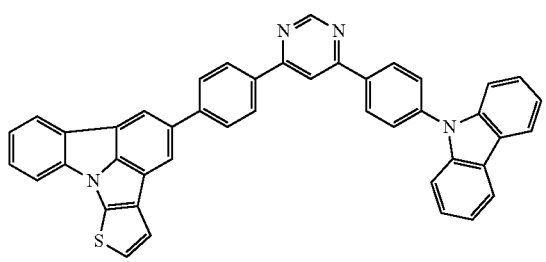
Compound 14
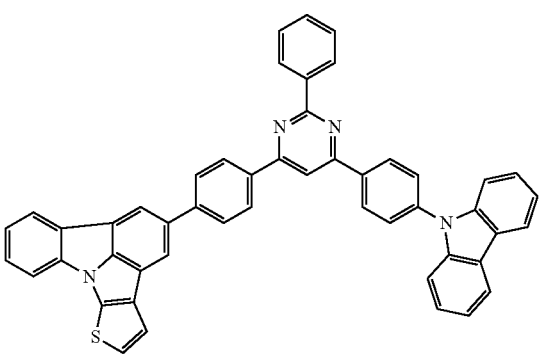

-continued
Compound 15
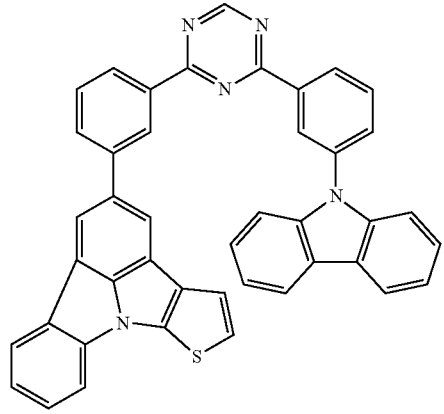
Compound 16
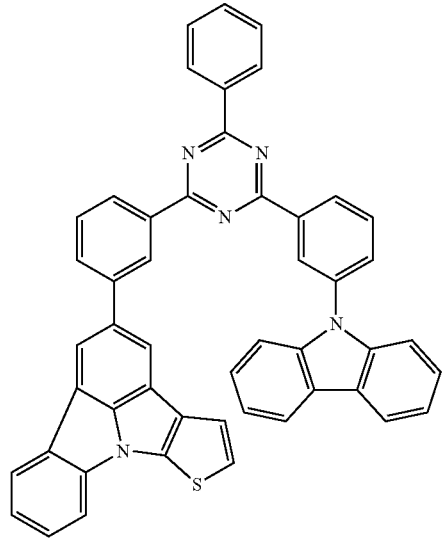
Compound 17
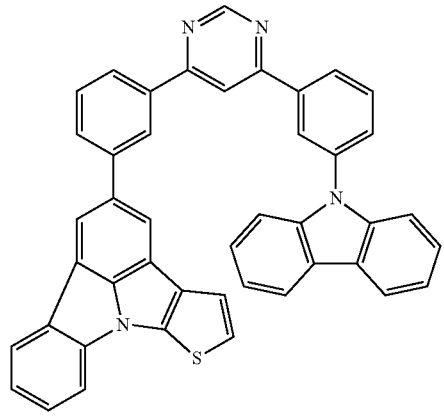
Compound 18
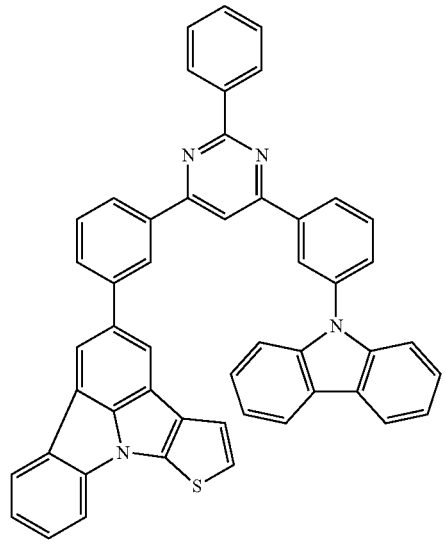
Compound 19
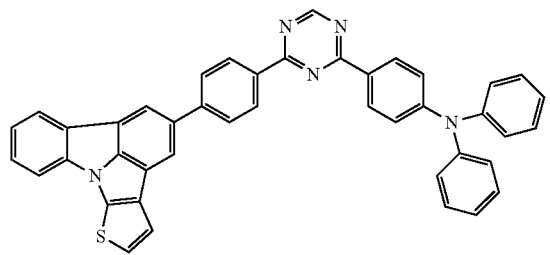
Compound 20
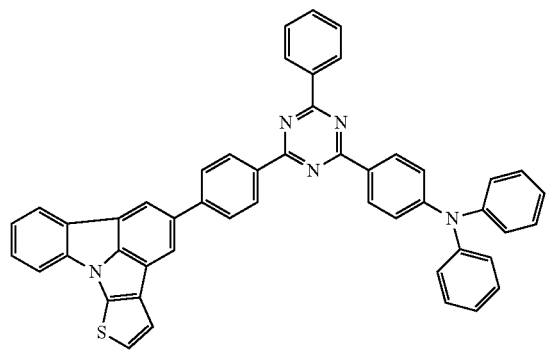

Compound 21
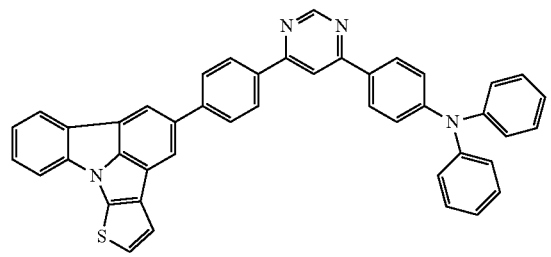
Compound 22
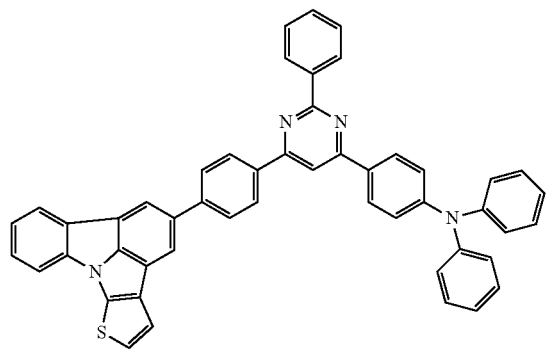
Compound 23
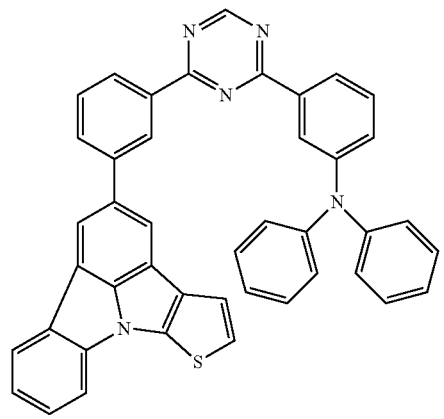
Compound 24
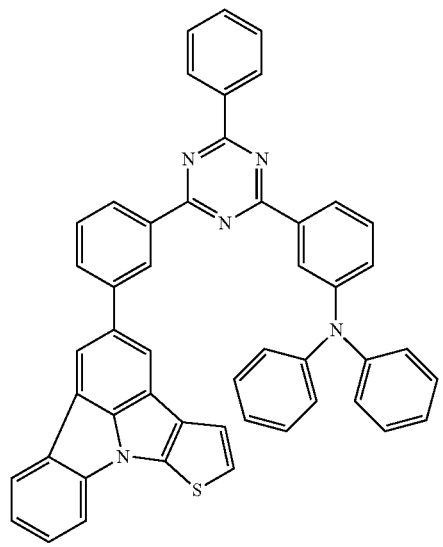
Compound 25
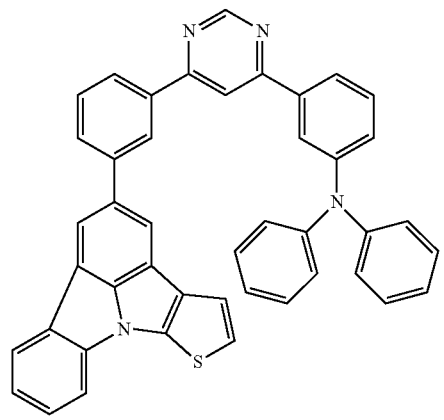
Compound 26
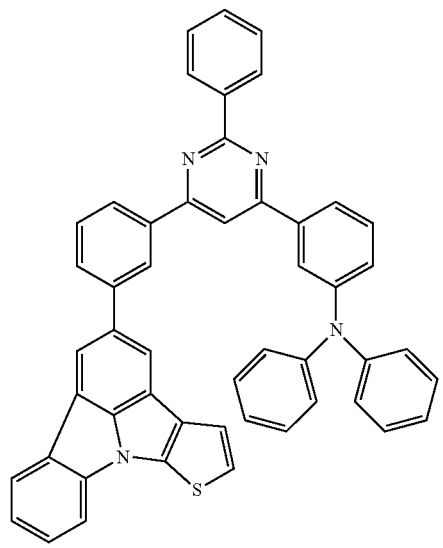

-continued
Compound 27
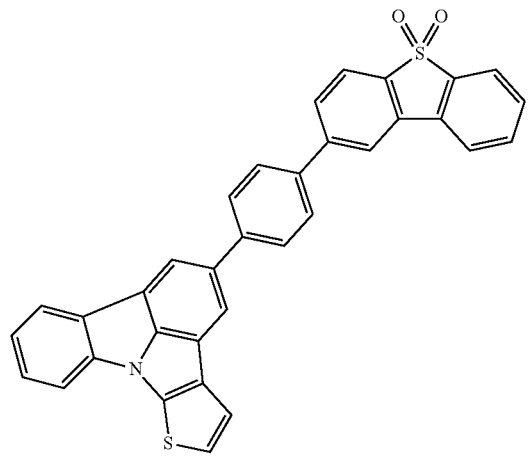
Compound 28
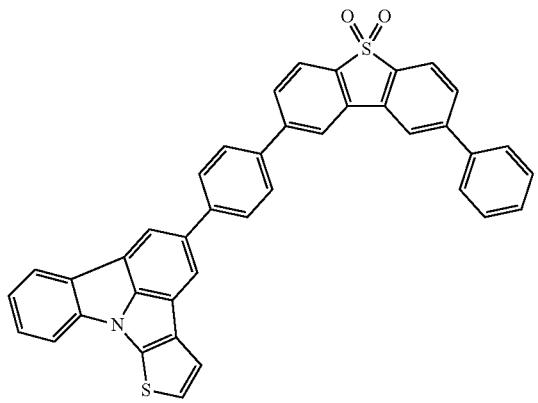
Compound 29
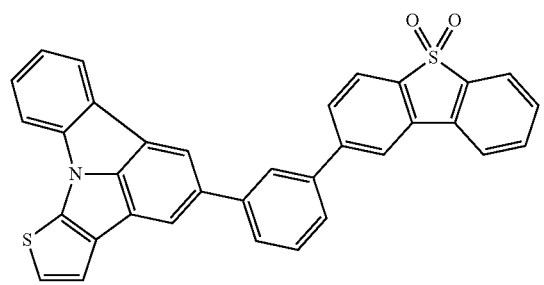
Compound 30
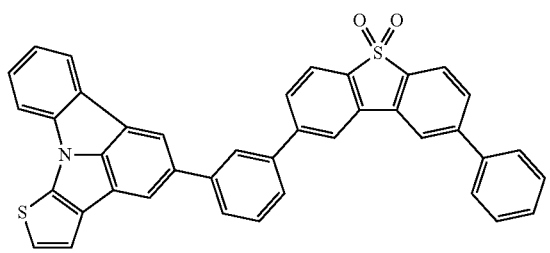
Compound 31
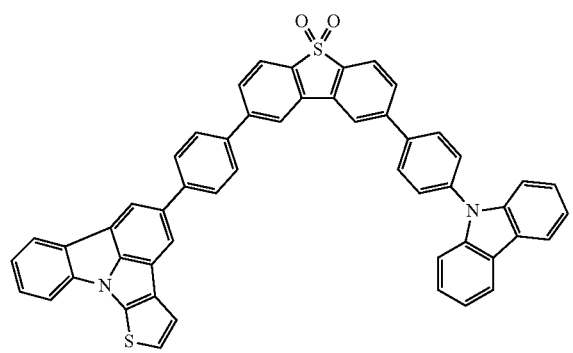
Compound 32
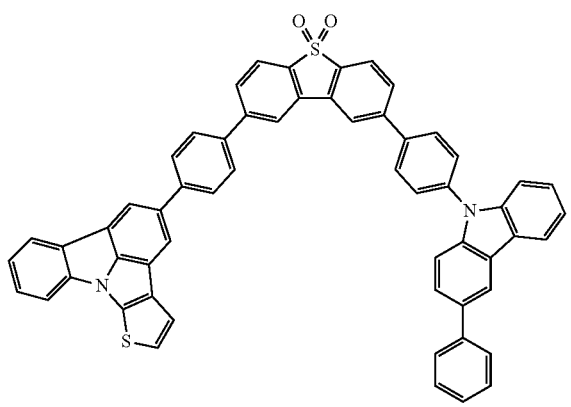

-continued
Compound 33
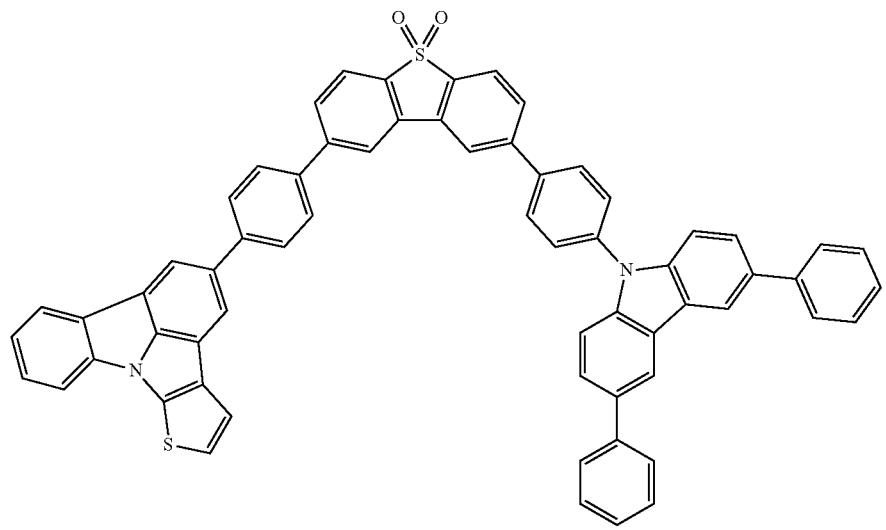
Compound 34
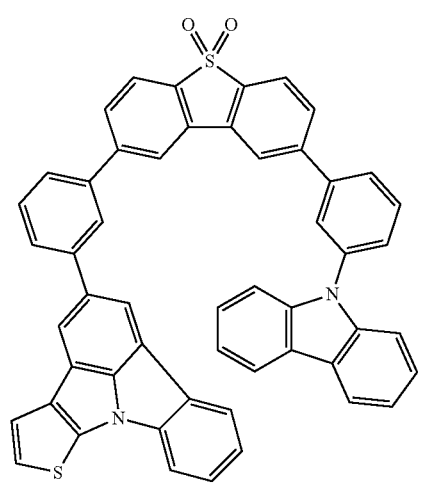
Compound 35
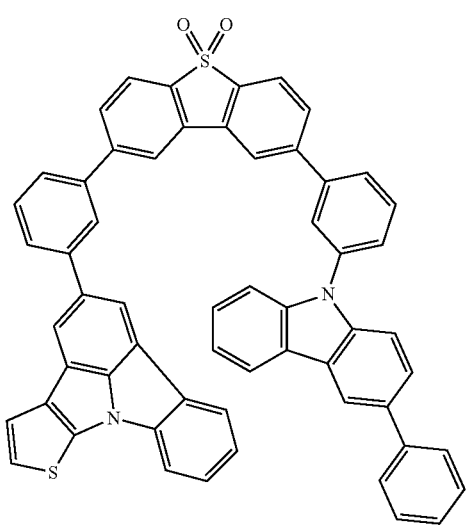
Compound 36
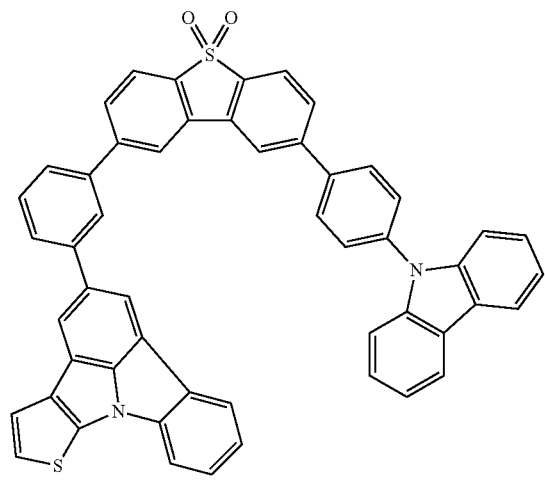
Compound 37
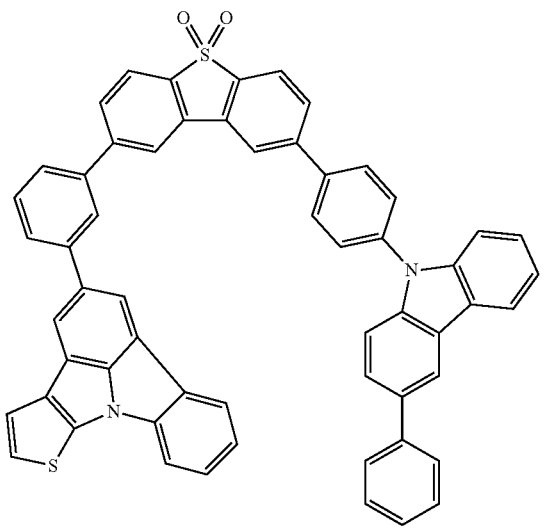

-continued
Compound 38
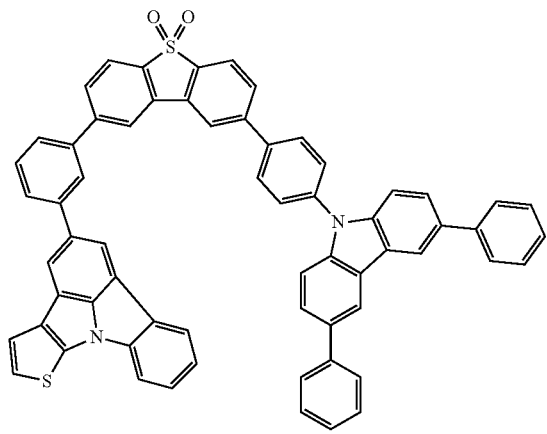
Compound 39
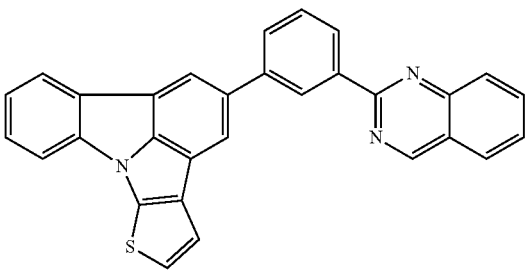
Compound 40
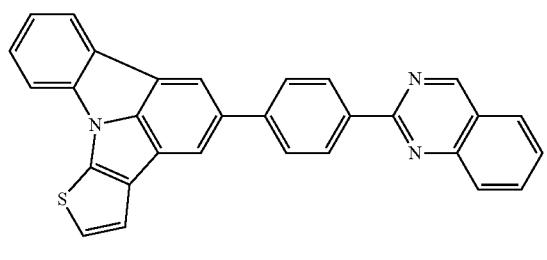
Compound 41
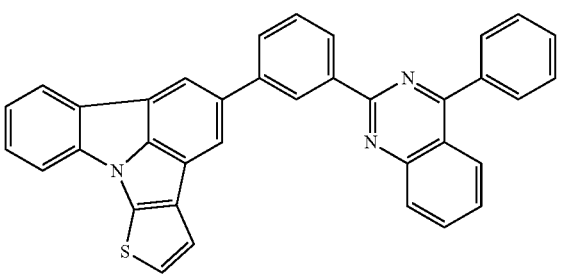
Compound 42
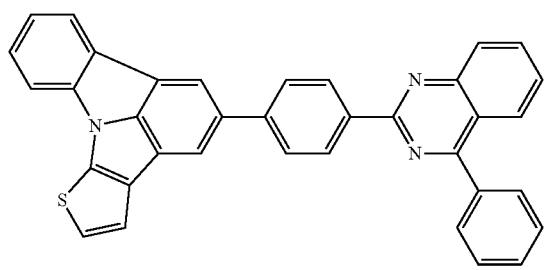
Compound 43
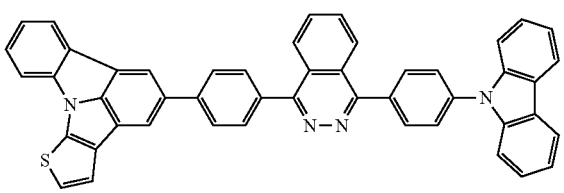
Compound 44
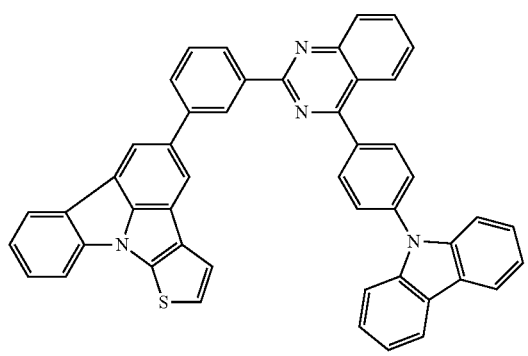
Compound 45
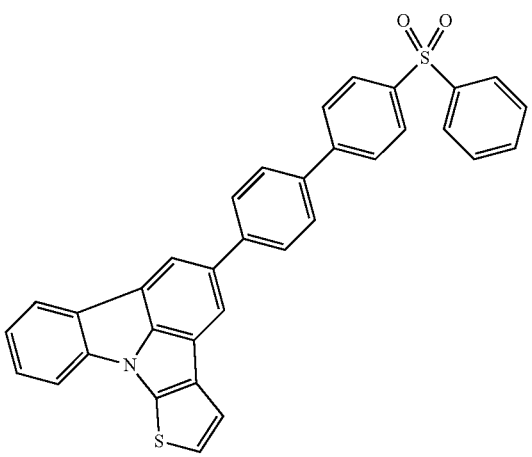

-continued
Compound 46
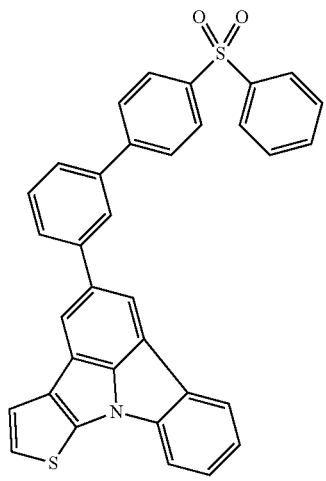
Compound 47
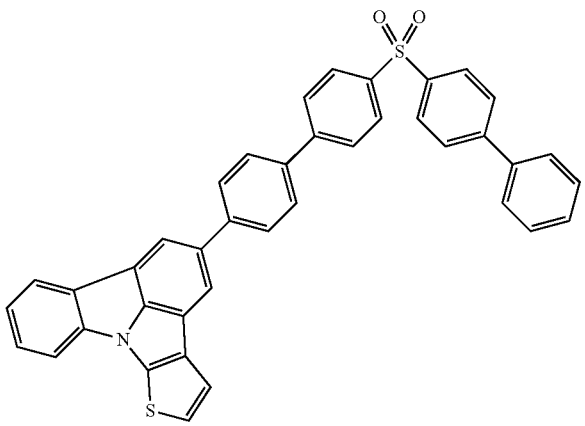
Compound 48
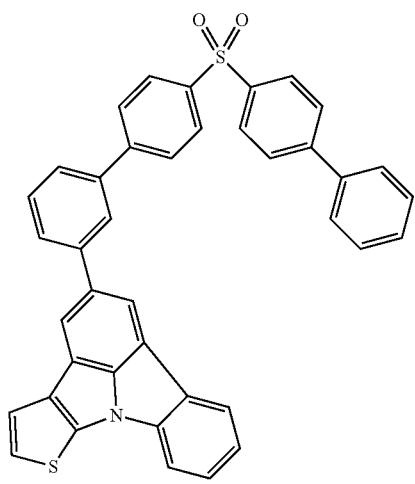
Compound 49
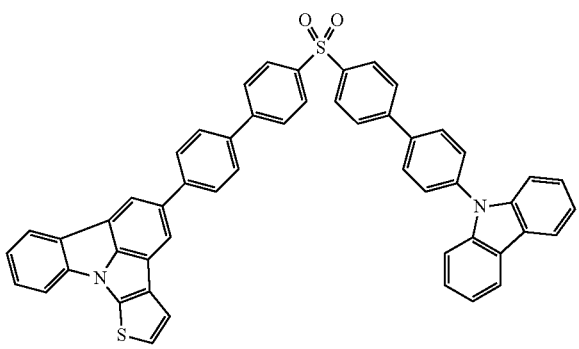
Compound 50
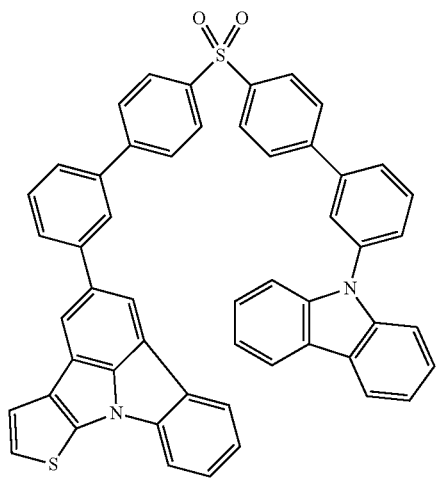
Compound 51
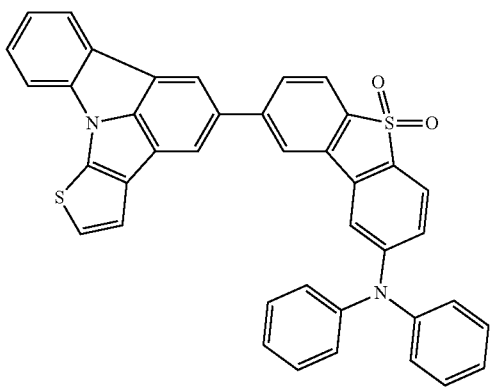

Compound 52
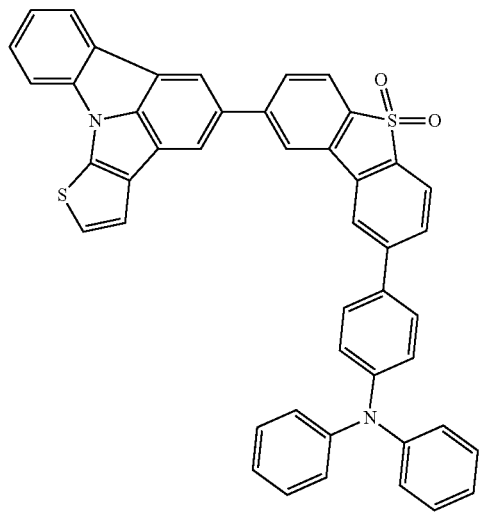
Compound 53
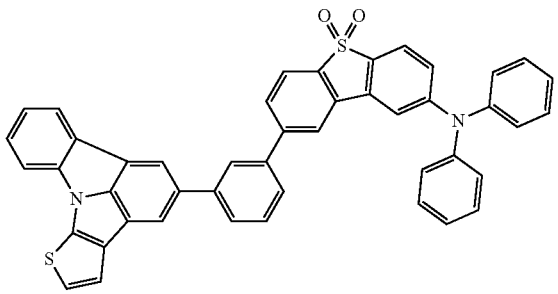
Compound 54
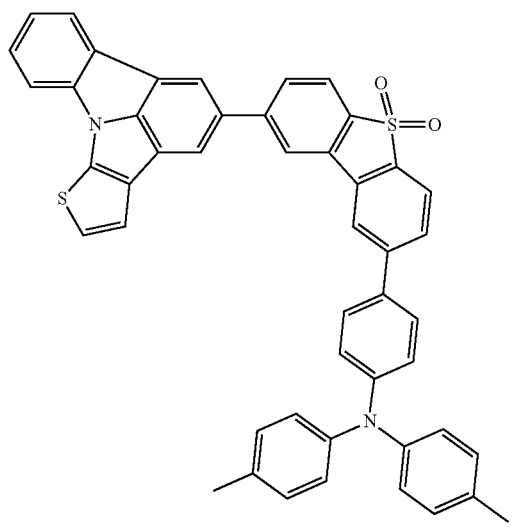
Compound 55
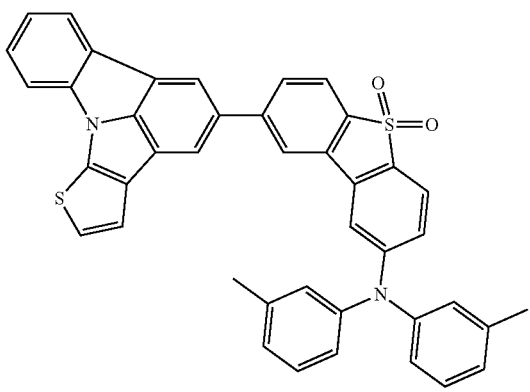
Compound 56
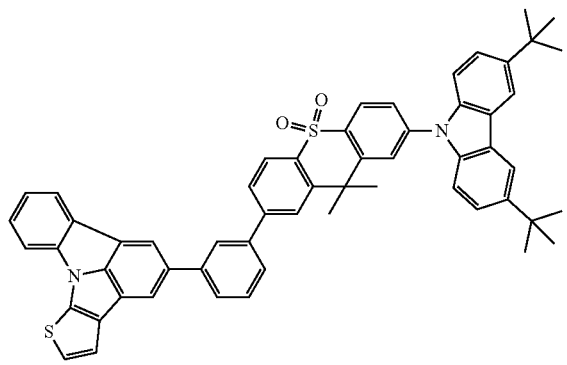
Compound 57
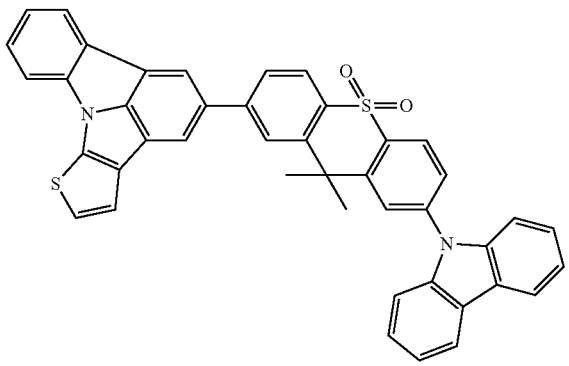

-continued
Compound 58
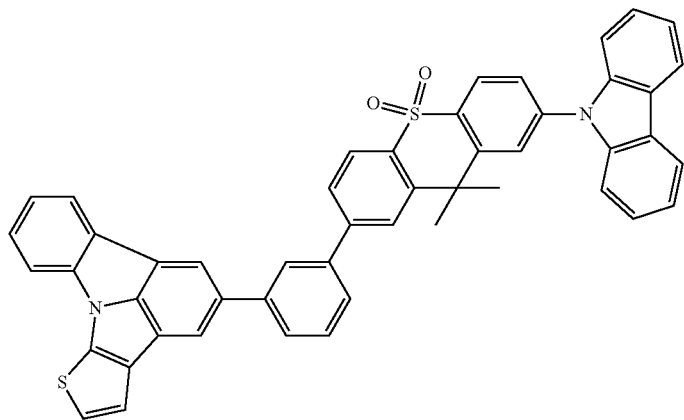
Compound 59
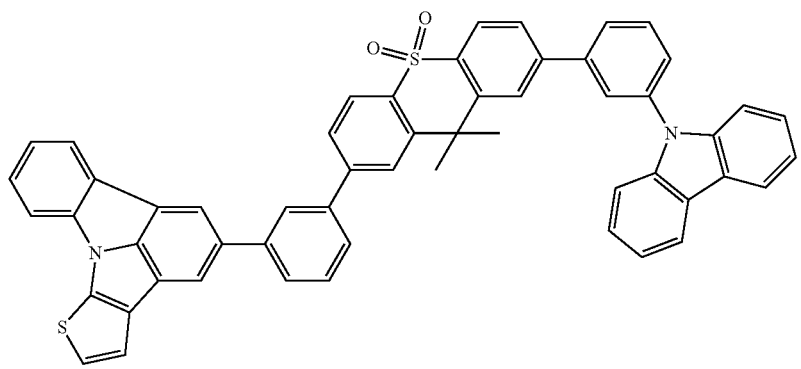
Compound 60
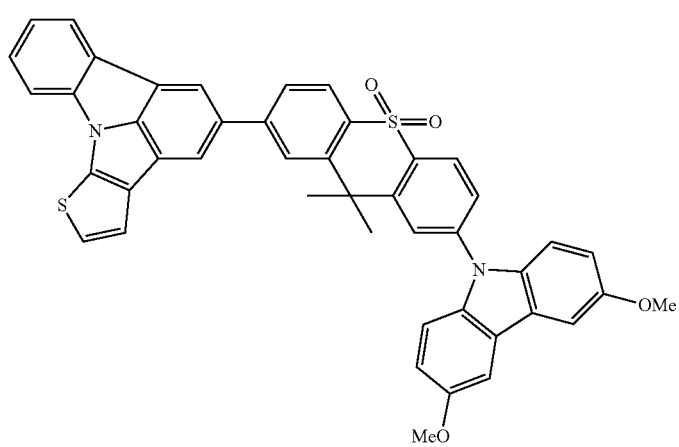

-continued
Compound 61
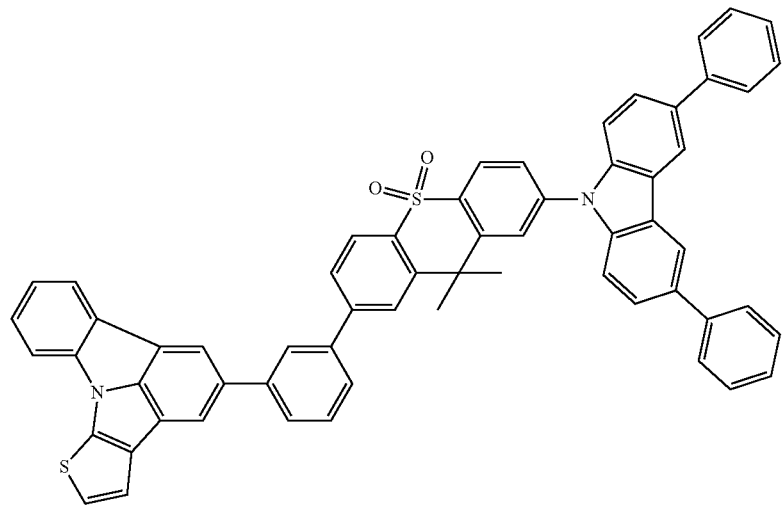
Compound 62
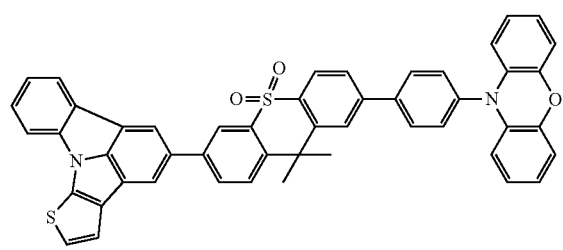
Compound 63
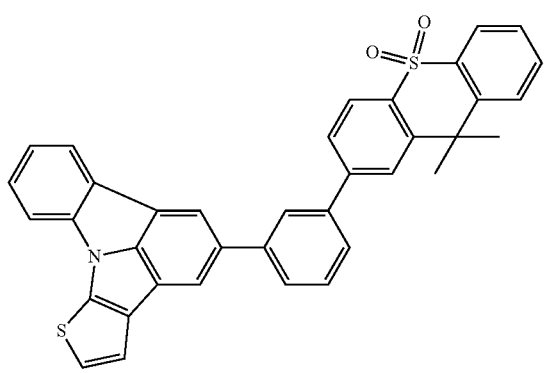
Compound 64
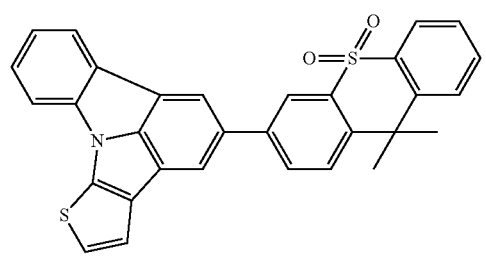
Compound 65
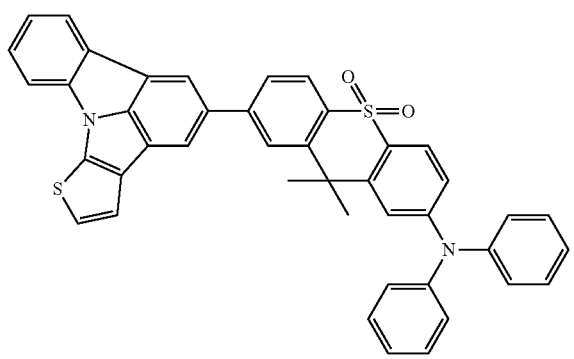

Compound 66
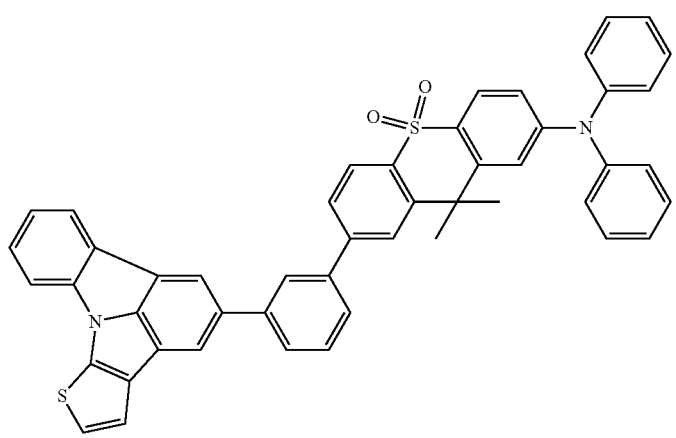
Compound 67
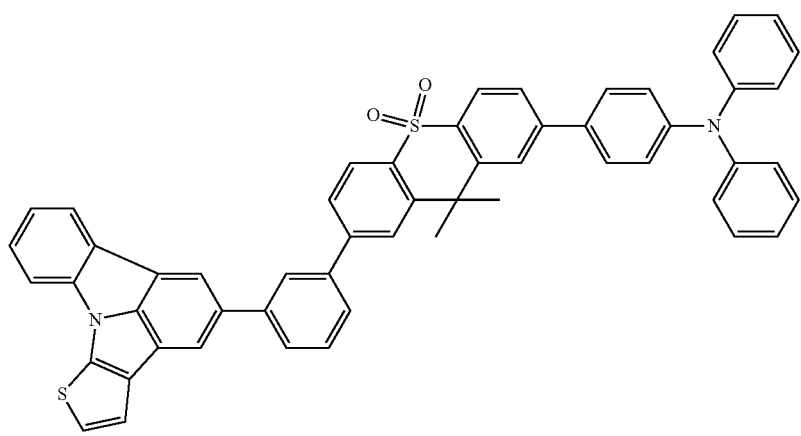
Compound 68
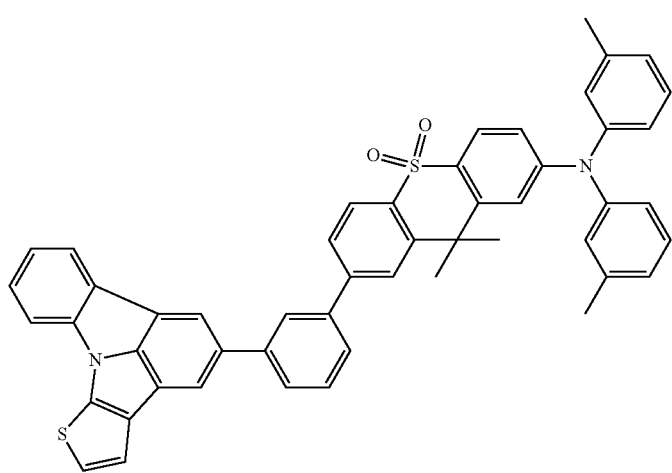

-continued
Compound 69
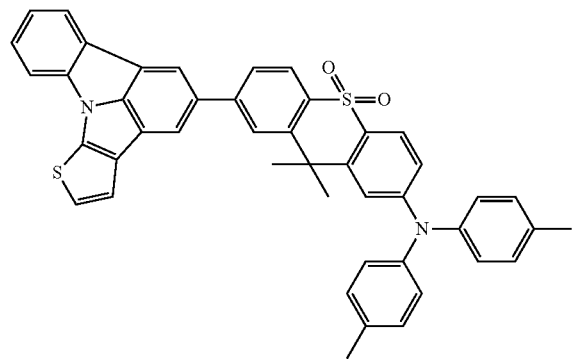
Compound 70
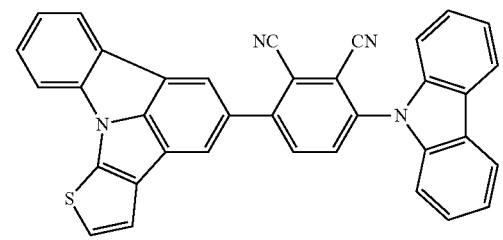
Compound 71
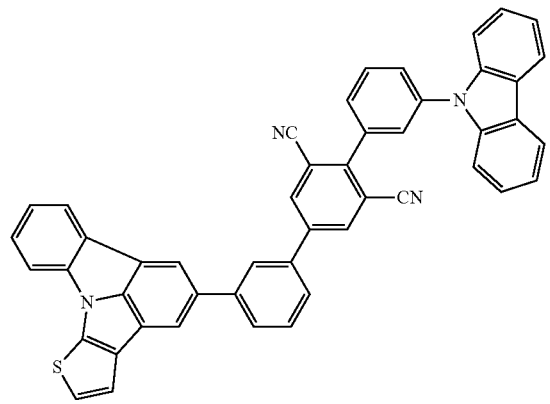
Compound 72
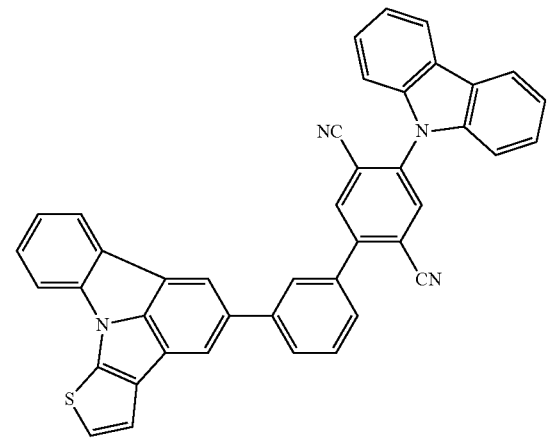
Compound 73
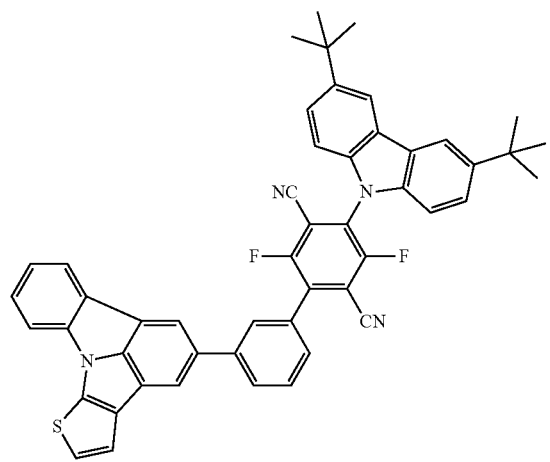
Compound 74
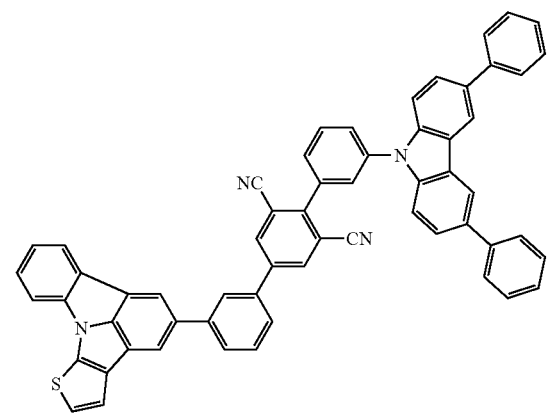

-continued
Compound 75
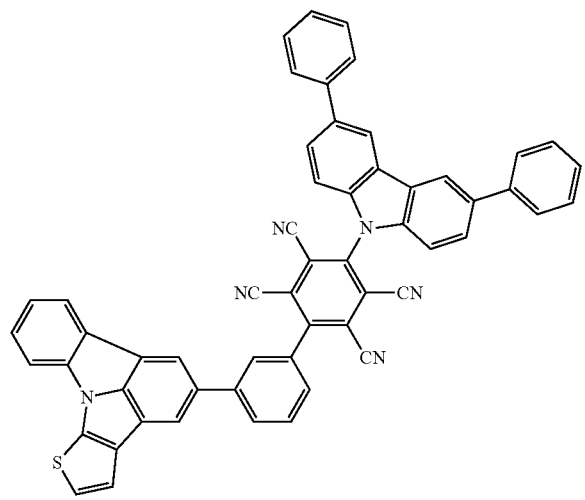
Compound 76
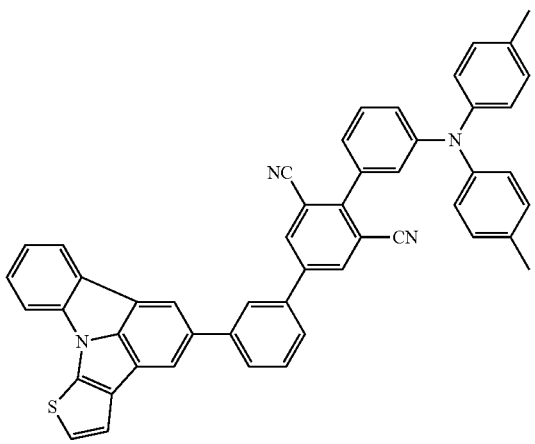
Compound 77
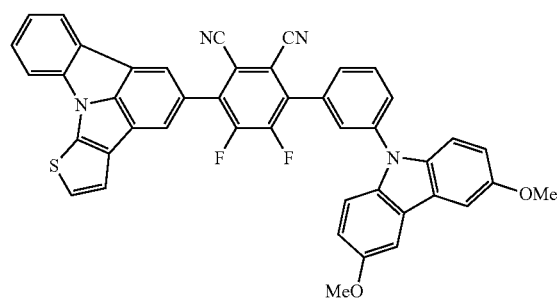
Compound 78
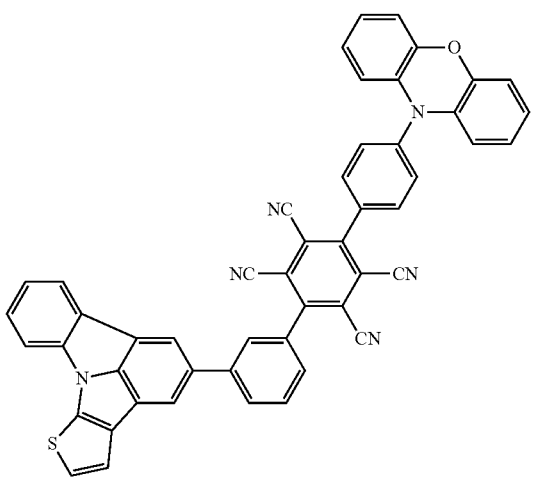
Compound 79
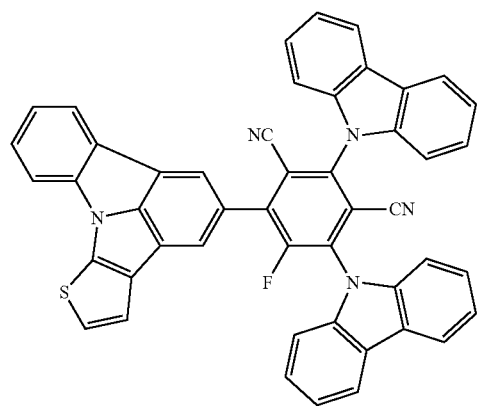
Compound 80
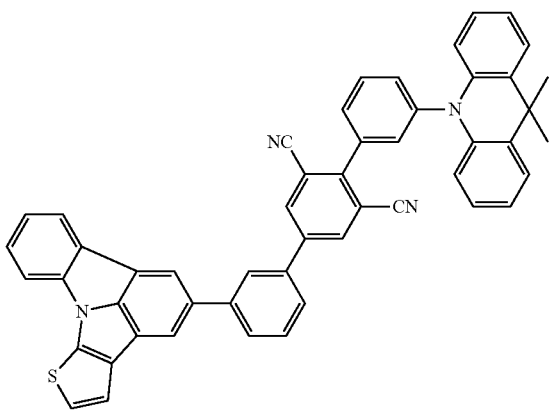

-continued
Compound 81
Compound 82
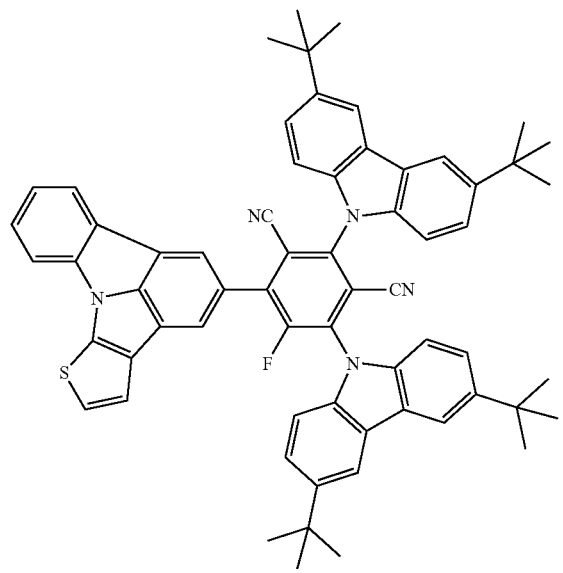
Compound 83
Compound 84
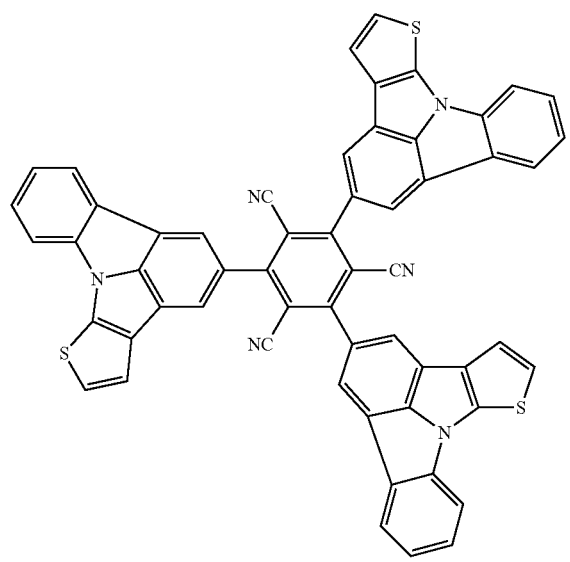
Compound 85
Compound 86
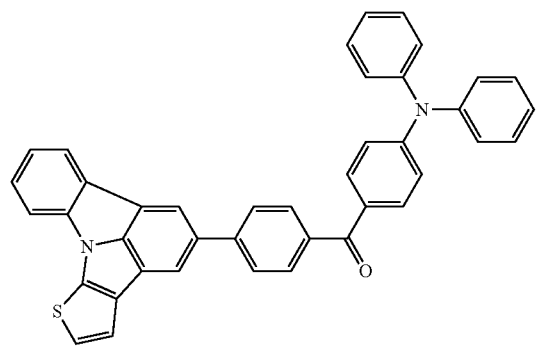
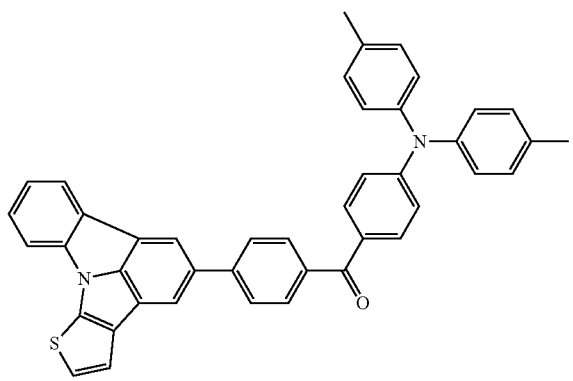

-continued
Compound 87
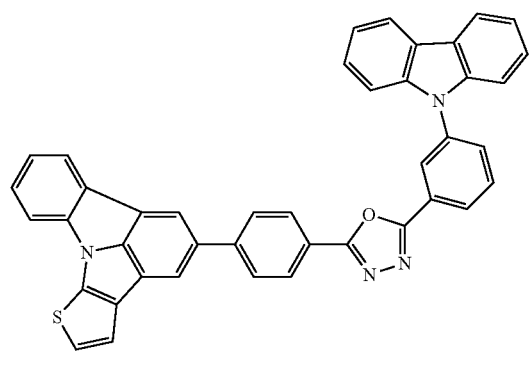
Compound 88
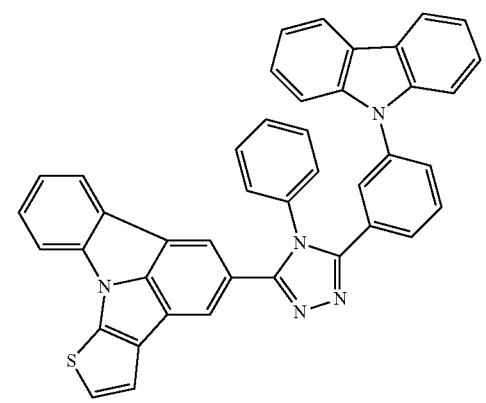
Compound 89
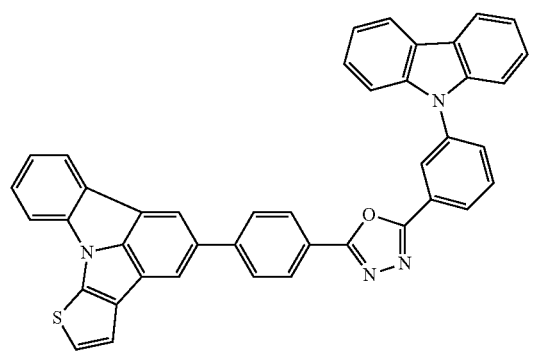
Compound 90
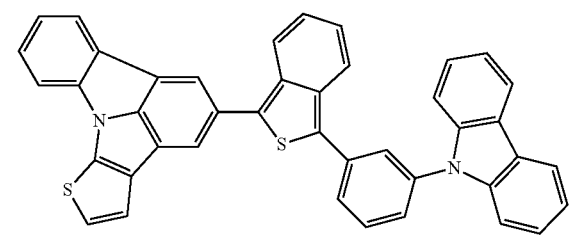
Compound 91
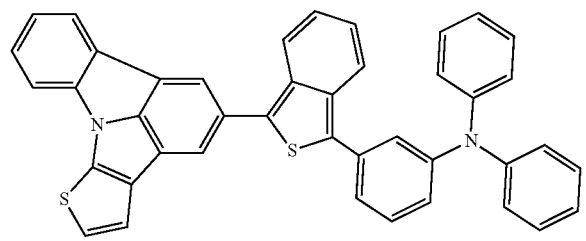
Compound 92
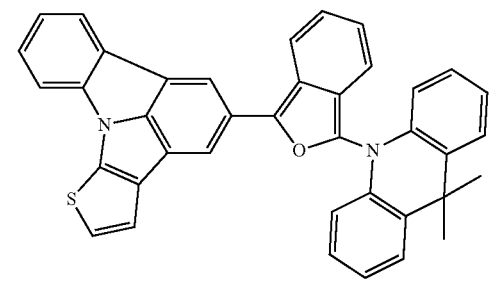
Compound 93
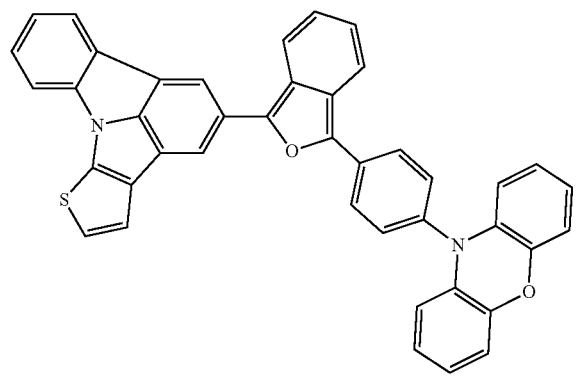
Compound 94
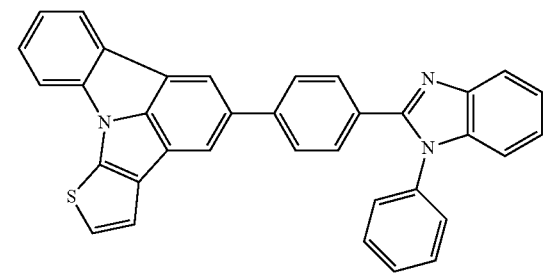

Compound 95
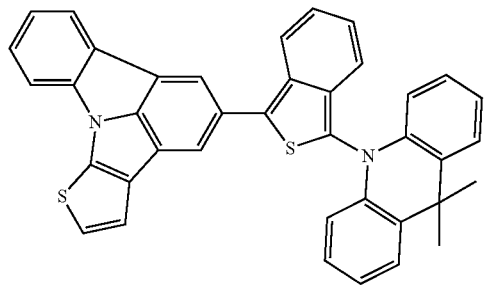
Compound 96
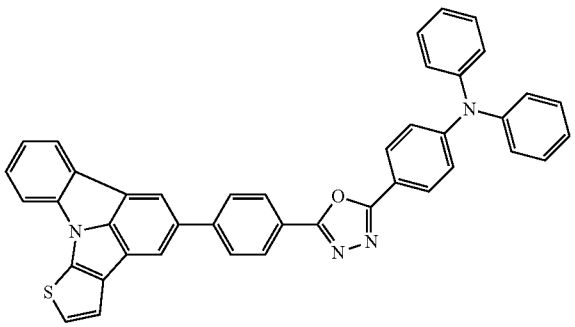
Compound 97
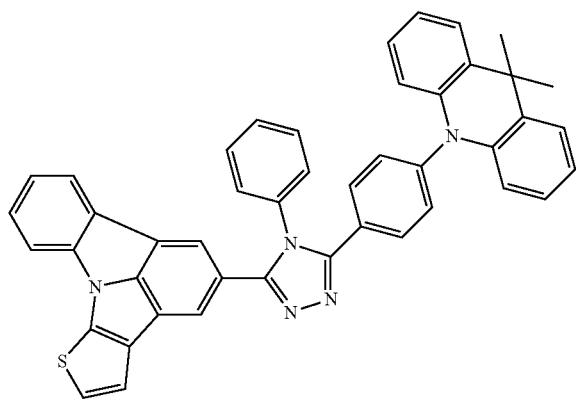
Compound 98
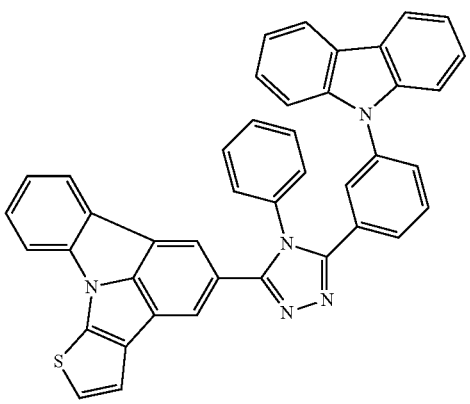
Compound 99
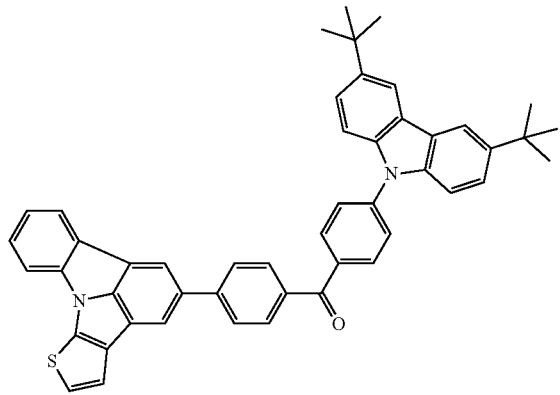
Compound 100
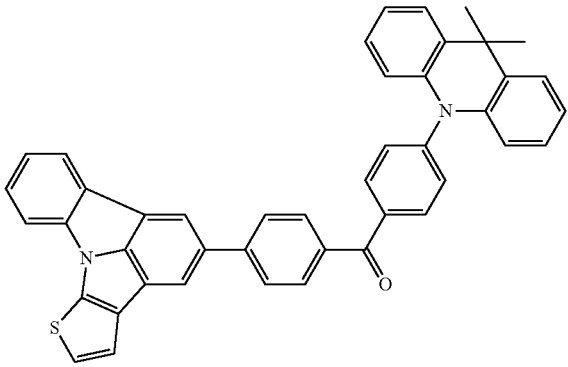
Compound 101
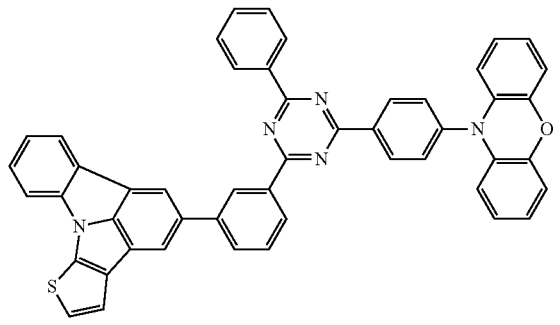
Compound 102
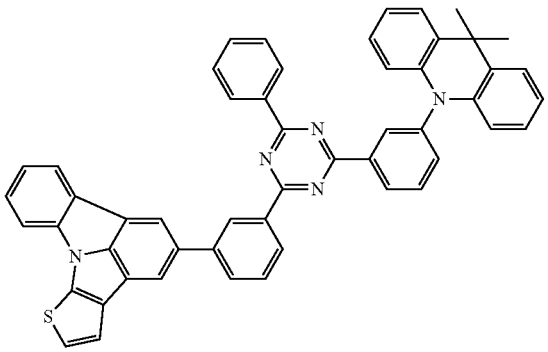

Detailed preparation for the delayed fluorescence material in the present invention could be clarified by exemplary embodiments, but the present invention is not limited to exemplary embodiments. EXAMPLE 1 to EXAMPLE 4 show the preparation for examples of the delayed fluorescence material in the present invention. EXAMPLE 5 show the fabrication of organic EL device and I-V-B, half-life time of organic EL device testing report.

Example 1

Synthesis of TD1

Synthesis of Intermediate A

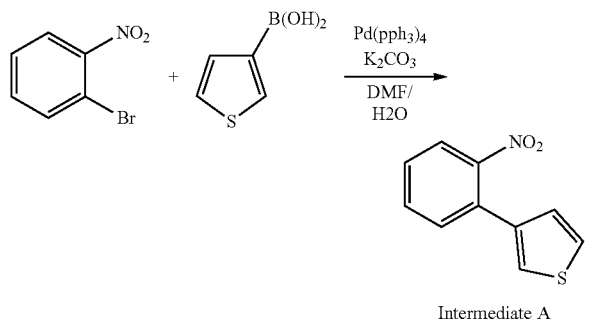

Intermediate A

A mixture of 20 g (99 mmole) of 1-Bromo-2-nitrobenzene, 19 g (148.4 mmole) of 3-thienylboronic acid, 5.7 g (4.93 mmole) of Pd(pph$_3$)$_4$, 27.4 g (198.2 mmole) of K$_2$CO$_3$, 300 ml of DMF, 80 ml of H$_2$O, and placed under nitrogen, and then heated at 80° C. stir for 5 h. After finishing the reaction, the mixture was allowed to cool to room temperature. The solution was extracted with 100 ml of ethyl acetate (3 times) and 300 ml of water. The organic layer was dried with anhydrous magnesium sulfate and the solvent was evaporated under reduced pressure. The residue was purified by column chromatography on silica to give product (19 g, 92.5 mmole, 93.5%) as a yellow liquid.

Synthesis of Intermediate B

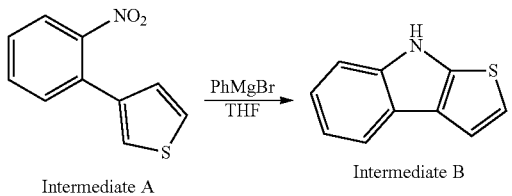 [SMILES: "PhMgBr" ; O=[N+]([O-])c1ccccc1-c1ccsc1 ; c1ccc2c(c1)[nH]c1sccc12 ; "THF"]

PhMgBr (1 M in THF solution) (170 mL, 170.5 mmol) was slowly (0.3 mL/min) added to the mixture of Intermediate A (10 g, 48.7 mmol) and dry THF (300 mL) at 0° C. in 10 minutes. During this time the internal temperature was closely monitored and controlled to remain below 3° C. Then the mixture was stirred at 0° C. for 5 minutes followed by the slow and careful addition of saturated NH4Cl aqueous solution (30 mL). The internal temperature was controlled so that it remained below 5° C. Then 50 mL water was added and the resulting mixture was extracted with ethyl acetate (3×100 mL). The combined organic layers were washed with brine (200 mL), dried over anhydrous Na$_2$SO$_4$, filtered and concentrated in vacuo. The crude product was purified by column chromatography to give product (4 g, 5.77 mmole, 47.6%) as a white solid.

Synthesis of Intermediate C

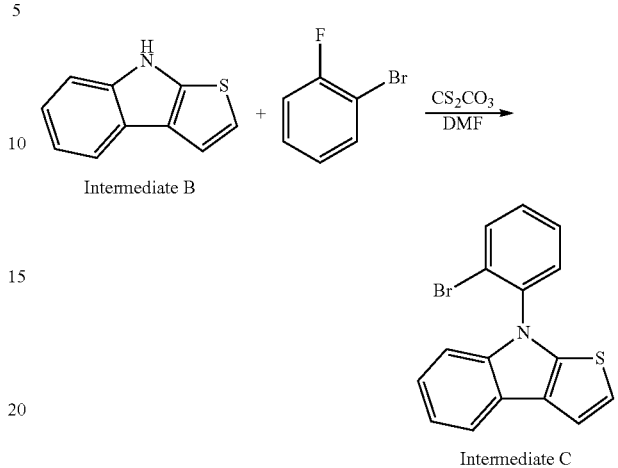

A mixture of 5 g (28.8 mmole) of Intermediate B, 5.6 g (32 mmole) of 1-Bromo-2-fluorobenzene, 14.1 g (43.3 mmole) of Caesium carbonate, 80 ml of DMF and placed under nitrogen, and then heated at 1500° C. stir for 12 h. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (9 g, 27.4 mmole, 94.7%) as a purple solid.

Synthesis of Intermediate D

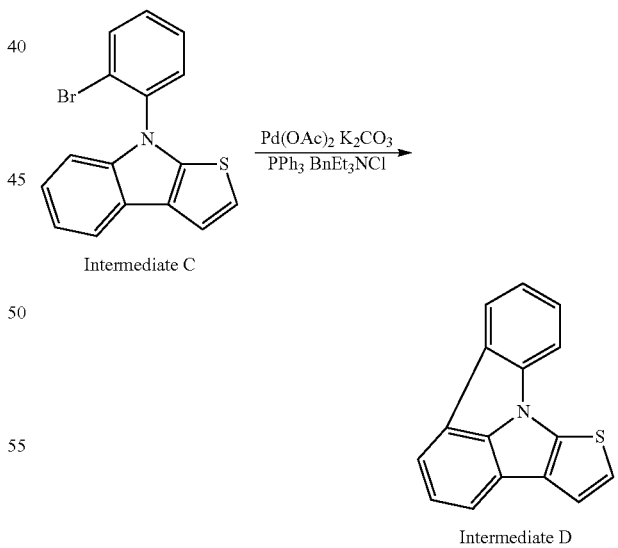

A mixture of 7.5 g (22.8 mmole) of Intermediate C, 15.8 g (114.3 mmole) of K$_2$CO$_3$, 2.4 g (9.15 mmole) of PPh$_3$, 5.2 g (22.8 mmole) of Benzyltriethyl ammonium chloride, 0.78 g (3.47 mmole) of Pd(OAc)$_2$, 150 ml of DMAc and placed under nitrogen, and then heated at 1600° C. stir for 5 h. After finishing the reaction, the mixture was allowed to cool to room temperature. The solution was extracted with 250 ml of DCM and 300 ml of water. The organic layer was dried with anhydrous magnesium sulfate and the solvent was evaporated under reduced pressure. The residue was purified by column chromatography on silica to give product (2.1 g, 8.49 mmole, 37.5%) as a pink solid. 1H NMR (500 MHz, CDCl3): chemical shift 8.08-8.07 (d, 1H), 7.91-7.89 (d, 1H), 7.85-7.84 (d, 1H), 7.69-7.67 (d, 1H), 7.54-7.46 (m, 3H), 7.34-7.31 (m, 1H), 7.06-7.05 (d, 1H), ppm.

Synthesis of Intermediate E

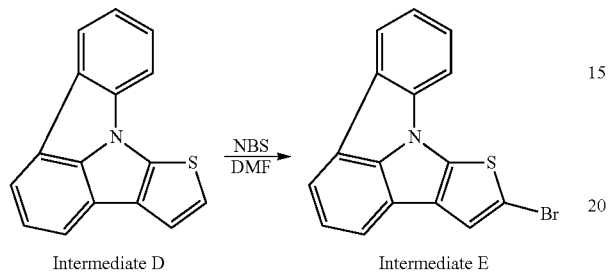

In the N₂ gas purging system, Intermediate D of 2.1 g (8.49 mmole) and N-bromosuccinimide of 1.6 g (8.98 mmole) was put into 50 ml of DMF, where the light was blocked out, and the mixture was stirred for 12 h. After completion of the reaction, the mixture was extracted with 250 ml of DCM and 300 ml of water. The organic layer was dried with anhydrous magnesium sulfate and the solvent was evaporated under reduced pressure. The residue was purified by column chromatography on silica to give product (2.2 g, 6.74 mmole, 79.1%) as a white solid. 1H NMR (500 MHz, CDCl3): chemical shift 8.10-8.08 (d, 1H), 7.93-7.92 (d, 1H), 7.82-7.81 (d, 1H), 7.64-7.63 (d, 1H), 7.56-7.50 (m, 3H), 7.37-7.34 (m, 1H), ppm.

Synthesis of TD1

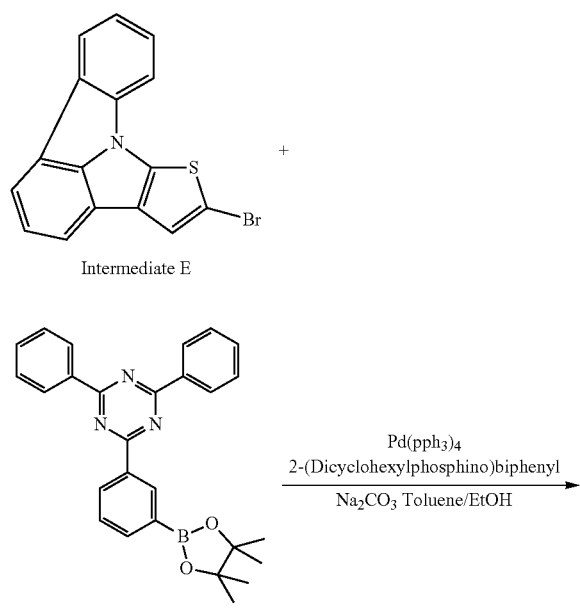

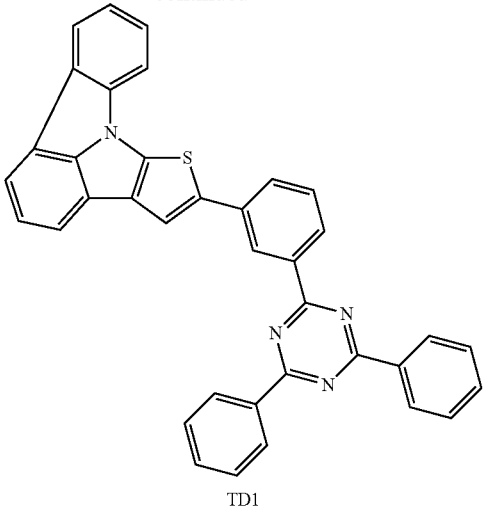

TD1

A mixture of 2 g (6.13 mmole) of Intermediate E, 2.9 g (6.66 mmole) of 2,4-diphenyl-6-(3-(4,4,5,5-tetramethyl-1,3,2-dioxaborolan-2-yl)phenyl)-1,3,5-triazine, 0.14 g (0.12 mmole) of Pd(pph₃)₄, 0.1 g (0.28 mmol) of 2-(dicyclohexylphosphino)biphenyl, 12 ml of 2M Na₂CO₃, 20 ml of EtOH and 60 ml of toluene was degassed and placed under nitrogen, and then heated at 90° C. overnight. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (2.8 g, 5.04 mmole, 82.3%) as a light yellow solid. 1H NMR (500 MHz, CDCl3): chemical shift 9.05 (t, 1H), 8.82-8.80 (q, 4H), 8.69-8.67 (d, 1H), 8.10-8.09 (d, 1H), 7.93-7.88 (m, 4H), 7.76-7.74 (d, 1H), 7.64-7.52 (m, 9H), 7.35 (t, 1H), ppm; MS m/z: calcd for C₃₇H₂₂N₄S, 554.157; found 554.153.

Example 2

Synthesis of TD2

Synthesis of TD2

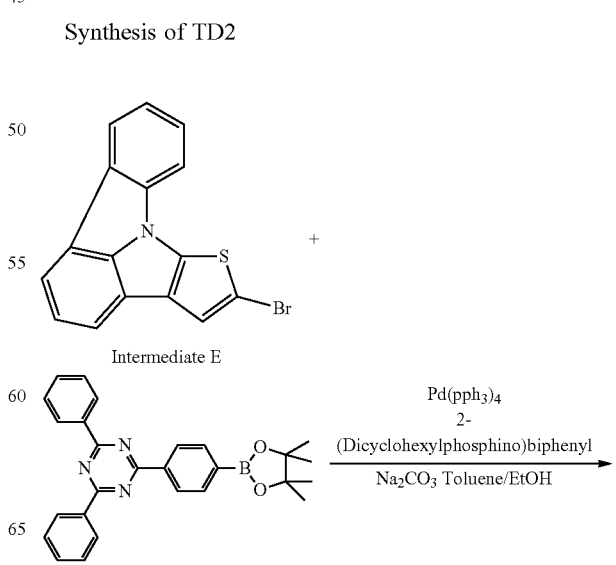

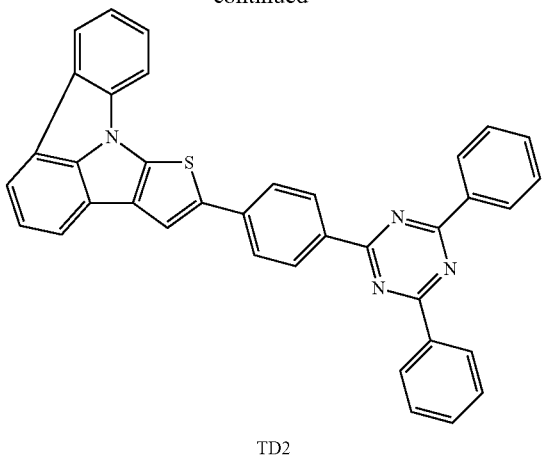

TD2

A mixture of 2.2 g (6.74 mmole) of Intermediate E, 10.7 g (7.35 mmole) of 2,4-diphenyl-6-(4-(4,4,5,5-tetramethyl-1,3,2-dioxaborolan-2-yl)phenyl)-1,3,5-triazine, 0.16 g (0.13 mmole) of Pd(pph$_3$)$_4$, 0.1 g (0.28 mmol) of 2-(dicyclohexylphosphino)biphenyl, 15 ml of 2M Na$_2$CO$_3$, 30 ml of EtOH and 90 ml of toluene was degassed and placed under nitrogen, and then heated at 90° C. overnight. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (3 g, 5.4 mmole, 80.1%) as a light yellow solid. 1H NMR (500 MHz, CDCl3): chemical shift 8.83-8.81 (d, 2H), 8.79-8.78 (d, 4H), 8.11-8.10 (d, 1H), 7.94-7.86 (m, 4H), 7.75-7.74 (d, 1H), 7.62-7.53 (m, 9H), 7.36 (t, 1H), ppm; MS m/z: calcd for C$_{37}$H$_{22}$N$_4$S, 554.157; found 554.155.

Example 3

Synthesis of TD3

Synthesis of Intermediate F

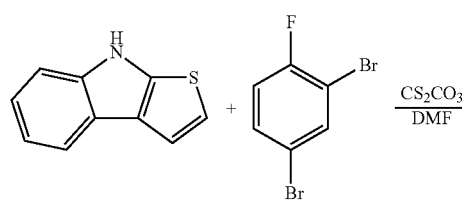

A mixture of 4 g (23.1 mmole) of Intermediate B, 6.4 g (25.4 mmole) of 2,4-dibromo-1-fluorobenzene, 11.3 g (34.6 mmole) of Caesium carbonate, 80 ml of DMF and placed under nitrogen, and then heated at 150° C. stir for 12 h. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (7.8 g, 19.2 mmole, 83.1%) as a white solid.

Synthesis of Intermediate G

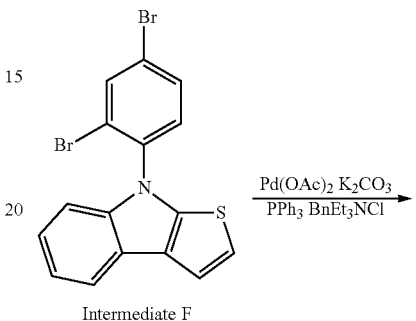

Intermediate F

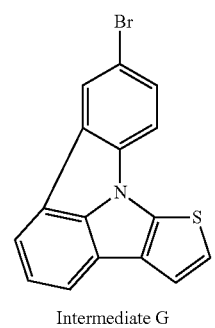

Intermediate G

A mixture of 7.5 g (18.4 mmole) of Intermediate F, 12.7 g (92.1 mmole) of K$_2$CO$_3$, 1.9 g (7.37 mmole) of PPh$_3$, 4 g (18.4 mmole) of Benzyltriethylammonium chloride, 0.62 g (2.76 mmole) of Pd(OAc)$_2$, 150 ml of DMAc and placed under nitrogen, and then heated at 160° C. stir for 5 h. After finishing the reaction, the mixture was allowed to cool to room temperature. The solution was extracted with 250 ml of DCM and 300 ml of water. The organic layer was dried with anhydrous magnesium sulfate and the solvent was evaporated under reduced pressure. The residue was purified by column chromatography on silica to give product (1.9 g, 5.82 mmole, 32.3%) as a pink solid. 1H NMR (500 MHz, CDCl3): chemical shift 8.11-8.10 (d, 1H), 8.04 (s, 1H), 7.65-7.63 (d, 1H), 7.53-7.51 (d, 1H), 7.46-7.44 (d, 1H), 7.31-7.27 (m, 2H), 6.98-6.97 (d, 1H), ppm.

Synthesis of TD3

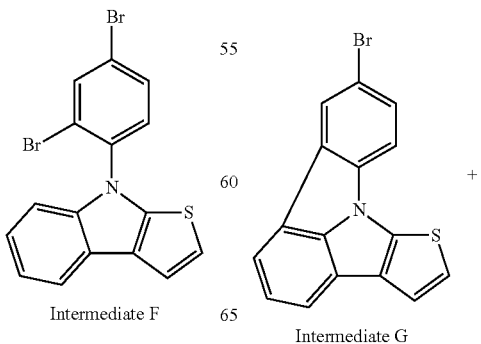

Intermediate F      Intermediate G

-continued

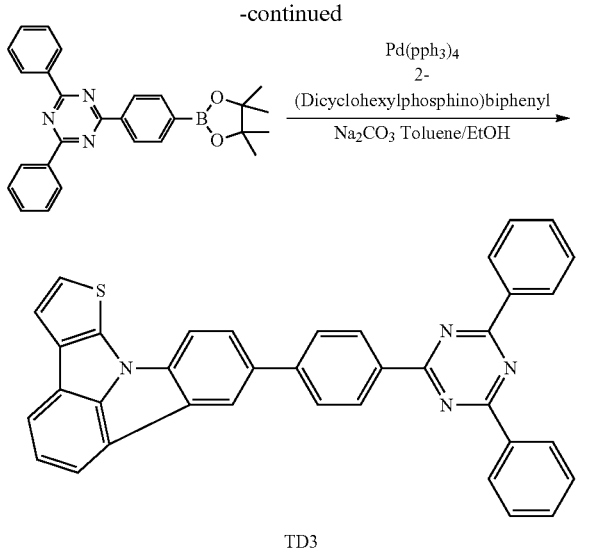

TD3

A mixture of 1.9 g (5.82 mmole) of Intermediate G, 10.7 g (6.40 mmole) of 2,4-diphenyl-6-(4-(4,4,5,5-tetramethyl-1,3,2-dioxaborolan-2-yl)phenyl)-1,3,5-triazine, 0.13 g (0.12 mmole) of $Pd(pph_3)_4$, 0.1 g (0.12 mmol) of 2-(dicyclohexylphosphino)biphenyl, 15 ml of 2M $Na_2CO_3$, 30 ml of EtOH and 90 ml of toluene was degassed and placed under nitrogen, and then heated at 90° C. overnight. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (2.3 g, 4.1 mmole, 73.1%) as a yellow solid. 1H NMR (500 MHz, CDCl3): chemical shift 8.62-8.58 (m, 4H), 8.54-8.52 (d, 1H), 8.41-8.39 (m, 3H), 8.31 (s, 1H), 7.83-7.72 (m, 2H), 7.69-7.60 (m, 9H), 7.41-7.39 (d, 1H) 7.13-7.11 (d, 1H), ppm; MS m/z: calcd for $C_{37}H_{22}N_4S$, 554.157; found 554.159.

Example 4

Synthesis of TD4

Synthesis of Intermediate H

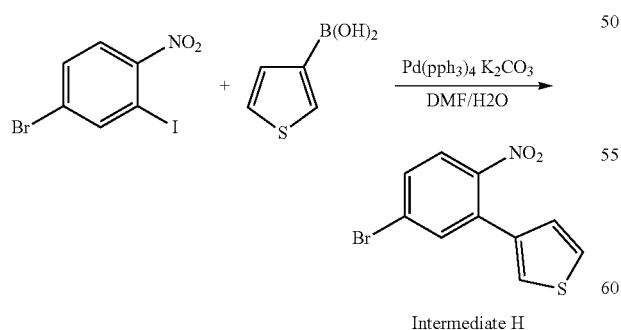

Intermediate H

A mixture of 15 g (45.7 mmole) of 4-bromo-2-iodo-1-nitrobenzene, 8.8 g (68.6 mmole) of 3-thienylboronic acid, 2.6 g (2.3 mmole) of $Pd(pph_3)_4$, 12.6 g (91.4 mmole) of $K_2CO_3$, 300 ml of DMF, 80 ml of $H_2O$, and placed under nitrogen, and then heated at 80° C. stir for 5 h. After finishing the reaction, the mixture was allowed to cool to room temperature. The solution was extracted with 100 ml of ethyl acetate (3 times) and 300 ml of water. The organic layer was dried with anhydrous magnesium sulfate and the solvent was evaporated under reduced pressure. The residue was purified by column chromatography on silica to give product (11.7 g, 41.2 mmole, 90.1%) as a yellow liquid.

Synthesis of Intermediate I

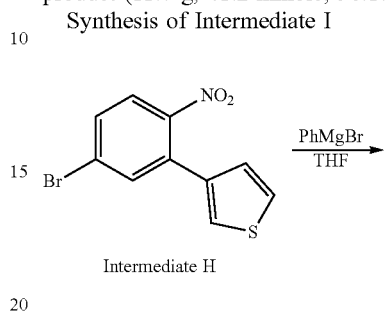

Intermediate H

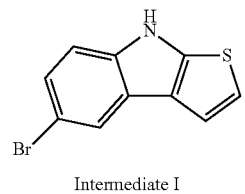

Intermediate I

PhMgBr (1 M in THF solution) (123.2 mL, 123.2 mmol) was slowly (0.3 mL/min) added to the mixture of Intermediate H (10 g, 35.2 mmol) and dry THF (300 mL) at 0° C. in 10 minutes. During this time the internal temperature was closely monitored and controlled to remain below 3° C. Then the mixture was stirred at 0° C. for 5 minutes followed by the slow and careful addition of saturated NH4Cl aqueous solution (30 mL). The internal temperature was controlled so that it remained below 5° C. Then 50 mL water was added and the resulting mixture was extracted with ethyl acetate (3×100 mL). The combined organic layers were washed with brine (200 mL), dried over anhydrous $Na_2SO_4$, filtered and concentrated in vacuo. The crude product was purified by column chromatography to give product (4.1 g, 16.3 mmole, 46.3%) as a white solid.

Synthesis of Intermediate J

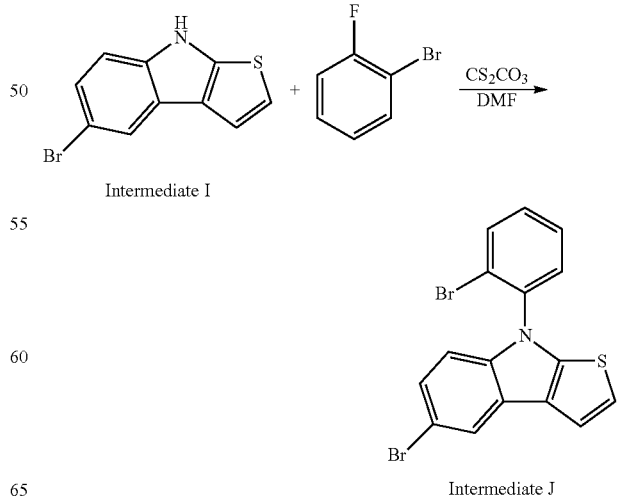

Intermediate J

A mixture of 4 g (15.8 mmole) of Intel mediate I, 3 g (17.1 mmole) of 1-Bromo-2-fluorobenzene, 3.2 g (23.8 mmole) of Casium carbonate, 80 ml of DMF and placed under nitrogen, and then heated at 150° C. stir for 12 h. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (6 g, 14.8 mmole, 93.2%) as a purple solid.

Synthesis of Intermediate K

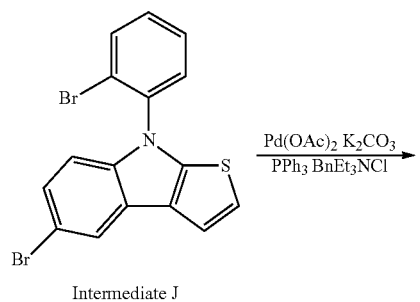

Intermediate J

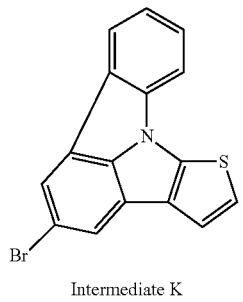

Intermediate K

A mixture of 6 g (14.7 mmole) of Intermediate J, 10.2 g (73.8 mmole) of $K_2CO_3$, 1.5 g (5.89 mmole) of $PPh_3$, 3.3 g (14.7 mmole) of Benzyltriethylammonium chloride, 0.5 g (2.21 mmole) of $Pd(OAc)_2$, 150 ml of DMAc and placed under nitrogen, and then heated at 160° C. stir for 5 h. After finishing the reaction, the mixture was allowed to cool to room temperature. The solution was extracted with 250 ml of DCM and 300 ml of water. The organic layer was dried with anhydrous magnesium sulfate and the solvent was evaporated under reduced pressure. The residue was purified by column chromatography on silica to give product (1.9 g, 5.9 mmole, 40.1%) as a pink solid. 1H NMR (500 MHz, CDCl3): chemical shift 8.10-8.09 (d, 1H), 8.08 (s, 1H), 7.66-7.60 (m, 1H), 7.52 (s, 1H), 7.48-7.45 (m, 1H), 7.32-7.29 (m, 1H), 7.21-7.20 (d, 1H), 6.92-6.91 (d, 1H) ppm.

Synthesis of TD4

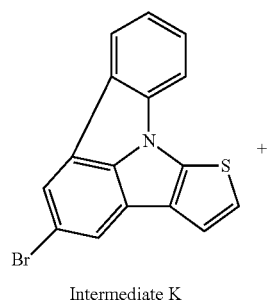

Intermediate K

+

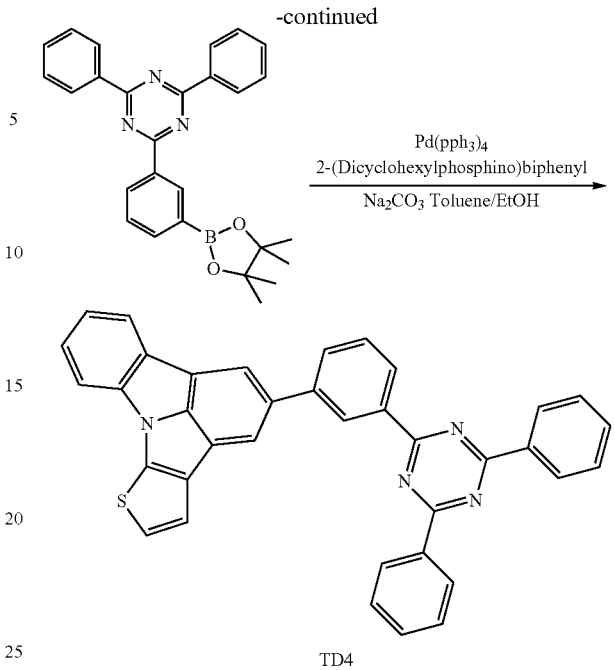

TD4

A mixture of 2 g (6.13 mmole) of Intermediate E, 2.9 g (6.66 mmole) of 2,4-diphenyl-6-(3-(4,4,5,5-tetramethyl-1,3,2-dioxaborolan-2-yl)phenyl)-1,3,5-triazine, 0.14 g (0.12 mmole) of $Pd(pph_3)_4$, 0.1 g (0.28 mmol) of 2-(dicyclohexylphosphino)biphenyl, 12 ml of 2M $Na_2CO_3$, 20 ml of EtOH and 60 ml of toluene was degassed and placed under nitrogen, and then heated at 90° C. overnight. After finishing the reaction, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (2.9 g, 5.22 mmole, 85.1%) as a light yellow solid. 1H NMR (500 MHz, CDCl3): chemical shift 8.30-8.26 (m, 5H), 8.12-8.10 (d, 1H), 7.74 (s, 1H), 7.70 (s, 1H), 7.68-7.36 (m, 10H), 7.32-7.29 (m, 2H), 7.23-7.22 (d, 1H), 6.96-6.95 (d, 1H) ppm; MS m/z: calcd for $C_{37}H_{22}N_4S$, 554.157; found 554.159.

Measurement Method of Delayed Fluorescence Compound for Photophysical Properties Photophysical Characterization: Synthesized compounds were subject to purification by temperature-gradient sublimation in high vacuum before use in subsequent studies. Thin films for photophysical characterization were prepared by thermal evaporation on quartz substrates at 1-2 A/sec in a vacuum chamber with a base pressure of <10−6 torr. Absorption spectra of the resulting thin films and dilute solutions were characterized by a UV-vis-NIR spectrophotometer (UV-1650 PC, Shimadzu). Photoluminescence (PL) spectra, photoluminescence quantum yields (PLQYs), and phosphorescence spectra were characterized by a spectrofluorimeter (FluoroMax-P, Horiba Jobin Yvon Inc.). PLQYs of thin films or dilute solutions were determined using this spectrofluorimeter equipped with a calibrated integrating sphere. The selected monochromatic excitation light was used to excite samples placed in the calibrated integrating sphere. By comparing the spectral intensities of the monochromatic excitation light and the PL emission, the PL quantum yields were determined. Phosphorescence spectra of thin films or dilute solutions were conducted at 77K (the liquid nitrogen temperature) by the spectrofluorimeter equipped with a microsecond flash lamp as the pulsed excitation source. A 10-ms delay time was inserted between the pulsed excitation and the collection of the emission spectrum. Time-resolved PL (PL decay curves) was measured by monitoring the decay of the intensity at the PL peak wavelength using the time-correlated single-photon counting technique with a fluorescence lifetime system (Fluoro-Cube, Horiba Jobin Yvon Inc.) and nanosecond pulsed light excitation from a UV light-emitting diode (300 nm). The samples were placed in a vacuum cryostat chamber with the temperature control. The PL spectra of the prompt and delayed components were collected using this same fluorescence lifetime system with a 200-ns delay time and a 10-us delay time between the pulsed excitation and the collection of the emission spectrum. Electrochemical Characterization: Cyclic voltammetry by a CHI 619B potentiostat was used to measure oxidation/reduction potentials. The oxidation potential was determined by cyclic voltammetry (CV) using 0.1M n-Bu4NPF6 (TBAPF6) in CH2Cl2 as a supporting electrolyte and a scan rate of 100 mV s−1. The reduction potential was recorded using 0.1M n-Bu4NClO4 (TBAP) in DMF as a supporting electrolyte and a scan rate of 100 mV s−1. A standard 3-electrode cell comprising silver/silver chloride (Ag/AgCl), a platinum wire and a glassy carbon electrode as the reference, counter, and working electrodes, respectively, were used. All potentials were recorded versus Ag/AgCl (saturated) as a reference electrode. Oxidation of the ferrocene/ferrocenium (Fc/Fc+) redox couple in CH2Cl2/TBAPF6 occurs at E'o=+0.47V and reduction of the ferrocene/ferrocenium (Fc/Fc+) redox couple in DMF/TBAP occurs at E"o=+0.51 V vs. Ag/AgCl (saturated) collecting the total emission fluxes with a calibrated integrating-sphere measurement system.

Figure 2:
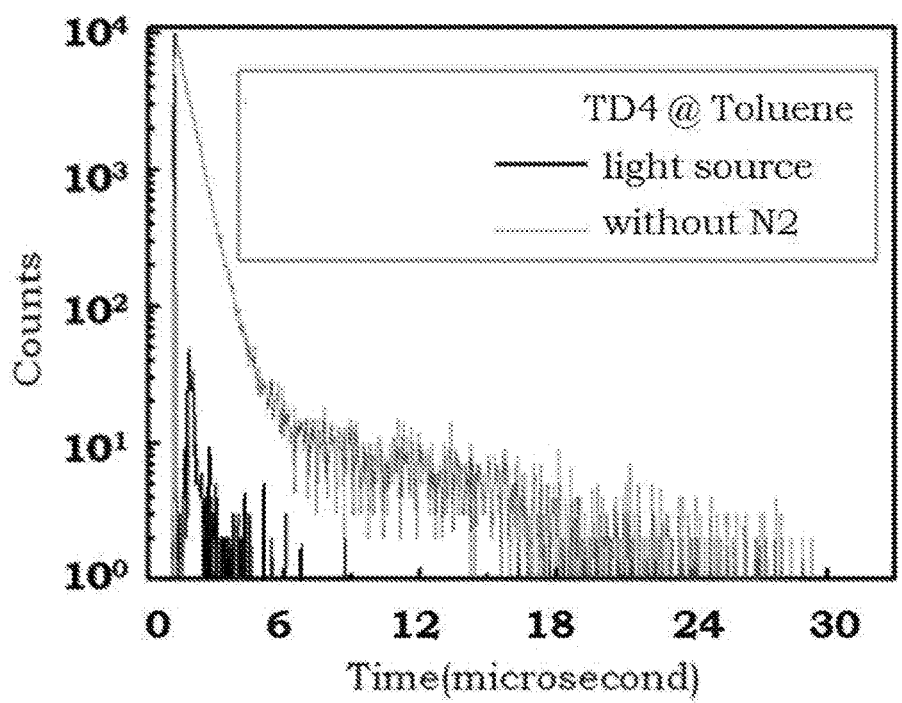
FIG. 2 show the transient decay cure of compound TD4 for the delayed fluorescent property.
Figure 2:
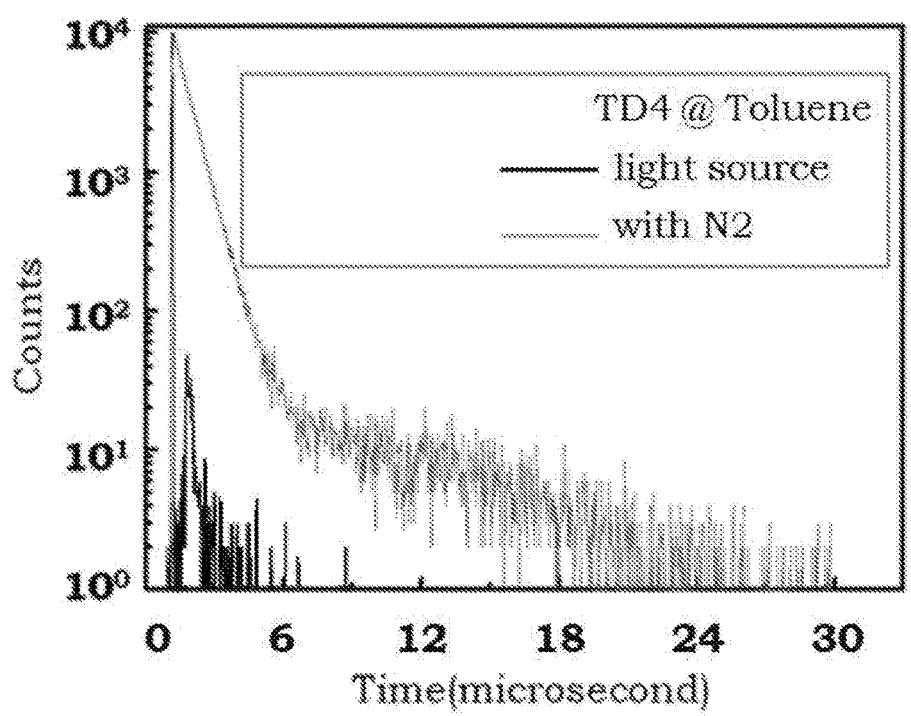

FIG. 2 and FIG. 3 show the measurement of the transient decay curve of Toluene solution had displayed delayed fluorescence for C4 and Compared compound. FIG. 4 and FIG. 5 show the measurement of the photoluminescence light emission spectrum of C4 and Compared compound.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer, H1 used as phosphorescent host and H2 used as delayed fluorescence host for comparable or standard with the present invention. The chemical structure shown below:

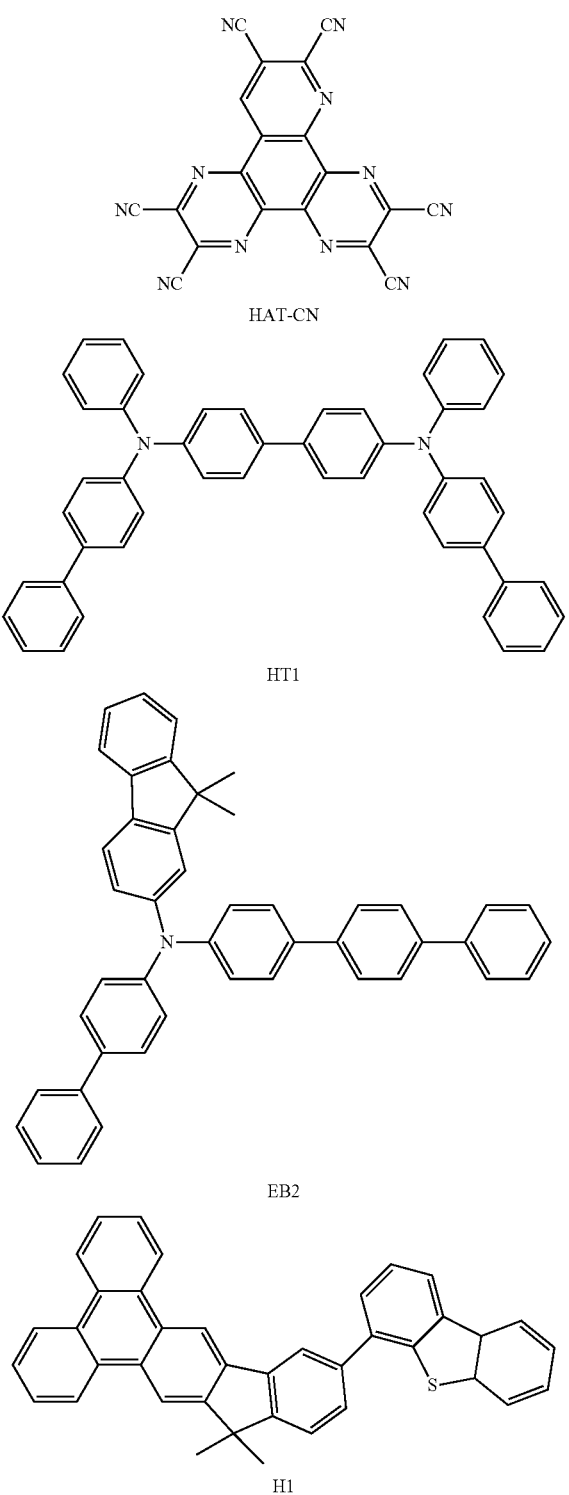

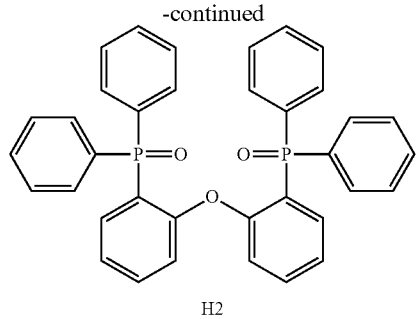

H2

The following delayed fluorescence Examples prepared in the present invention can be verified and used as delayed fluorescence dopant, phosphorescent host by organic EL device.

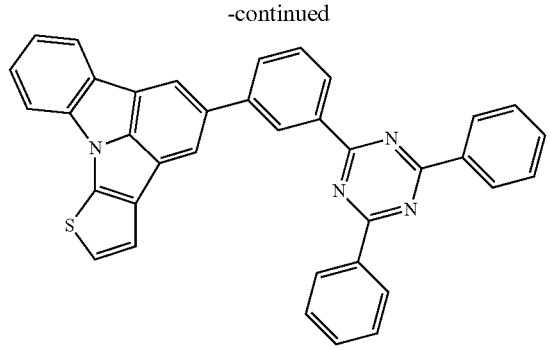

TD4

Organic iridium complexes are widely used as phosphorescent dopant for light emitting layer, Ir(ppy)$_3$ are widely used for phosphorescent green dopant of light emitting layer for organic EL device.

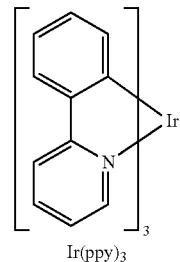

Ir(ppy)$_3$

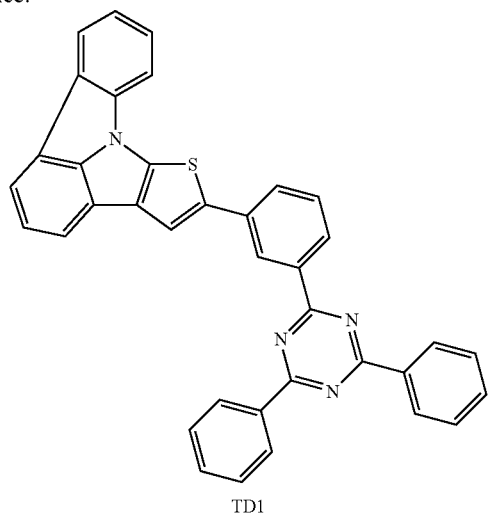

TD1

2,2',2"-(1,3,5-Benzinetriyl)-tris(1-phenyl-1-H-benzimidazole) (TPBi) and HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

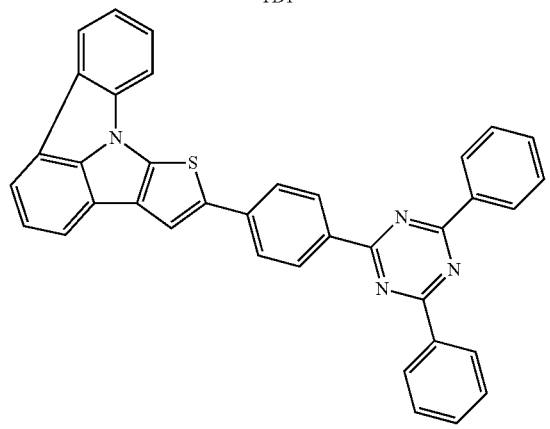

TD2

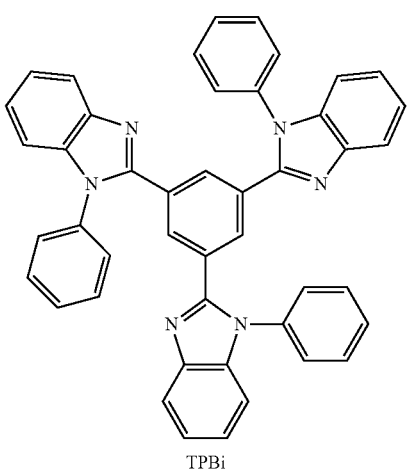

TPBi

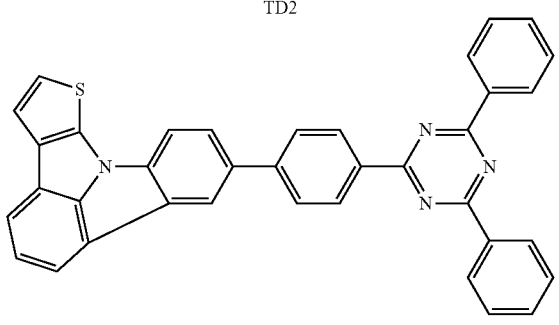

TD3

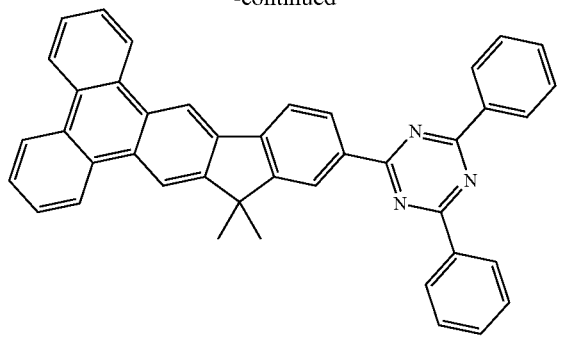

ET2

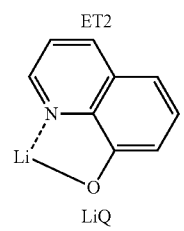

LiQ

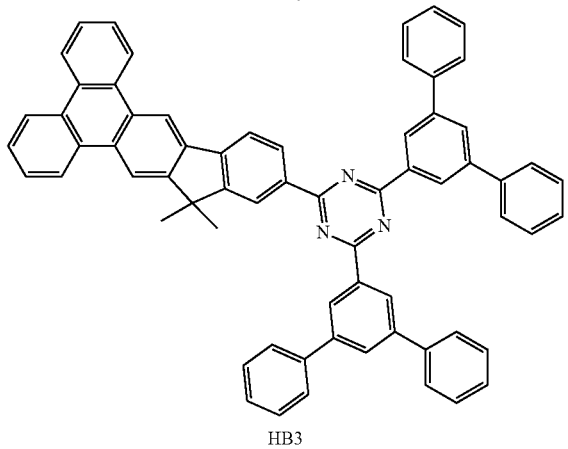

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the above mentioned general method, organic EL device having the following device structure was produced (See FIG. 1). Device: ITO/ HAT-CN (20 nm)/HT1 (110 nm)/EB2 (5 nm)/Host+ 10%~20% dopant (30 nm)/HBM (10 nm)/ETM doped 40% LiQ (35 nm)/LiQ (1 nm)/Al (160 nm). The I-V-B (at 1000 nits) of organic EL device testing report as Table 1.

TABLE 1

| Dopant(%) | Host or cohost(1:1) | HBM | ETM | Voltage (V) | Efficiency (cd/A) | Device color |
|---|---|---|---|---|---|---|
| TD1(15%) | H2 | TPBi | ET2 | 8.0 | 6 | Blue |
| TD2(18%) | H2 | TPBi | ET2 | 7.5 | 5 | Blue |
| TD3(15%) | H2 | TPBi | ET2 | 6.0 | 14 | Blue |
| TD4(18%) | H2 | TPBi | ET2 | 5.5 | 13 | Blue |
| Ir(ppy)$_3$(10%) | TD1 | HB3 | ET2 | 4.2 | 24 | Green |
| Ir(ppy)$_3$(10%) | TD3 | HB3 | ET2 | 4.8 | 28 | Green |
| Ir(ppy)$_3$(10%) | TD2 + H1 | HB3 | ET2 | 5.0 | 40 | Green |
| Ir(ppy)$_3$(10%) | TD4 + H1 | HB3 | ET2 | 5.0 | 43 | Green |

In the above preferred embodiments for organic EL device testing report (see Table 1), we show that the delayed fluorescence compound with a general formula (1) used as light emitting host of emitting layer, or an a delayed fluorescence material of emitting layer for organic EL device in the present invention display good performance.

To sum up, the present invention discloses an delayed fluorescence material which can be used as phosphorescent light emitting host of emitting layer or a delayed fluorescence material of emitting layer for organic EL device The mentioned delayed fluorescence compound formula (1) represented by the following formula (1)

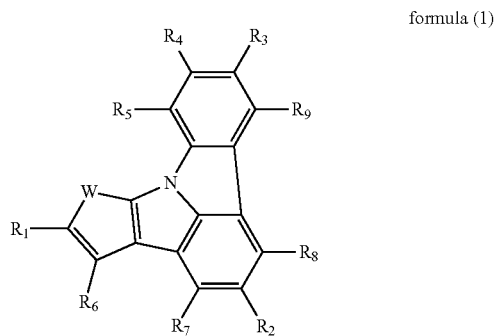

formula (1)

wherein W independently represents an oxygen atom, a sulfur atom and a selenium atom; $R_1$, $R_2$ and $R_3$ are independently selected from the group consisting of a hydrogen atom, a deuterium atom, a halide, formula (2) or formula (3):

formula (2)

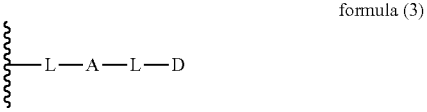

formula (3)

D is an electron donor represented from formula (1), a substituted or unsubstituted carbazolyl group, a substituted or unsubstituted biscarbazolyl group, a substituted or unsubstituted dihydroacridine group, a substituted or unsubstituted phenoxazine group and a substituted or unsubstituted diarylamine group; A is an electron acceptor selected from the group consisting of the following formulas:

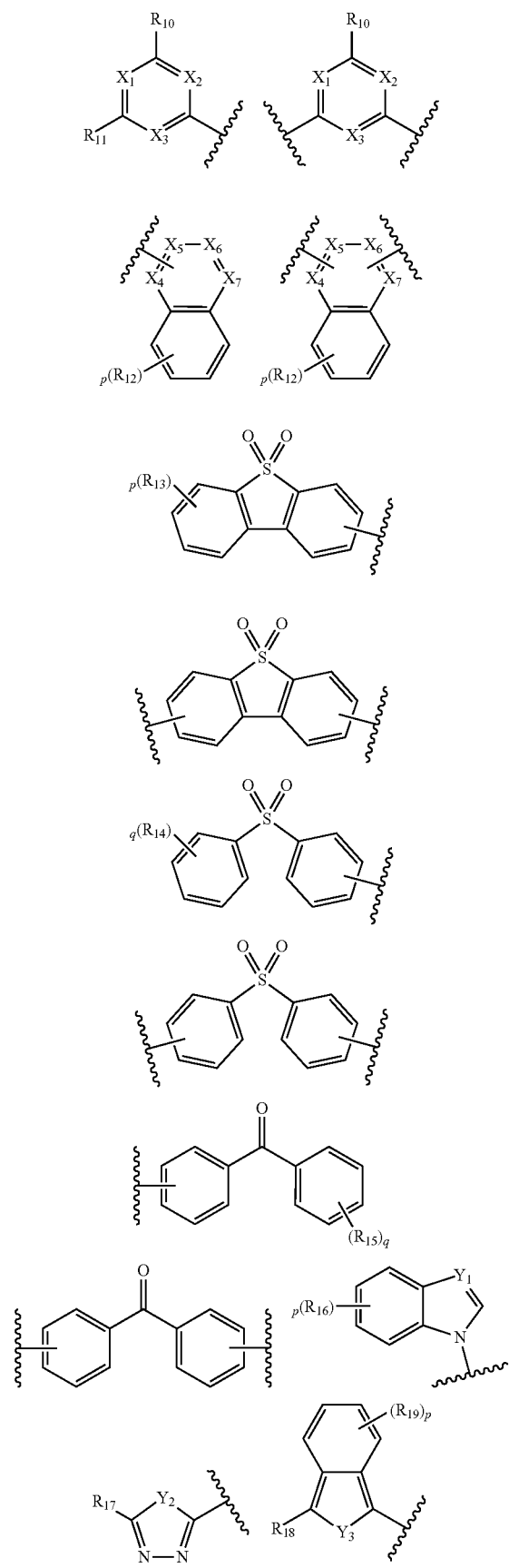

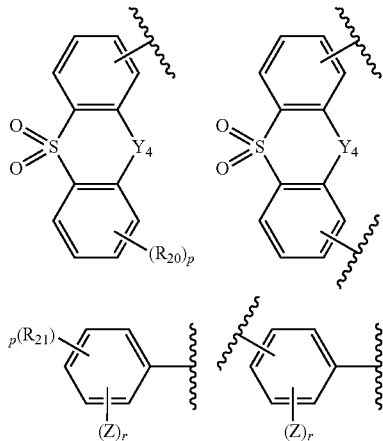

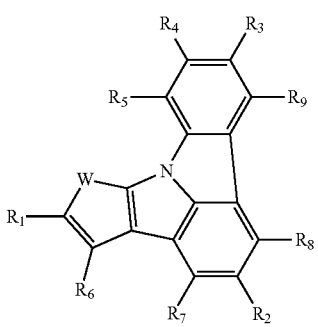

L represents a single bond or a substituted or unsubstituted divalent arylene group having 6 to 30 ring carbon atoms, p represents an integer of 0 to 4, q represents an integer of 0 to 5, r represents an integer of 1 to 4, $Y_1$ to $Y_4$ is a divalent bridge selected from the atom or group consisting from O, S, $C(R_{22})(R_{23})$, $NR_{24}$, and $Si(R_{25})(R_{26})$, $X_1$ to $X_7$ represent a nitrogen atom or $C(R_s)$, and each $R_s$ represents a hydrogen, a phenyl, a substituted or unsubstituted alkyl group having 1 to 30 carbon atoms, or a substituted or unsubstituted aryl group having 6 to 30 carbon atoms, Z represents a cyano group or a fluorine atom, $R_4$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A delayed fluorescence material with a general formula (1) as follows:

formula (1)

wherein W independently represents an oxygen atom, a sulfur atom or a selenium atom; $R_1$, $R_2$ and $R_3$ are independently selected from the group consisting of a hydrogen atom, a deuterium atom, a halide, formula (2) or formula (3):

formula (2)
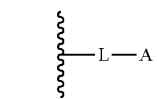

formula (3)
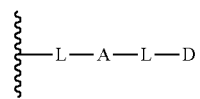

D is an electron donor represented from formula (1), a substituted or unsubstituted carbazolyl group, a substituted or unsubstituted biscarbazolyl group, a substituted or unsubstituted dihydroacridine group, a substituted or unsubstituted phenoxazine group and a substituted or unsubstituted diarylamine group; A is an electron acceptor selected from the group consisting of the following formulas:

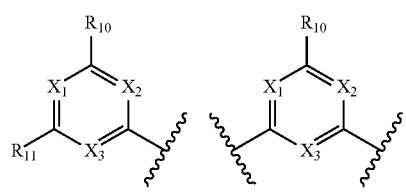

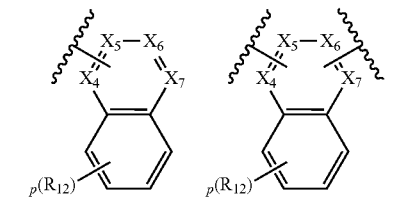

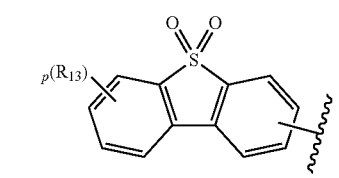

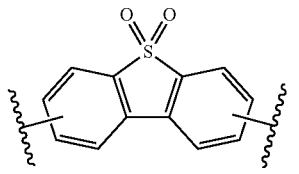

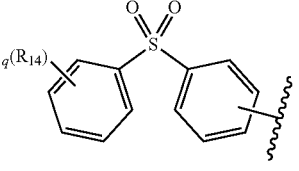

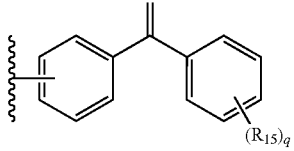

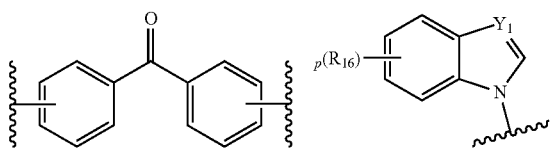

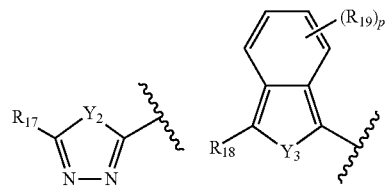

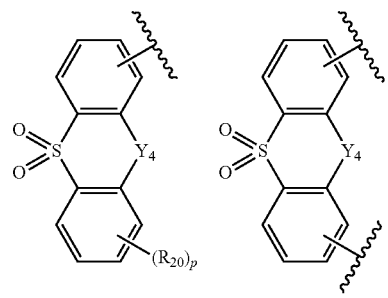

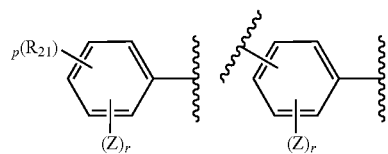

L represents a single bond or a substituted or unsubstituted divalent arylene group having 6 to 30 ring carbon atoms, p represents an integer of 0 to 4, q represents an integer of 0 to 5, r represents an integer of 1 to 4, $Y_1$ to $Y_4$ is a divalent bridge selected from the atom or group consisting from O, S, $C(R_{22})(R_{23})$, $NR_{24}$, and $Si(R_{25})(R_{26})$, $X_1$ to $X_7$ represent a nitrogen atom or $C(R_s)$, and each $R_s$ represents a hydrogen, a phenyl, a substituted or unsubstituted alkyl group having 1 to 30 carbon atoms, or a substituted or unsubstituted aryl group having 6 to 30 carbon atoms, Z represents a cyano group or a fluorine atom, $R_4$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

2. The delayed fluorescence material according to claim 1, wherein the delayed fluorescence material formula (1) is represented by the following formula (4) to formula (12)

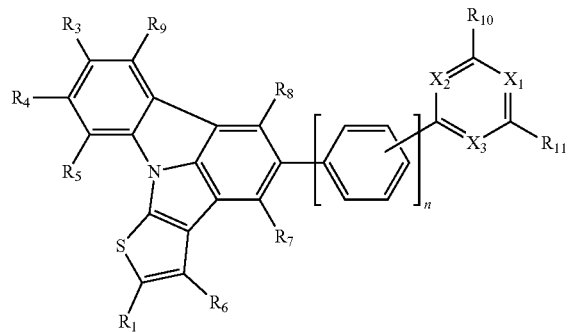
formula (4)
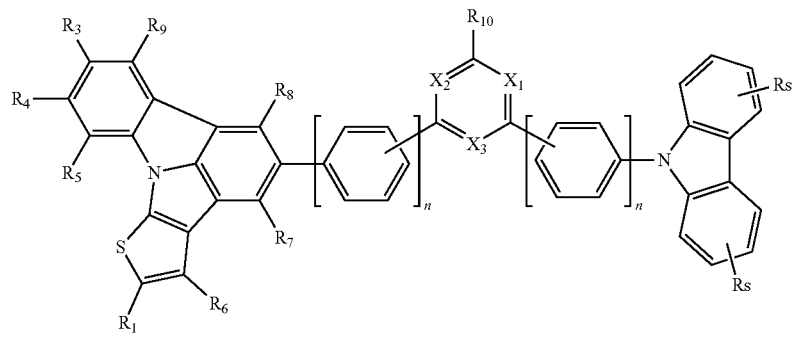
formula (5)
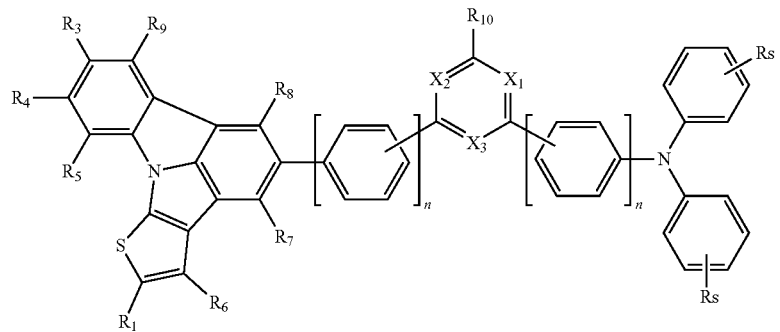
formula (6)
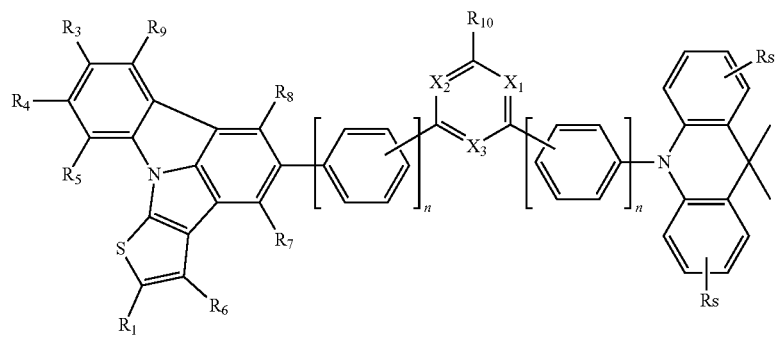
formula (7)

-continued
formula (8)
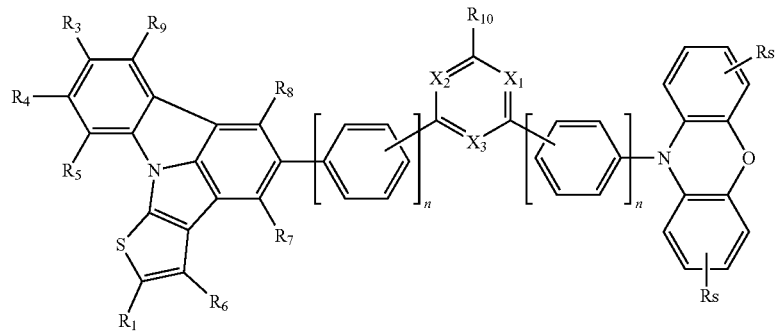
formula (9)
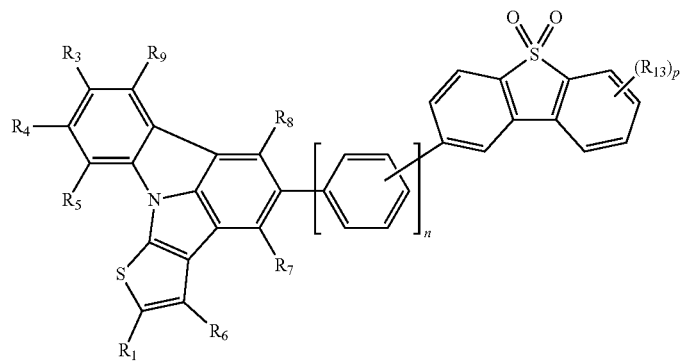
formula (10)
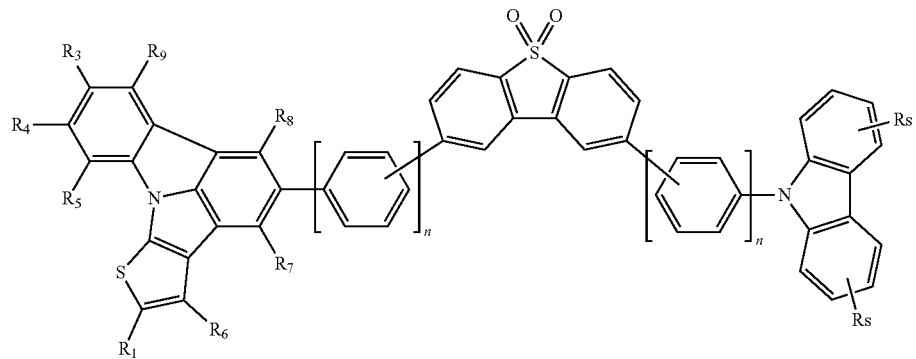
formula (11)
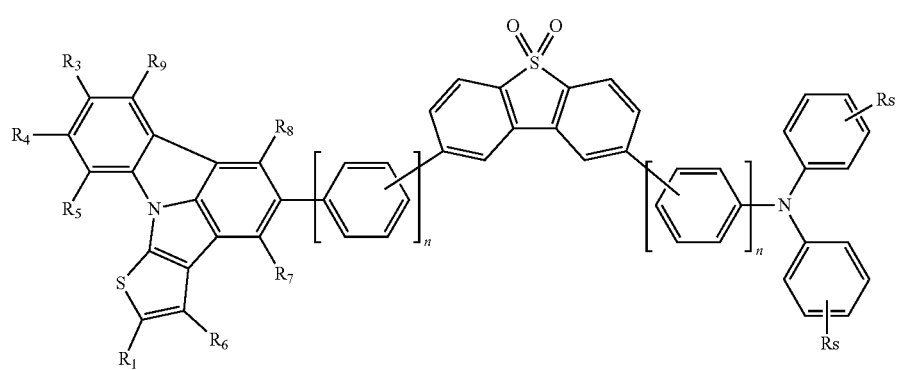

-continued formula (12)

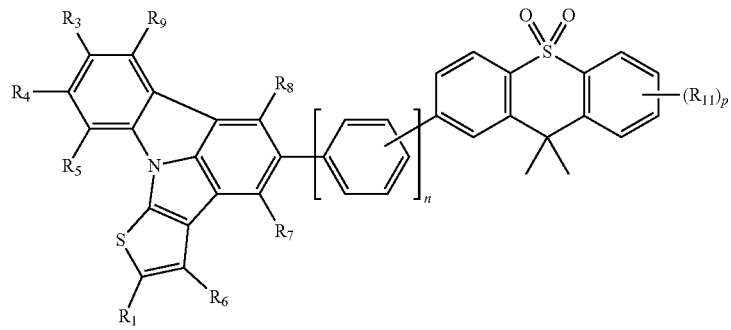

formula (13)

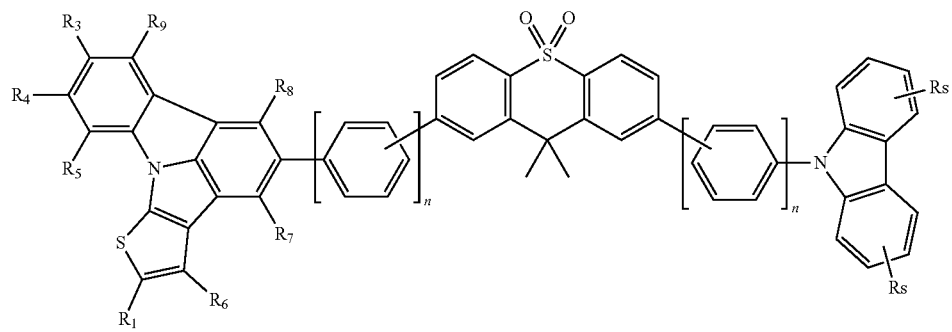

formula (14)

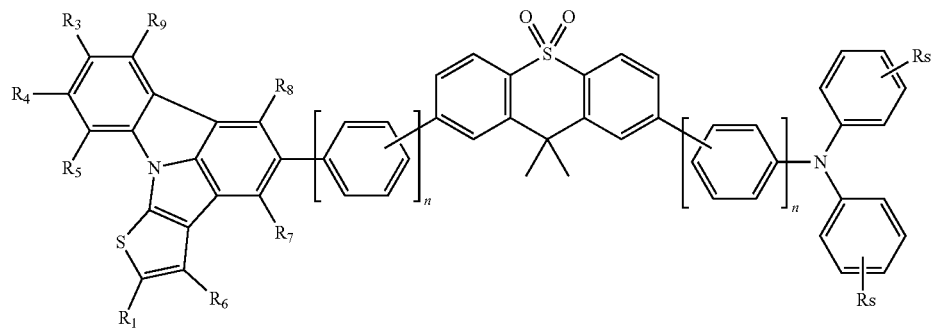

formula (15)

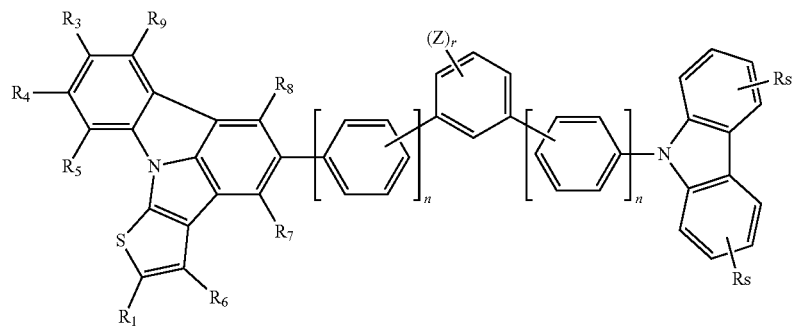

n represents an integer of 0 or 1, p represents an integer of 0 to 4, q represents an integer of 0 to 5, r represents an integer of 1 to 4, $X_1$ to $X_3$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms, Z represents a cyano group or a fluorine atom, $R_1$ to $R_{13}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

3. The delayed fluorescence material according to claim 1, wherein the delayed fluorescence material formula (1) is represented by one of the following compound 1 to compound 102:

Compound 1
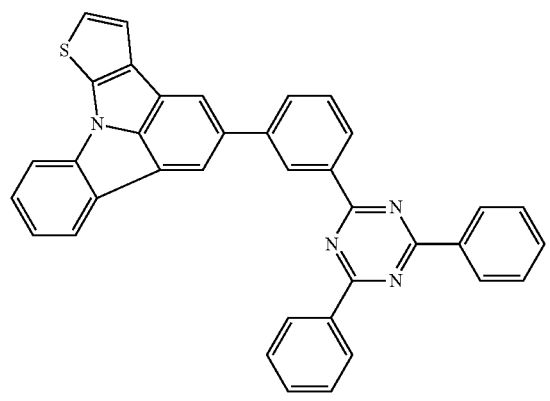
Compound 2
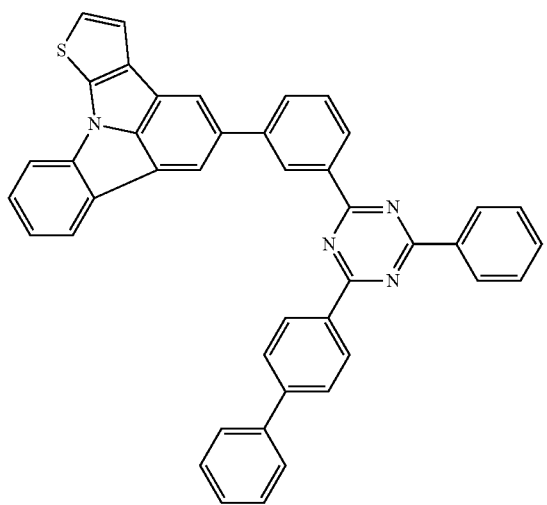
Compound 3
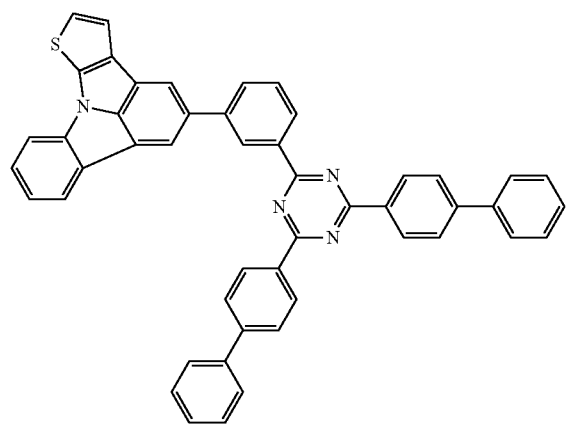
Compound 4
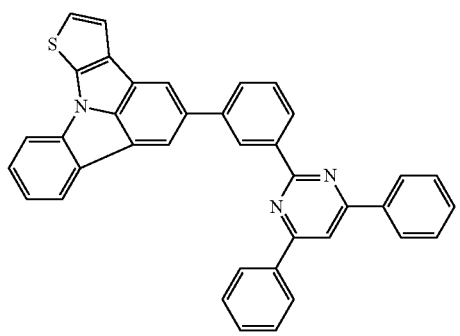
Compound 5
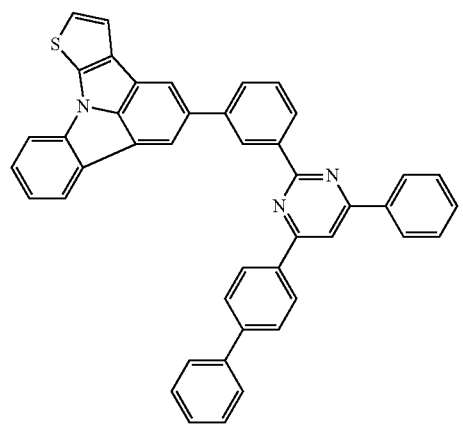
Compound 6
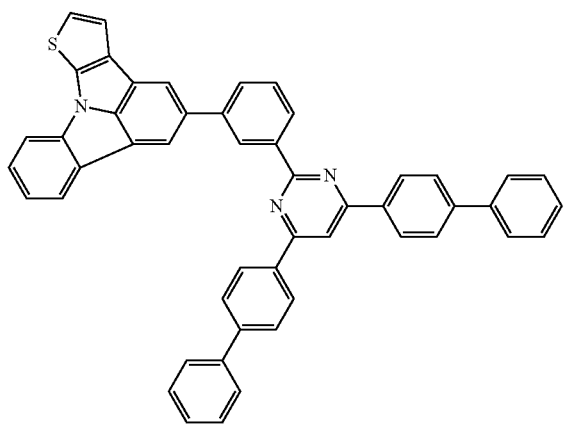

-continued
Compound 7
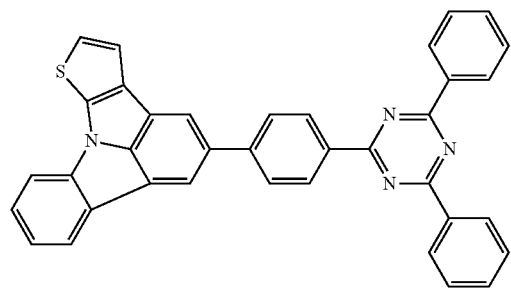
Compound 8
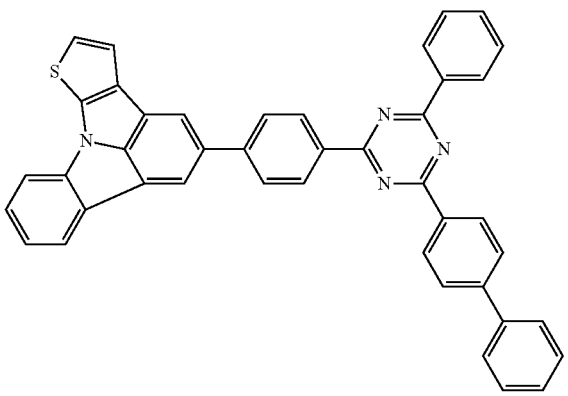
Compound 9
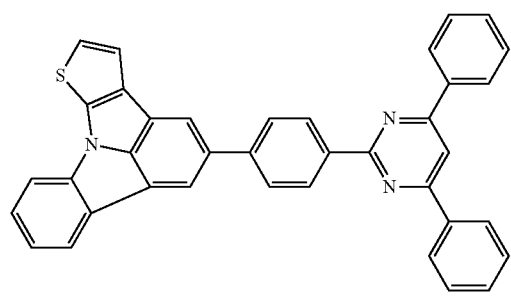
Compound 10
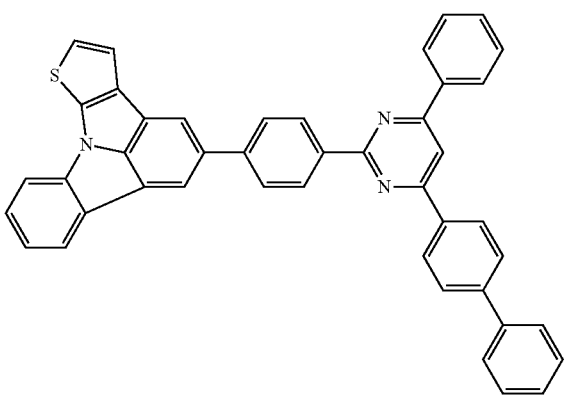
Compound 11
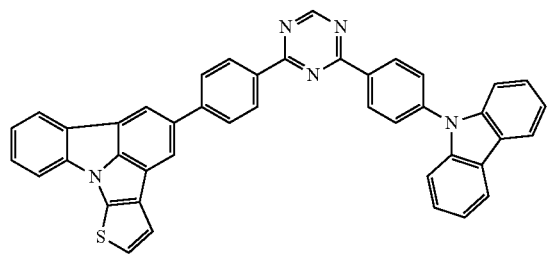
Compound 12
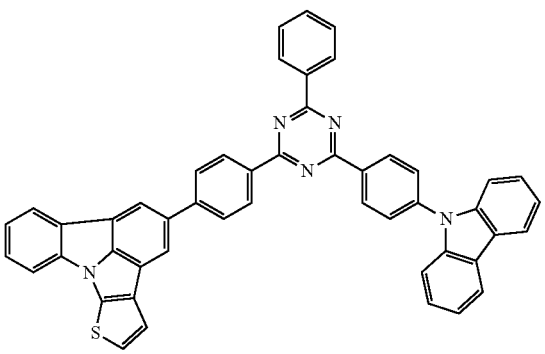
Compound 13
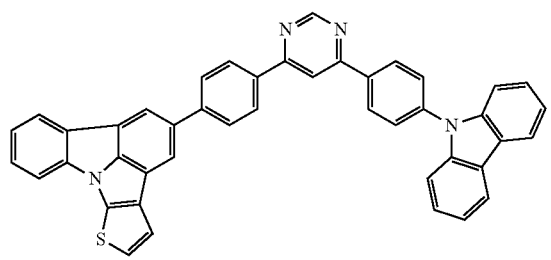
Compound 14
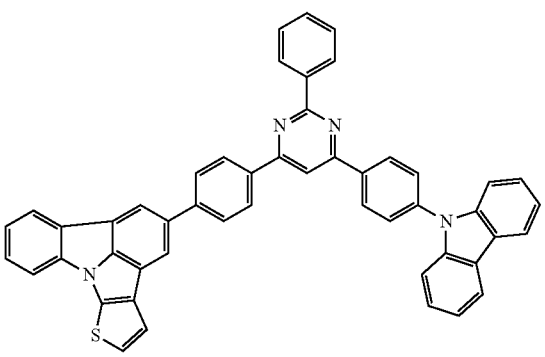

-continued
Compound 15
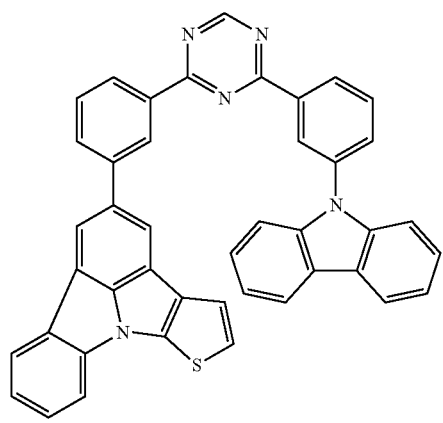
Compound 16
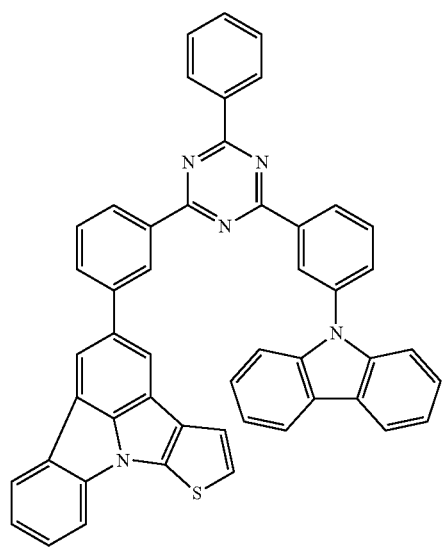
Compound 17
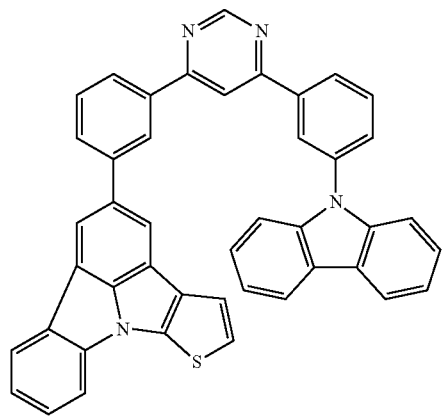
Compound 18
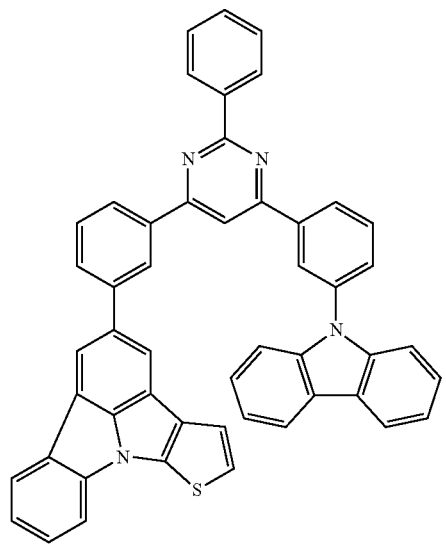
Compound 19
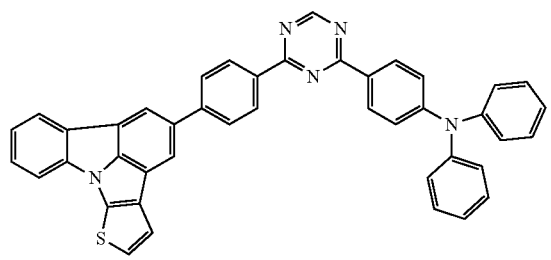
Compound 20
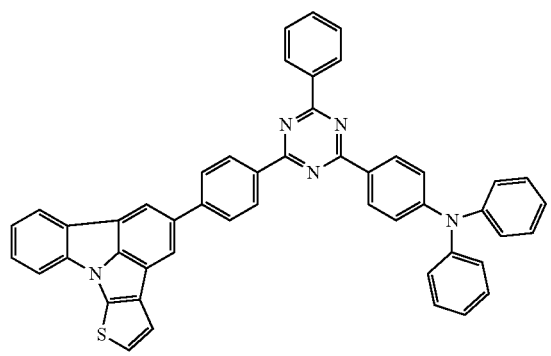

-continued
Compound 21
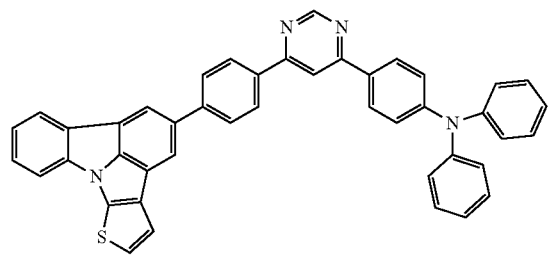
Compound 22
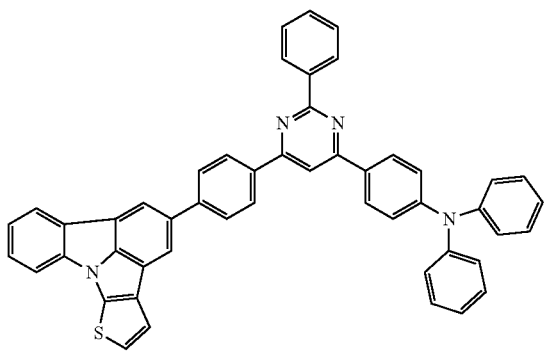
Compound 23
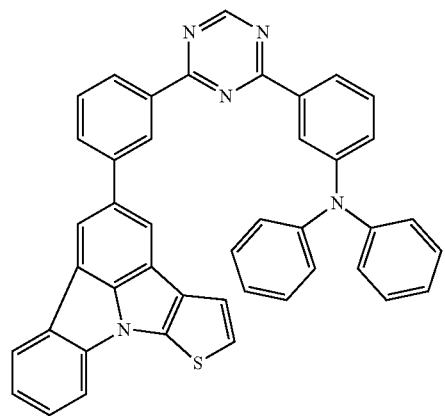
Compound 24
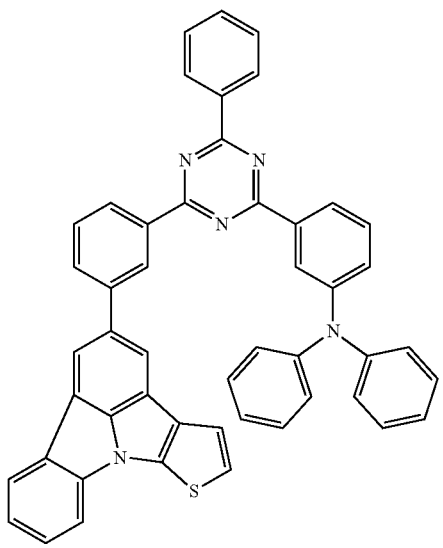
Compound 25
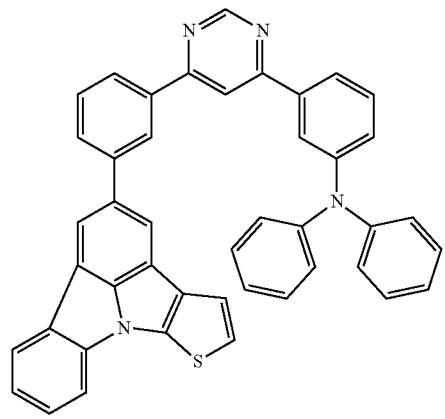
Compound 26
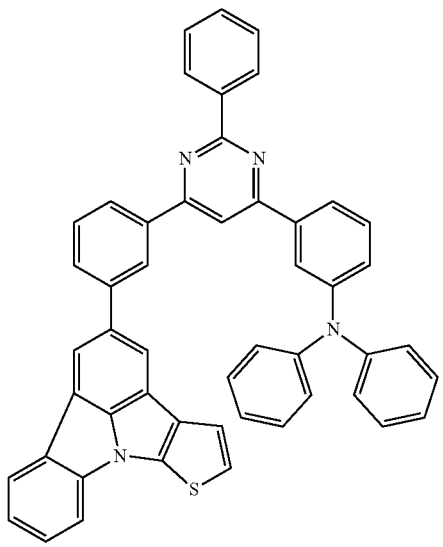

-continued
Compound 27
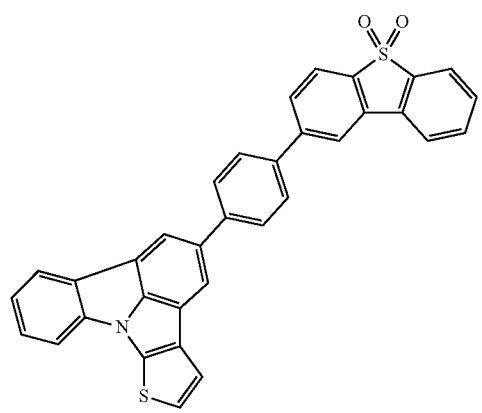
Compound 28
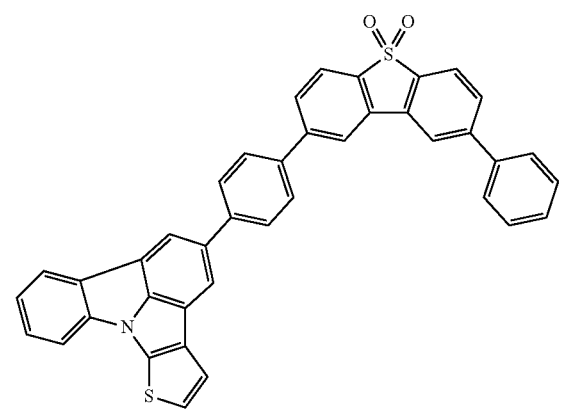
Compound 29
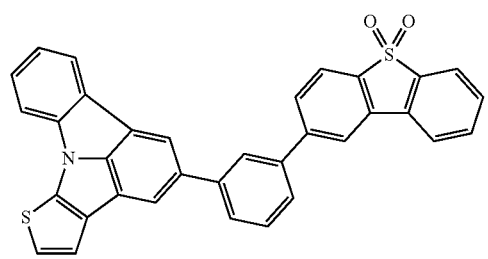
Compound 30
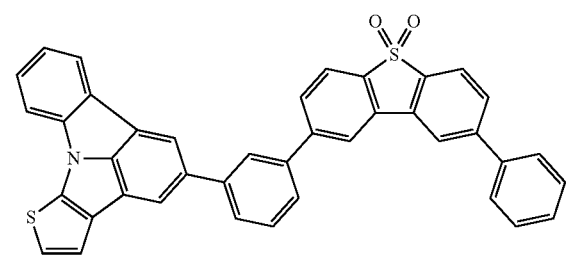
Compound 31
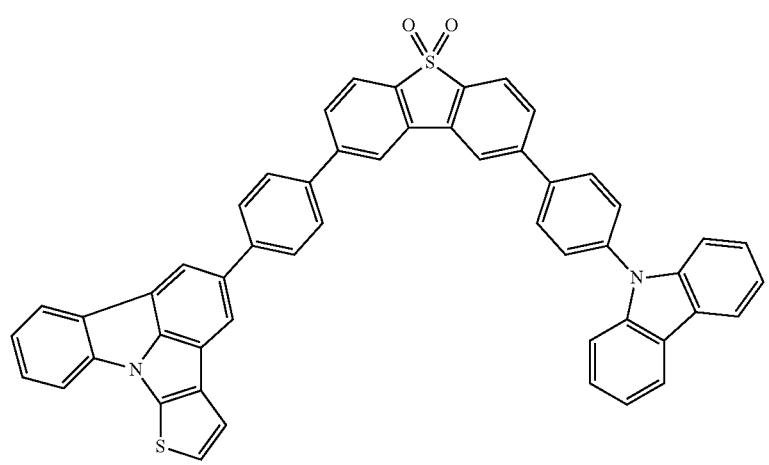

-continued
Compound 32
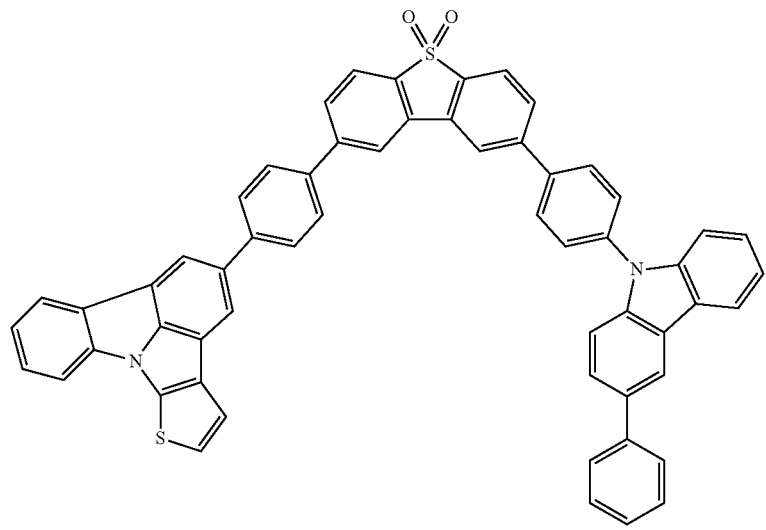
Compound 33
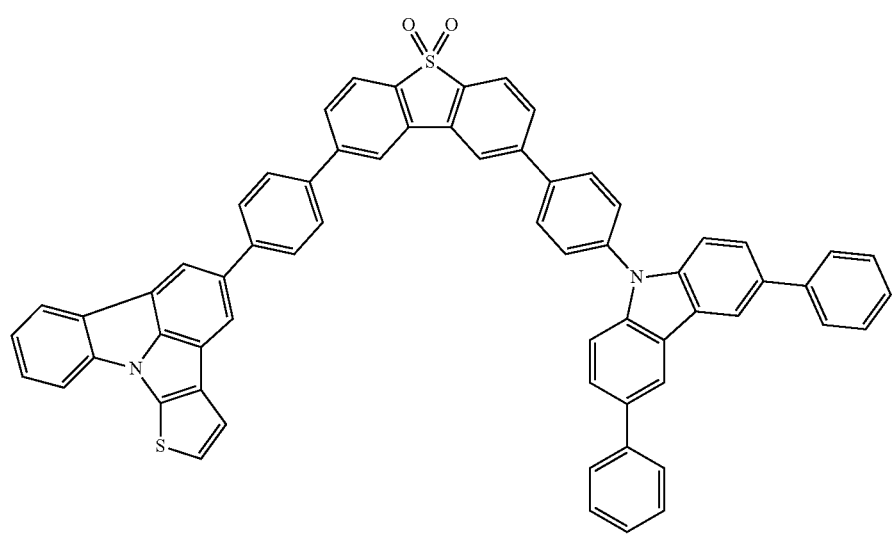
Compound 34
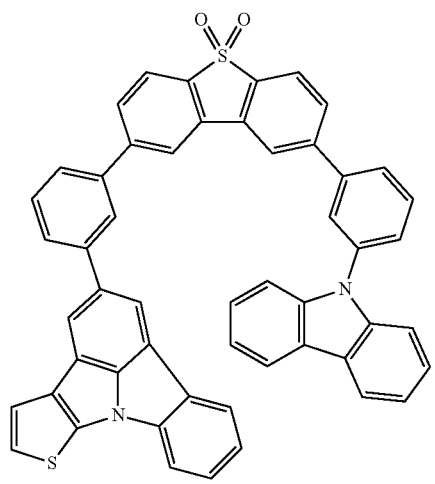
Compound 35
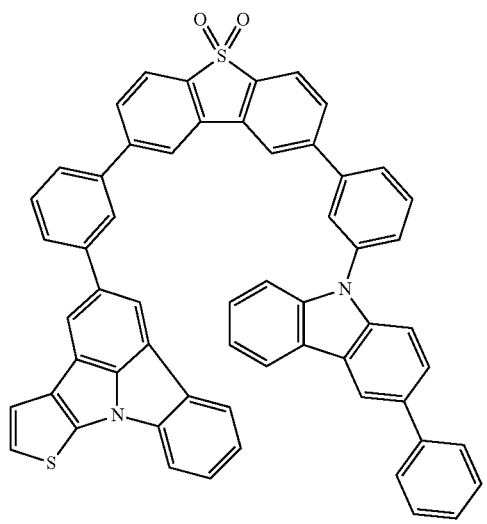

-continued
Compound 36
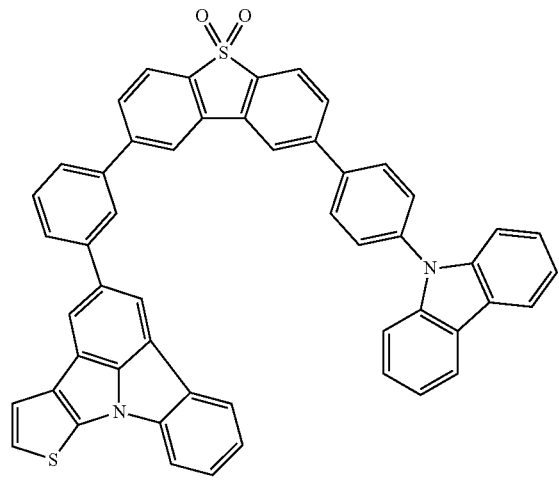
Compound 37
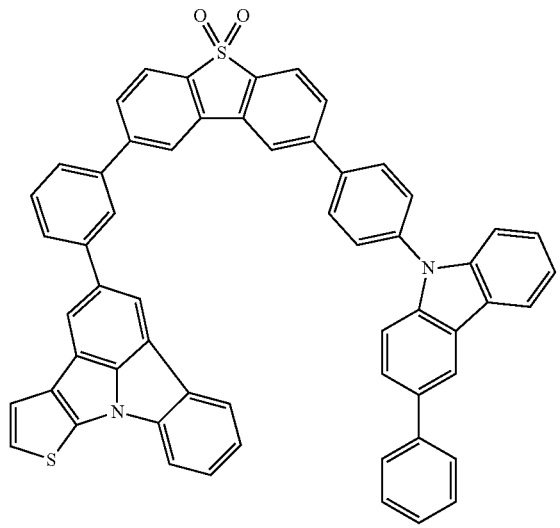
Compound 38
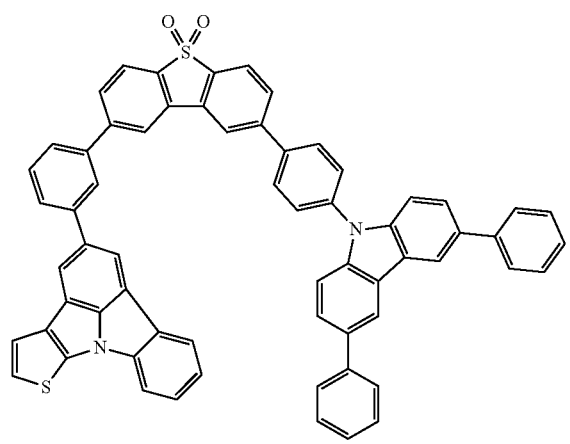
Compound 39
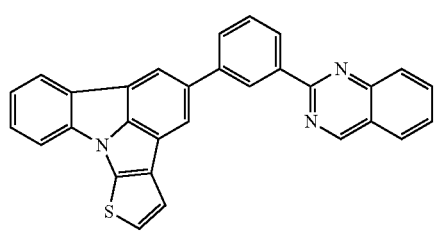
Compound 40
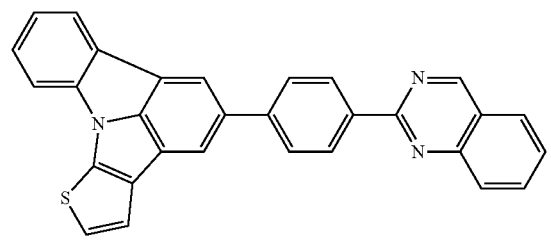
Compound 41
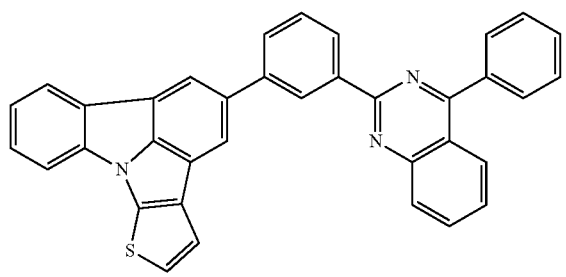
Compound 42
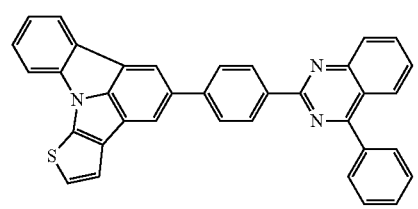
Compound 43
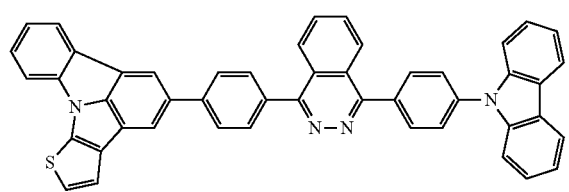

-continued
Compound 44
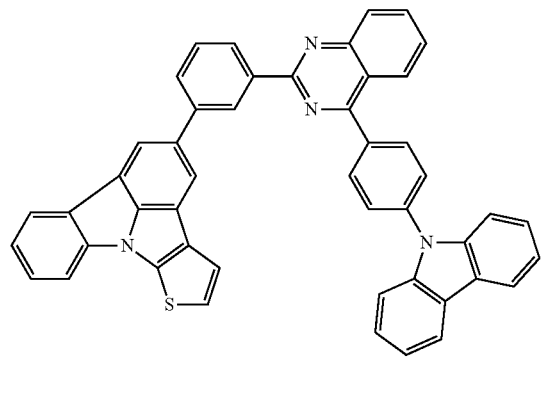
Compound 45
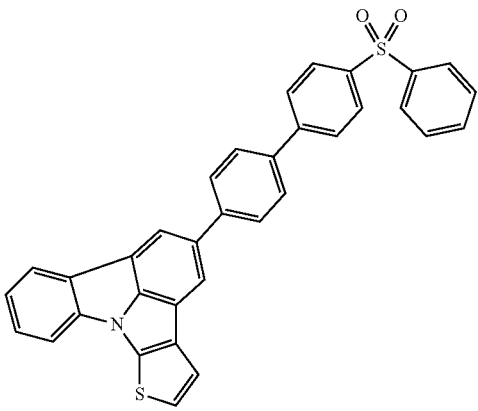
Compound 46
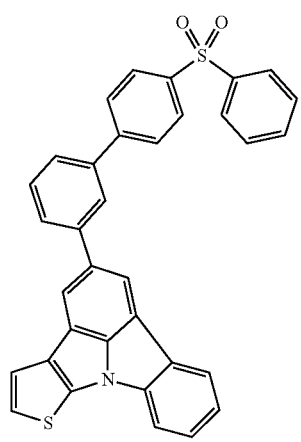
Compound 47
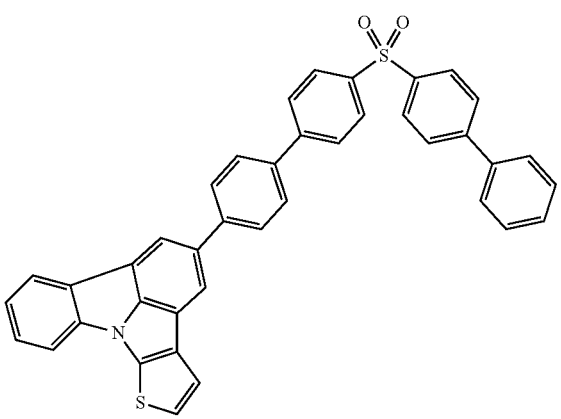
Compound 48
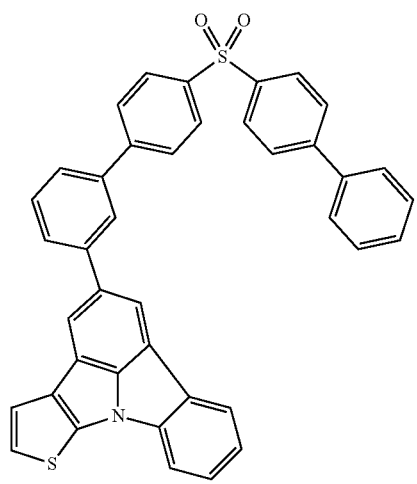

-continued
Compound 49
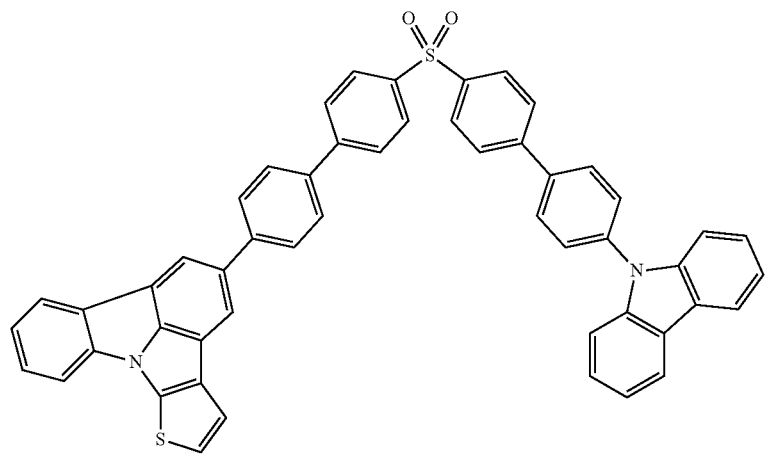
Compound 50
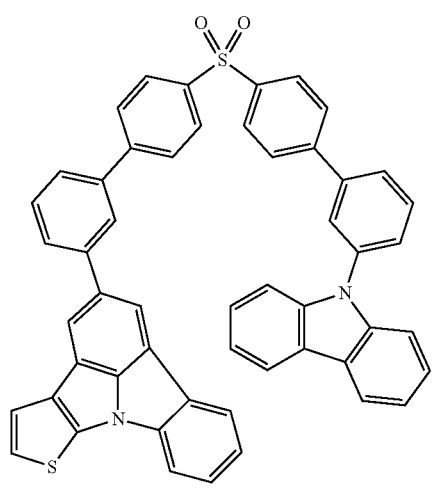
Compound 51
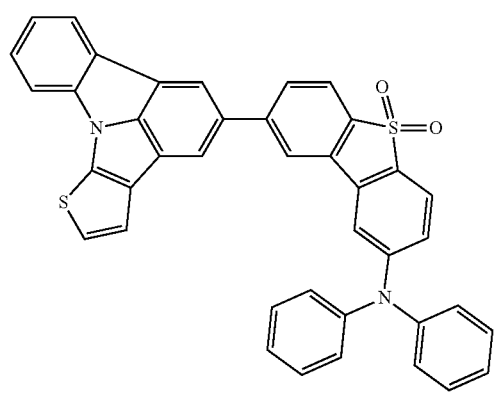
Compound 52
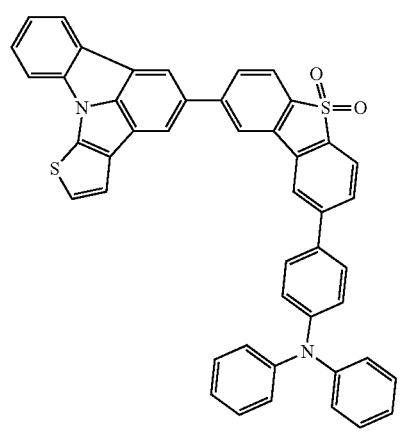
Compound 53
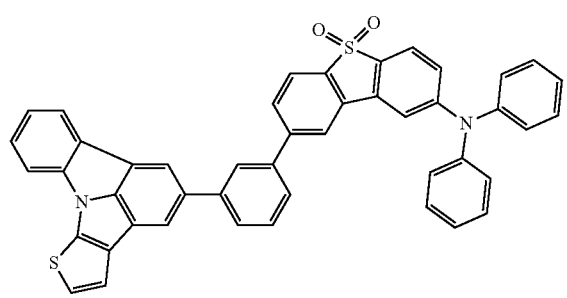

-continued
Compound 54
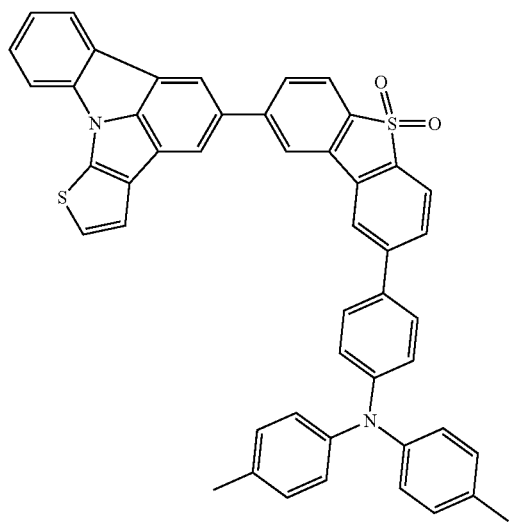
Compound 55
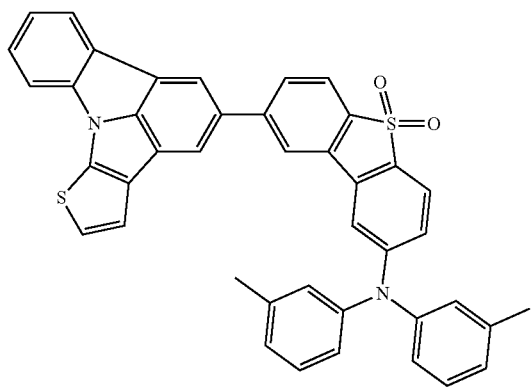
Compound 56
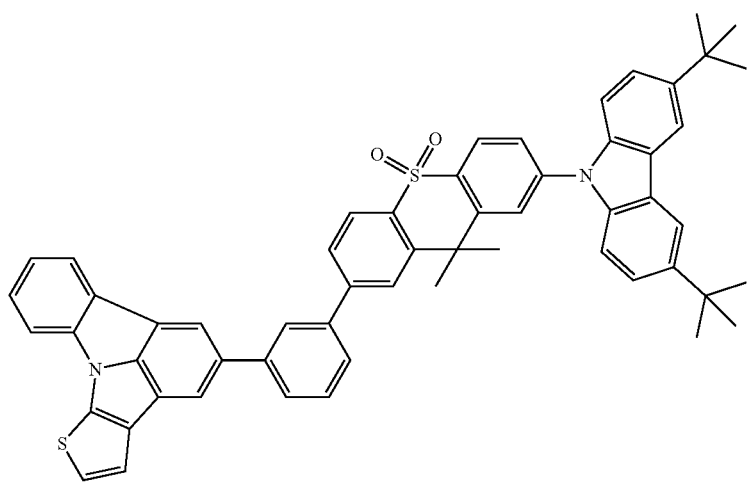
Compound 57
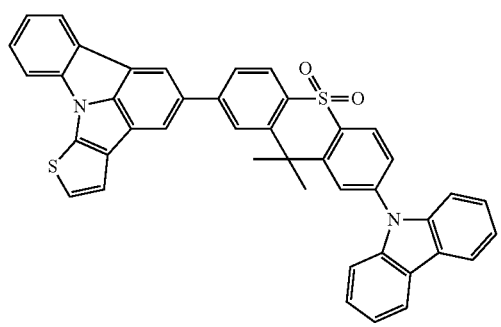
Compound 58
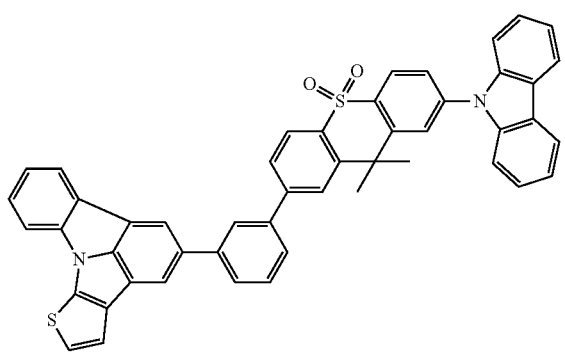

Compound 59
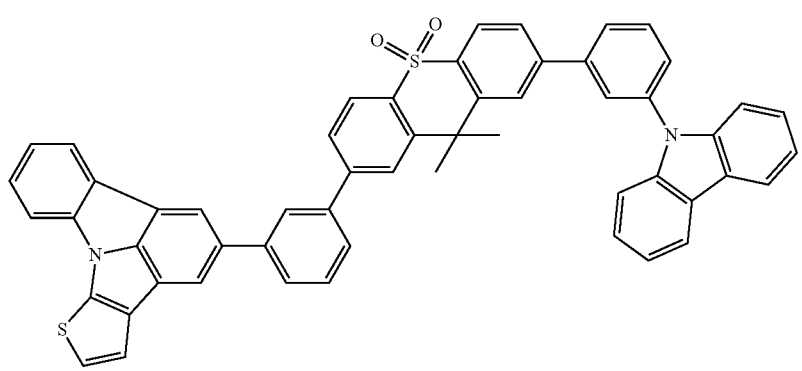
Compound 60
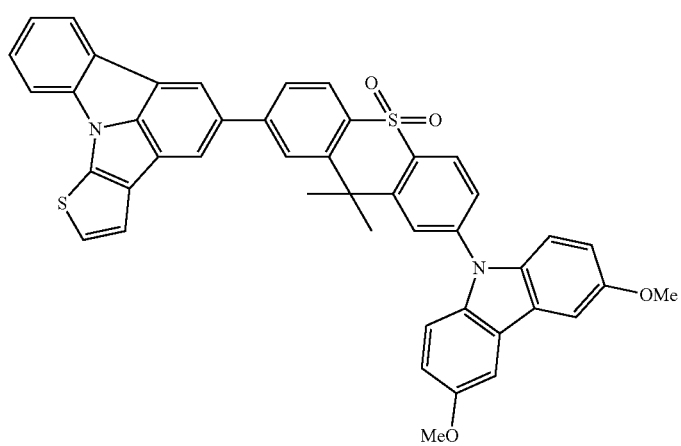
Compound 61
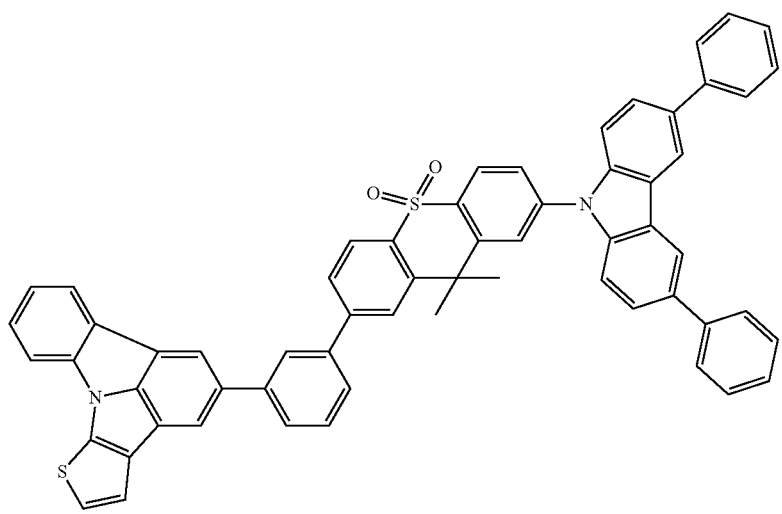
Compound 62
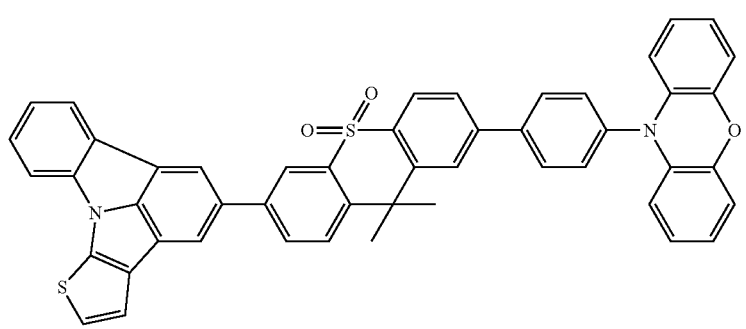

-continued
Compound 63
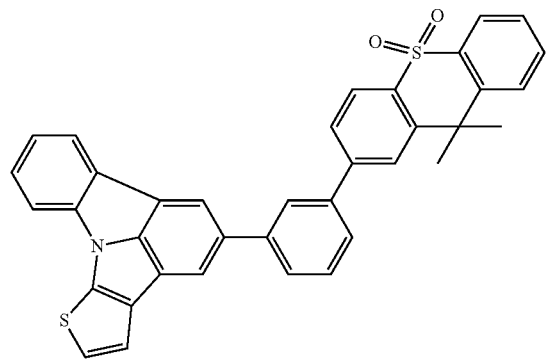
Compound 64
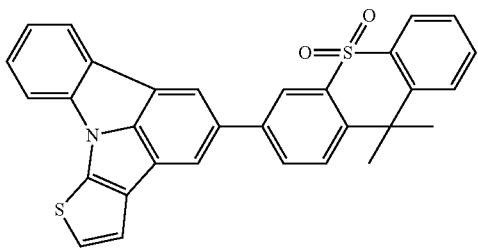
Compound 65
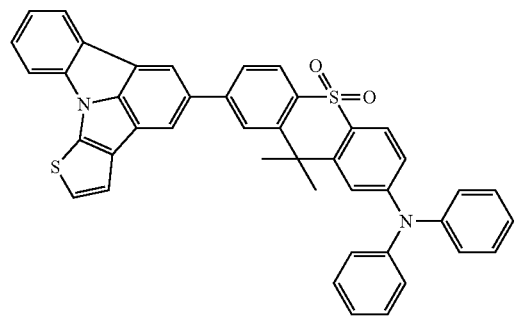
Compound 66
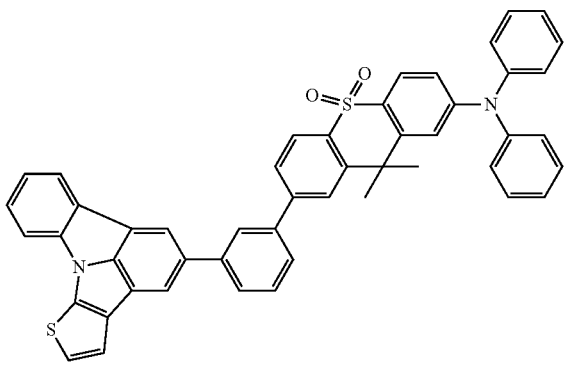
Compound 67
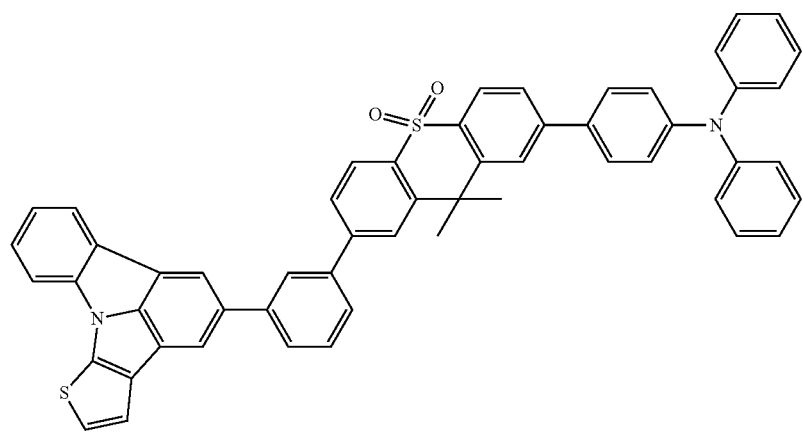
Compound 68
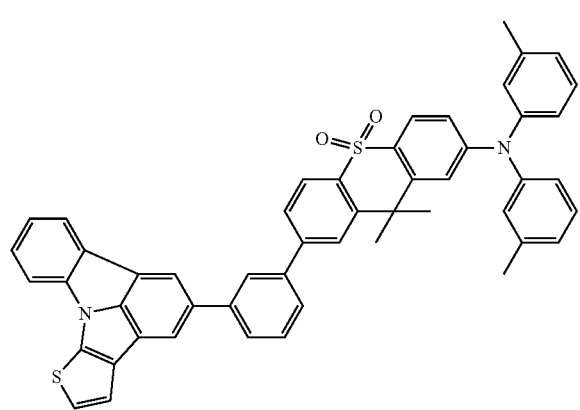
Compound 69
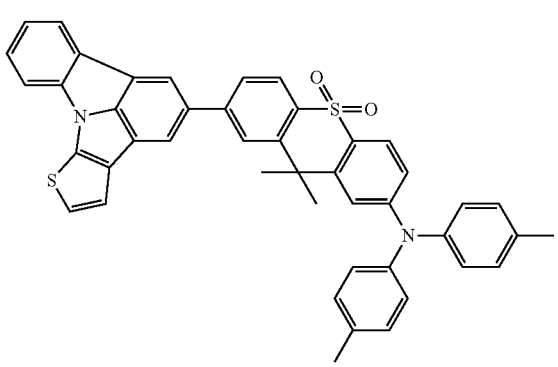

Compound 70
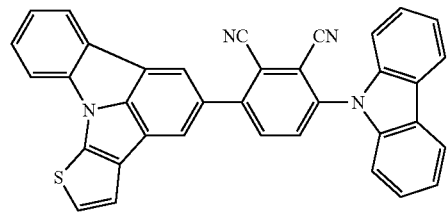
Compound 71
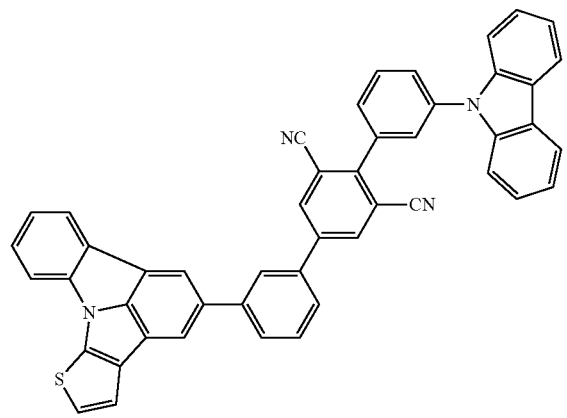
Compound 72
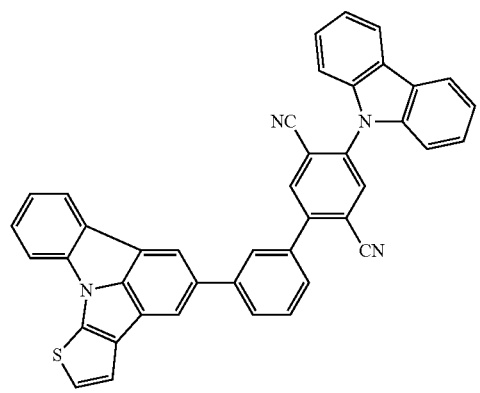
Compound 73
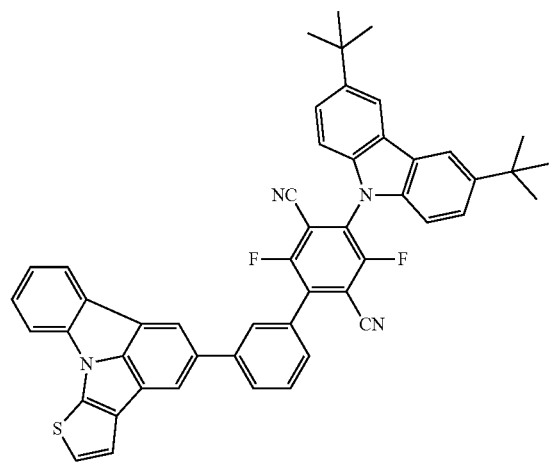
Compound 74
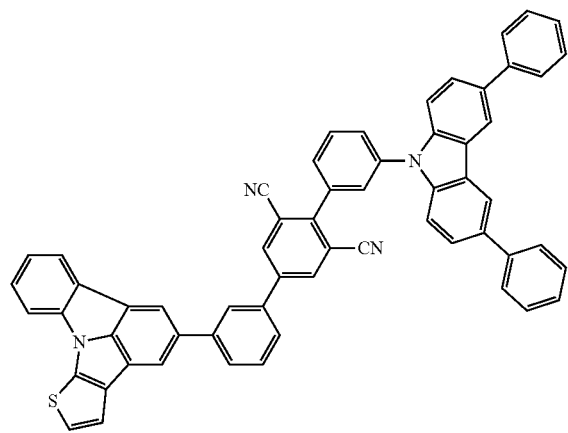
Compound 75
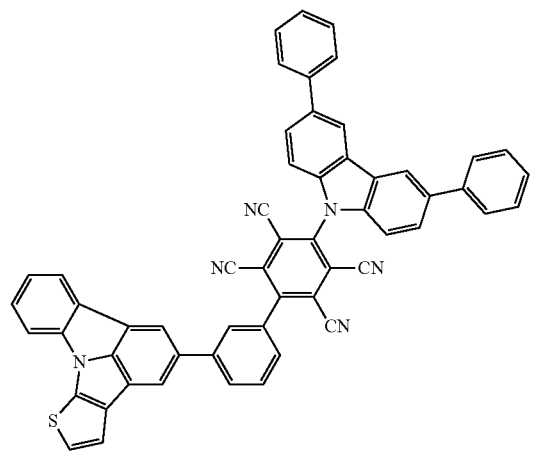

-continued
Compound 76
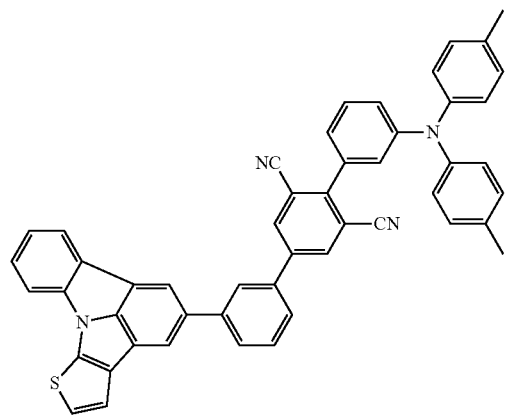
Compound 77
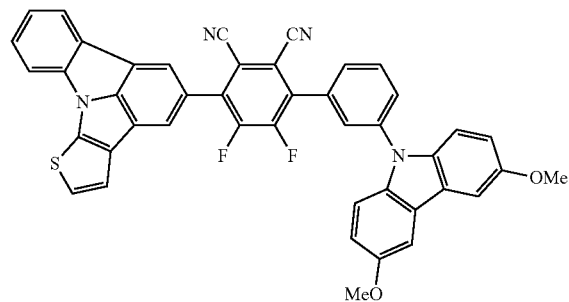
Compound 78
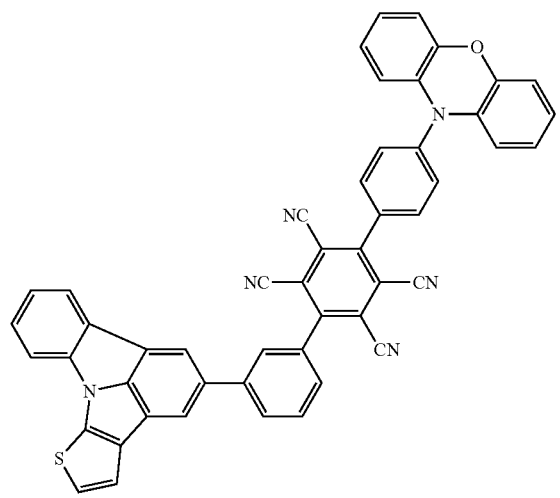
Compound 79
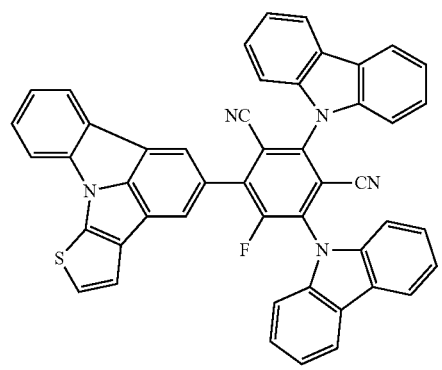
Compound 80
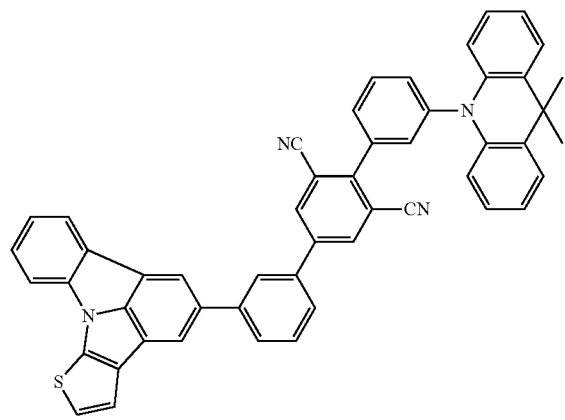
Compound 81
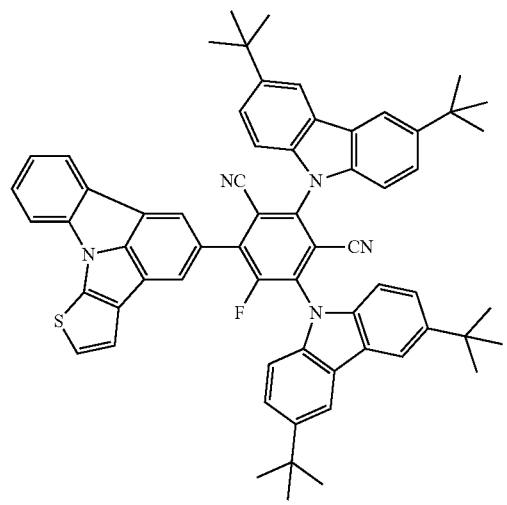

-continued
Compound 82
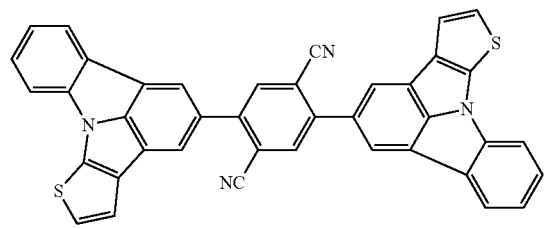
Compound 83
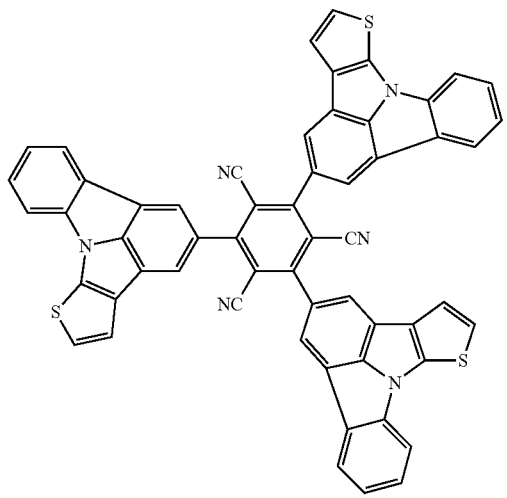
Compound 84
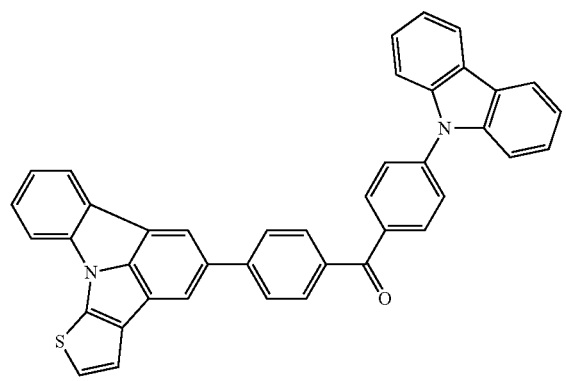
Compound 85
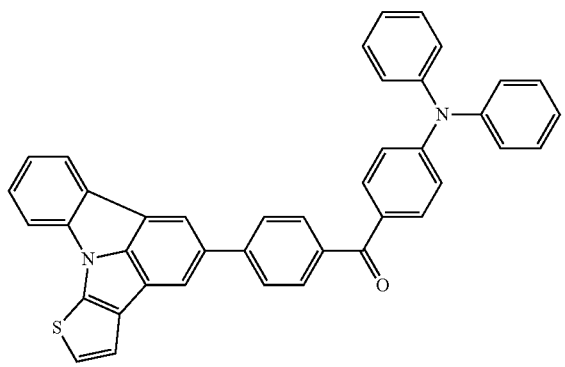
Compound 86
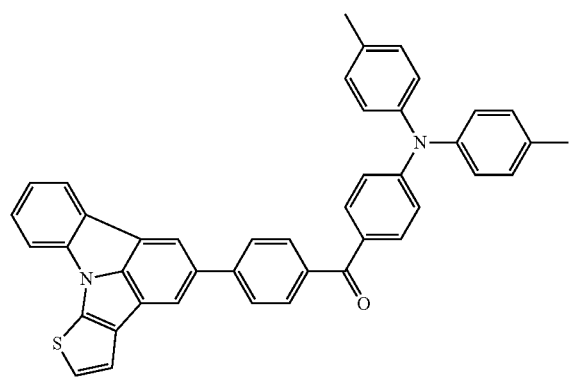
Compound 87
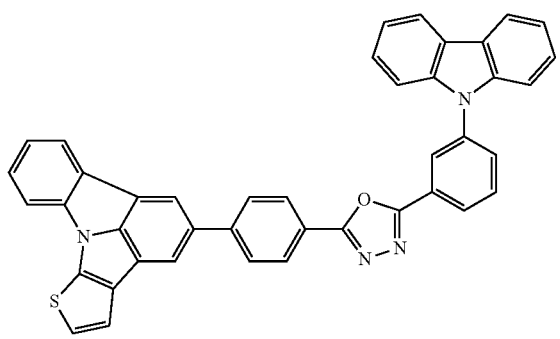

-continued
Compound 88
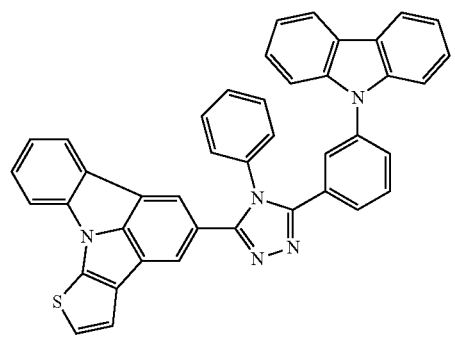
Compound 89
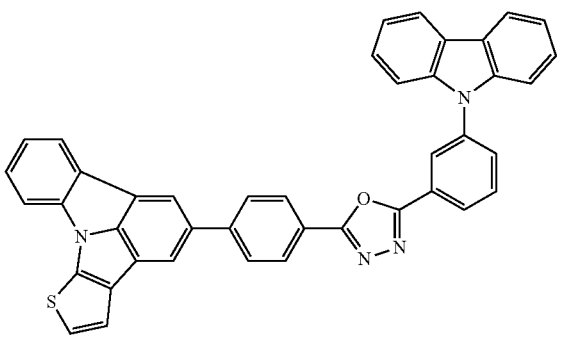
Compound 90
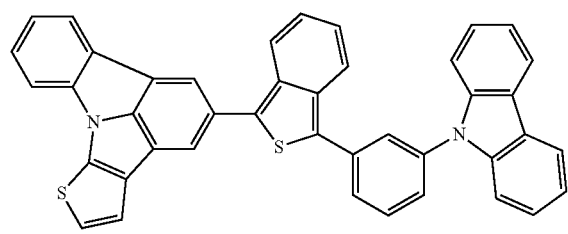
Compound 91
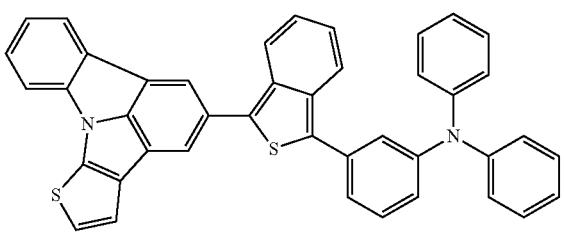
Compound 92
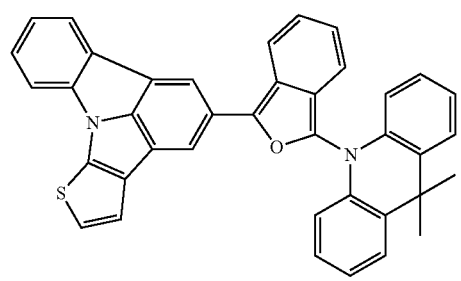
Compound 93
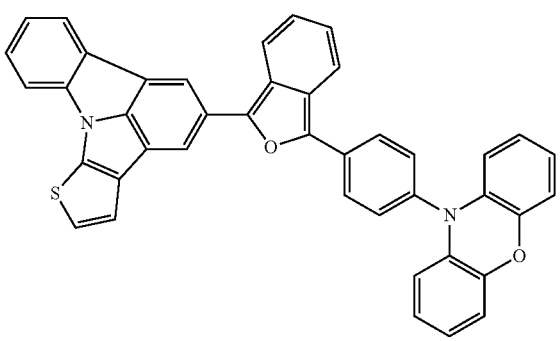
Compound 94
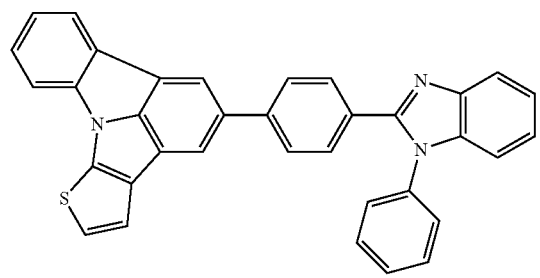
Compound 95
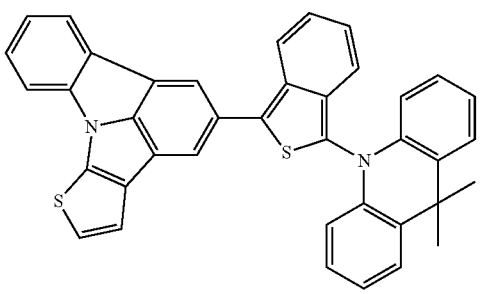
Compound 96
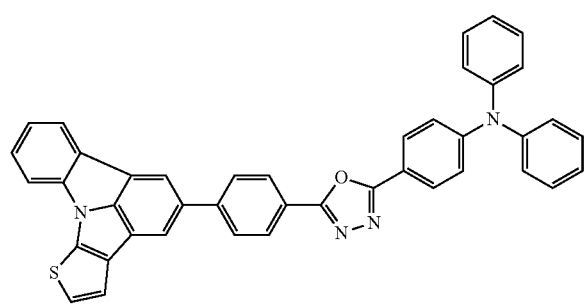
Compound 97
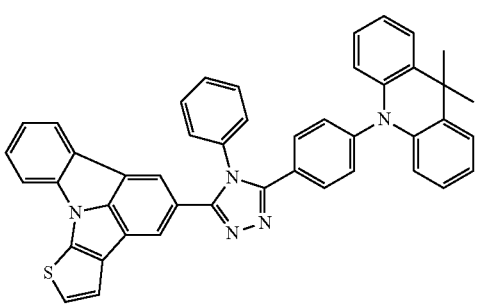

Compound 98

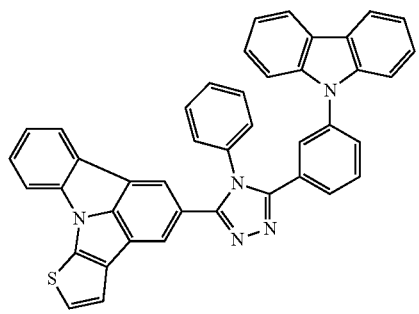

Compound 99

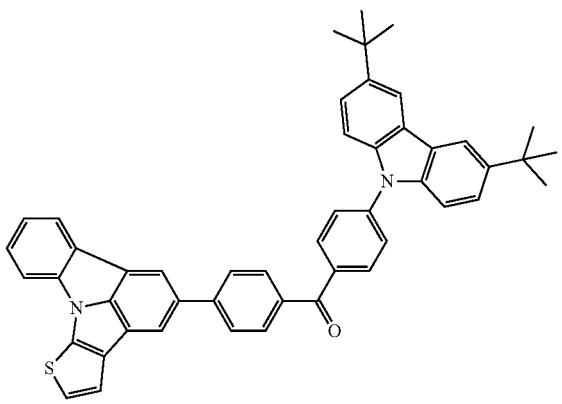

Compound 100

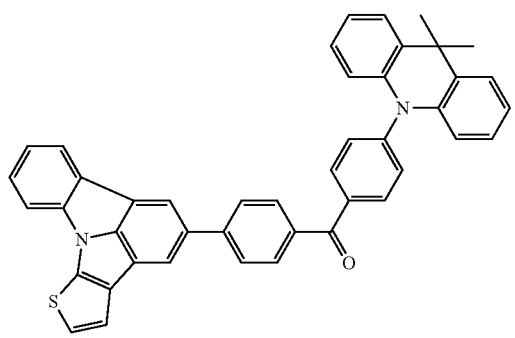

Compound 101

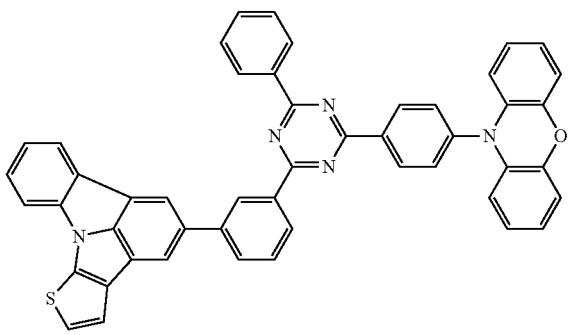

Compound 102

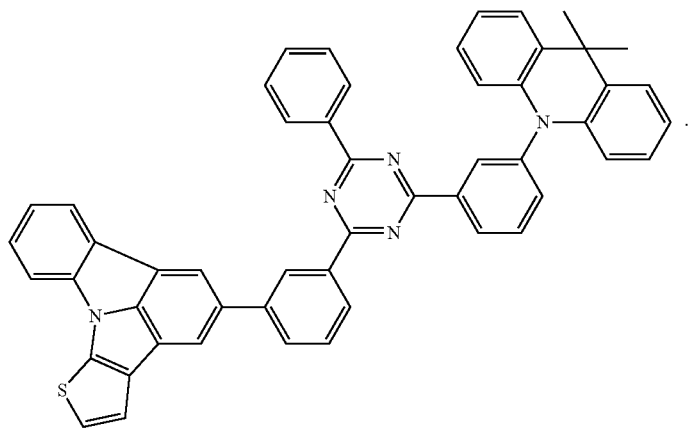

4. An organic electroluminescence device comprises a pair of electrodes consisting of a cathode and an anode, and between the pairs of electrodes comprise at least a light emitting layer, and one or more layers of organic thin film layer, wherein the light emitting layer comprises the organic material with a general formula (1) according to claim 1.

5. The organic electroluminescence device according to claim 4, wherein the light emitting layer comprises the delayed fluorescence material and/or a fluorescence material.

6. The organic electroluminescence device according to claim 4, wherein the light emitting layer comprises the delayed fluorescence material with a general formula (1) is a delayed fluorescence host material.

7. The organic electroluminescence device according to claim 4, wherein the light emitting layer comprises the delayed fluorescence material with a general formula (1) is a delayed fluorescence dopant material.

8. The organic electroluminescence device according to claim 4, wherein the light emitting layer comprises the second fluorescence dopant material.

9. The organic electroluminescence device according to claim 4, wherein the light emitting layer comprises a second fluorescence host material.

10. The organic electroluminescence device according to claim 4, wherein the light emitting layer comprises the organic compound with a general formula (1) is a phosphorescent host material.

11. The organic electroluminescence device according to claim 4, wherein the device is an organic light emitting device.

12. The organic electroluminescent device according to claim 4, wherein the device is a lighting panel.

13. The organic electroluminescent device according to claim 4, wherein the device is a backlight panel.

* * * * *